US012747273B2

(12) United States Patent
Carey et al.

(10) Patent No.: US 12,747,273 B2
(45) Date of Patent: Sep. 29, 2026

(54) HTT REPRESSORS COMPRISING A ZINC-FINGER PROTEIN TRANSCRIPTION FACTOR

(71) Applicants: Sangamo Therapeutics, Inc., Brisbane, CA (US); Takeda Pharmaceutical Company Limited, Osaka (JP)

(72) Inventors: Galen Carey, Lexington, MA (US); Matthew Chiocco, Southborough, MA (US); Vivian Choi, Lexington, MA (US); Brian Felice, Lexington, MA (US); Steven Froelich, Brisbane, CA (US); Debra Klatte, Lexington, MA (US); Jeffrey Miller, Brisbane, CA (US); David Paschon, Brisbane, CA (US); Edward Rebar, Brisbane, CA (US); Bryan Zeitler, Brisbane, CA (US); Lei Zhang, Brisbane, CA (US); H. Steve Zhang, Brisbane, CA (US)

(73) Assignees: Sangamo Therapeutics, Inc., Brisbane, CA (US); Takeda Pharmaceutical Company Limited, Osaka (JP)

( * ) Notice: Subject to any disclaimer, the term of this patent is extended or adjusted under 35 U.S.C. 154(b) by 1229 days.

(21) Appl. No.: 17/423,063

(22) PCT Filed: Jan. 15, 2020

(86) PCT No.: PCT/US2020/013661

§ 371 (c)(1),
(2) Date: Jul. 14, 2021

(87) PCT Pub. No.: WO2020/150338

PCT Pub. Date: Jul. 23, 2020

(65) Prior Publication Data

US 2022/0064237 A1 Mar. 3, 2022

Related U.S. Application Data

(60) Provisional application No. 62/792,701, filed on Jan. 15, 2019.

(51) Int. Cl.

| | |
|---|---|
| ***C07K 14/47*** | (2006.01) |
| ***A61K 38/00*** | (2006.01) |
| ***A61K 48/00*** | (2006.01) |
| ***A61P 25/14*** | (2006.01) |
| ***C12N 15/86*** | (2006.01) |

(52) U.S. Cl.

CPC ........ *C07K 14/4703* (2013.01); *A61K 48/005* (2013.01); *A61P 25/14* (2018.01); *C12N 15/86* (2013.01); *A61K 38/00* (2013.01); *C07K 2319/09* (2013.01); *C07K 2319/81* (2013.01); *C12N 2750/14143* (2013.01)

(58) Field of Classification Search

CPC ............ C07K 14/4703; C07K 2319/09; C07K 2319/81; A61K 48/005; A61K 38/00; A61P 25/14; C12N 15/86; C12N 2750/14143

See application file for complete search history.

(56) References Cited

U.S. PATENT DOCUMENTS

| | | | |
|---|---|---|---|
| 4,186,183 | A | 1/1980 | Steck et al. |
| 4,217,344 | A | 8/1980 | Vanlerberghe et al. |
| 4,235,871 | A | 11/1980 | Papahadjopoulos et al. |
| 4,261,975 | A | 4/1981 | Fullerton et al. |
| 4,485,054 | A | 11/1984 | Mezei et al. |
| 4,501,728 | A | 2/1985 | Geho et al. |
| 4,774,085 | A | 9/1988 | Fidler |
| 4,797,368 | A | 1/1989 | Carter et al. |
| 4,837,028 | A | 6/1989 | Allen |
| 4,897,355 | A | 1/1990 | Eppstein et al. |
| 4,946,787 | A | 8/1990 | Eppstein et al. |
| 5,049,386 | A | 9/1991 | Eppstein et al. |
| 5,173,414 | A | 12/1992 | Lebkowski et al. |
| 5,176,996 | A | 1/1993 | Hogan et al. |
| 5,420,032 | A | 5/1995 | Marshall et al. |
| 5,422,251 | A | 6/1995 | Fresco |
| 5,585,245 | A | 12/1996 | Johnsson et al. |
| 5,789,538 | A | 8/1998 | Rebar et al. |
| 5,925,523 | A | 7/1999 | Dove et al. |
| 5,928,638 | A | 7/1999 | Uchida et al. |
| 6,007,988 | A | 12/1999 | Choo et al. |

(Continued)

FOREIGN PATENT DOCUMENTS

| | | | |
|---|---|---|---|
| CA | 2769262 | A1 | 2/2011 |
| CN | 104204225 | A | 12/2014 |

(Continued)

OTHER PUBLICATIONS

Beerli et al., Engineering polydactyl zinc-finger transcription factors, 2002, Nat. Biotech., 20, 135-141. (Year: 2002).*

(Continued)

*Primary Examiner* — Soren Harward
*Assistant Examiner* — Keyur A Vyas
(74) *Attorney, Agent, or Firm* — Foley & Lardner LLP

(57) ABSTRACT

Disclosed herein are HTT repressors and methods and compositions for use of these HTT repressors. Disclosed herein are methods and compositions for diagnosing, preventing and/or treating Huntington's Disease. In particular, provided herein are methods and compositions for modifying (e.g., modulating expression of) an HD HTT allele so as to prevent or treat Huntington Disease, including mHTT repressors (that repress mHTT transcripts and thus also repress mHTT protein expression).

10 Claims, 15 Drawing Sheets

Specification includes a Sequence Listing.

(56) References Cited

U.S. PATENT DOCUMENTS

| | | | |
|---|---|---|---|
| 6,008,336 | A | 12/1999 | Hanson et al. |
| 6,013,453 | A | 1/2000 | Choo et al. |
| 6,140,081 | A | 10/2000 | Barbas |
| 6,200,759 | B1 | 3/2001 | Dove et al. |
| 6,309,634 | B1 | 10/2001 | Bankiewicz et al. |
| 6,453,242 | B1 | 9/2002 | Eisenberg et al. |
| 6,503,717 | B2 | 1/2003 | Case et al. |
| 6,534,261 | B1 | 3/2003 | Cox et al. |
| 6,599,692 | B1 | 7/2003 | Case et al. |
| 6,607,882 | B1 | 8/2003 | Cox et al. |
| 6,689,558 | B2 | 2/2004 | Case |
| 6,746,838 | B1 | 6/2004 | Choo et al. |
| 6,824,978 | B1 | 11/2004 | Cox et al. |
| 6,833,252 | B1 | 12/2004 | Dujon et al. |
| 6,866,997 | B1 | 3/2005 | Choo et al. |
| 6,933,113 | B2 | 8/2005 | Case et al. |
| 6,953,575 | B2 | 10/2005 | Bankiewicz et al. |
| 6,979,539 | B2 | 12/2005 | Cox et al. |
| 7,013,219 | B2 | 3/2006 | Case et al. |
| 7,067,317 | B2 | 6/2006 | Rebar et al. |
| 7,074,596 | B2 | 7/2006 | Darzynkiewicz et al. |
| 7,163,824 | B2 | 1/2007 | Cox et al. |
| 7,182,944 | B2 | 2/2007 | Bankiewicz |
| 7,241,573 | B2 | 7/2007 | Choo et al. |
| 7,241,574 | B2 | 7/2007 | Choo et al. |
| 7,262,054 | B2 | 8/2007 | Jamieson et al. |
| 7,837,668 | B2 | 11/2010 | Gasmi et al. |
| 7,888,121 | B2 | 2/2011 | Urnov et al. |
| 7,914,796 | B2 | 3/2011 | Miller et al. |
| 7,951,925 | B2 | 5/2011 | Ando et al. |
| 7,972,854 | B2 | 7/2011 | Miller et al. |
| 8,034,598 | B2 | 10/2011 | Miller |
| 8,092,429 | B2 | 1/2012 | Gasmi et al. |
| 8,110,379 | B2 | 2/2012 | Dekelver et al. |
| 8,153,773 | B2 | 4/2012 | Jemielity et al. |
| 8,309,355 | B2 | 11/2012 | Bankiewicz et al. |
| 8,337,458 | B2 | 12/2012 | Bankiewicz et al. |
| 8,409,861 | B2 | 4/2013 | Guschin et al. |
| 8,586,526 | B2 | 11/2013 | Gregory et al. |
| 8,597,912 | B2 | 12/2013 | Collingwood et al. |
| 8,623,618 | B2 | 1/2014 | Doyon et al. |
| 8,703,489 | B2 | 4/2014 | Wang |
| 8,841,260 | B2 | 9/2014 | Miller et al. |
| 8,945,868 | B2 | 2/2015 | Collingwood et al. |
| 8,956,828 | B2 | 2/2015 | Bonini et al. |
| 9,005,973 | B2 | 4/2015 | Cost et al. |
| 9,045,763 | B2 | 6/2015 | Dekelver et al. |
| 9,050,299 | B2 | 6/2015 | Bankiewicz |
| 9,089,667 | B2 | 7/2015 | Bankiewicz |
| 9,234,016 | B2 | 1/2016 | Gregory et al. |
| 9,499,597 | B2 | 11/2016 | Miller et al. |
| 9,624,498 | B2 | 4/2017 | Froelich et al. |
| 9,943,565 | B2 | 4/2018 | Gregory et al. |
| 10,435,441 | B2 * | 10/2019 | Froelich ............. A61K 48/0075 |
| 11,123,443 | B2 * | 9/2021 | Froelich ............... C12N 5/0619 |
| 11,421,007 | B2 * | 8/2022 | Froelich ............. C07K 14/4703 |
| 2003/0232410 | A1 | 12/2003 | Liljedahl et al. |
| 2005/0026157 | A1 | 2/2005 | Baltimore et al. |
| 2005/0064474 | A1 | 3/2005 | Urnov et al. |
| 2005/0208489 | A1 | 9/2005 | Carroll et al. |
| 2006/0063231 | A1 | 3/2006 | Li et al. |
| 2006/0239966 | A1 | 10/2006 | Tornoe et al. |
| 2007/0117128 | A1 | 5/2007 | Smith et al. |
| 2007/0218528 | A1 | 9/2007 | Miller |
| 2008/0159996 | A1 | 7/2008 | Ando et al. |
| 2009/0068164 | A1 | 3/2009 | Segal et al. |
| 2009/0111119 | A1 | 4/2009 | Doyon et al. |
| 2010/0218264 | A1 | 8/2010 | Cui et al. |
| 2011/0265198 | A1 | 10/2011 | Gregory et al. |
| 2012/0017290 | A1 | 1/2012 | Cui et al. |
| 2012/0195936 | A1 | 8/2012 | Rudolph et al. |
| 2013/0122591 | A1 | 5/2013 | Cost et al. |
| 2013/0137104 | A1 | 5/2013 | Cost et al. |
| 2013/0177960 | A1 | 7/2013 | Rebar |
| 2013/0177983 | A1 | 7/2013 | Rebar |
| 2013/0196373 | A1 | 8/2013 | Gregory et al. |
| 2013/0253040 | A1 | 9/2013 | Miller et al. |
| 2015/0056705 | A1 | 2/2015 | Conway et al. |
| 2015/0335708 | A1 | 11/2015 | Froelich et al. |
| 2016/0296605 | A1 | 10/2016 | Zhang |
| 2017/0035839 | A1 | 2/2017 | Miller et al. |
| 2017/0096460 | A1 | 4/2017 | Froelich et al. |
| 2018/0087072 | A1 | 3/2018 | Miller et al. |
| 2018/0200332 | A1 | 7/2018 | Gregory et al. |
| 2019/0322711 | A1 | 10/2019 | Froelich et al. |

FOREIGN PATENT DOCUMENTS

| | | | |
|---|---|---|---|
| CN | 105934524 | A | 9/2016 |
| CN | 106413760 | A | 2/2017 |
| CN | 108348576 | A | 7/2018 |
| JP | 2013-500045 | A | 1/2013 |
| JP | 2015-509958 | | 4/2015 |
| JP | 2018-532428 | | 11/2018 |
| JP | 2021-521775 | A | 8/2021 |
| WO | WO-91/16024 | | 10/1991 |
| WO | WO-91/17424 | | 11/1991 |
| WO | WO-93/24641 | | 12/1993 |
| WO | WO-94/26877 | | 11/1994 |
| WO | WO-95/19431 | | 7/1995 |
| WO | WO-96/06166 | | 2/1996 |
| WO | WO-98/44350 | | 10/1998 |
| WO | WO-98/53057 | | 11/1998 |
| WO | WO-98/53058 | | 11/1998 |
| WO | WO-98/53059 | | 11/1998 |
| WO | WO-98/53060 | | 11/1998 |
| WO | WO-98/54311 | | 12/1998 |
| WO | WO-00/27878 | | 5/2000 |
| WO | WO-00/42219 | | 7/2000 |
| WO | WO-01/60970 | | 8/2001 |
| WO | WO-01/88197 | | 11/2001 |
| WO | WO-02/16536 | | 2/2002 |
| WO | WO-02/099084 | | 12/2002 |
| WO | WO-03/016496 | | 2/2003 |
| WO | WO-2007/139898 | | 12/2007 |
| WO | WO-2010/079430 | | 7/2010 |
| WO | WO-2015/070212 | A1 | 5/2015 |
| WO | WO-2015/171932 | A1 | 11/2015 |
| WO | WO-2017/053753 | A1 | 3/2017 |
| WO | WO-2017/077329 | A2 | 5/2017 |

OTHER PUBLICATIONS

Partial Supplementary European Search Report on EP 20740948.3 DTD Sep. 5, 2022, 10 pages.

Zeitler, et al., Allele-selective transcriptional repression of mutant HTT for the treatment of Huntington's disease, Nature Medicine, 25(7):1131-1142 (2019).

ECCO, "A tale of domestication: the endovirome, its polydactyl controllers and the species-specificity of human biology," Development, 2017, 144, 2719-29.

Extended European Search Report for EP Application No. 20740948.3, dated Dec. 19, 2022, 10 pgs.

Office Action in JP Application No. 2021-540305, mailed Dec. 21, 2023, 11 pgs. (with translation).

Garriga-Canut, M., et al., "Synthetic zinc finger repressors reduce mutant huntingtin expression in the brain of R6/2 mice," Proceedings of the National Academy of Sciences, vol. 109, Oct. 10, 2012, pp. E3136-E3145.

Office Action in CN Application No. 202080009478.4, dated May 23, 2024, 14 pgs. (with translation).

Agustin-Pavon, et al., "Deimmunization for gene therapy: host matching of synthetic zinc finger constructs enables long-term mutant huntingtin repression in mice," Molecular Neurodegeneration, vol. 11, Iss. 64, pp. 1-16 (2016).

Ahmad et al., "Antibody-mediated Specific Binding and Cytotoxicity of Liposome-entrapped Doxorubicin to Lung Cancer Cells in Vitro", Cancer Research, vol. 52, Sep. 1, 1992, pp. 4817-4820 (4 pages).

Alvarez et al., "Clinical Protocol: A Phase I Study of Recombinant Adenovirus Vector-Mediated Intraperitoneal Delivery of Herpes

(56) References Cited

OTHER PUBLICATIONS

Simplex Virus Thymidine Kinase (HSV-TK) Gene and Intravenous Ganciclovir for Previously Treated Ovarian and Extraovarian Cancer Patients", Human Gene Therapy, vol. 8, Mar. 20, 1997, pp. 597-613 (17 pages).
Anderson, W. French, "Human Gene Therapy", SCIENCE, vol. 256, May 8, 1992, pp. 808-813 (6 pages).
Argast et al., "I-Ppol and I-Crel Homing Site Sequence Degeneracy Determined by Random Mutagenesis and Sequential in Vitro Enrichment", Journal of Molecular Biology, vol. 280, No. mb981886, 1998, 345-353 (9 pages).
Ashworth et al., "Computational redesign of endonuclease DNA binding and cleavage specificity", Nature, vol. 44, Jun. 1, 2006, pp. 656-659 (4 pages).
Beerli et al., "Toward controlling gene expression at will: specific regulation of the erbB-2/HER-2 promoter by using polydactyl zinc finger proteins constructed from modular building blocks," Proc Natl Acad Sci USA, vol. 95, No. 25, Dec. 8, 1998, pp. 14623-14633 (6 pages).
Behr et al., "Gene Transfer with Synthetic Cationic Amphiphiles: Prospects for Gene Therapy", Bioconjugate Chemistry, vol. 5, 1994, pp. 382-389 (8 pages).
Belfort et al., "Homing endonucleases: keeping the house in order", Nucleic Acids Research, vol. 25, No. 17, 1997, pp. 3379-3388 (10 pages).
Beurdeley et al., "Compact designer TALENs for efficient genome engineering", Nature Communications, vol. 4, Apr. 23, 2013, pp. 1-8, DOI: 10.1038/ncomms2782 (8 pages).
Bird et al., "Methylation-Induced Repression—Belts, Braces, and Chromatin", Cell, vol. 99, Nov. 24, 1999, pp. 451-454 (4 pages).
Bitko et al., "Persistant Activation of RelA by Respiratory Syncytial Virus Involves Protein Kinase C, Underphysphorylated IkappaB-beta, and Sequestration of Protein Phosphatase 2A by the Viral Phosphoprotein", Journal of Virology, vol. 72, No. 7, Jul. 1998, pp. 5610-5618 (9 pages).
Blaese et al., "T Lymphocyte-Directed Gene Therapy for ADA-SCID: Initial Trial Results After 4 Years", Science, vol. 270, Oct. 20, 1995, pp. 475-480 (6 pages).
Blaese et al., "Vectors in cancer therapy: how will they deliver?" Cancer Gene Therapy, vol. 2, No. 4, 1995, pp. 291-297 (7 pages).
Boch et al., "Breaking the Code of DNA Binding Specificity of TAL-Type III Effectors", SCIENCE, vol. 326, Dec. 11, 2009, pp. 1509-1512 (5 pages).
Boissel et al., "megaTALs" a rare-cleaving nuclease architecture for therapeutic genome engineering, Nucleic Acids Research, vol. 42, No. 4, 2014, pp. 2591-2601, doi: 10.1093/nar/gkt1224 (11 pages).
Bonas et al., "Genetic and structural characterization of the avirulence gene avrBs3 from Xanthomonas campestris pv. vesicatoria", Molecular General Genetics MGG, vol. 218, 1989, pp. 127-136 (10 pages).
Brouns et al., "Small CRISPR RNAs Guide Antiviral Defense in Prokaryotes", Science, vol. 321, Aug. 15, 2008, pp. 960-964 (6 pages).
Buchscher et al., "Human Immunodeficiency Virus Vectors for Inducible Expression of Foreign Genes", Journal of Virology, vol. 66, No. 5, May 1992, pp. 2731-2739 (9 pages).
Burstein, et al., "New CRISPR-CAS systems from uncultivated microbes," Nature 542(7640):237-241 (2017).
Carter, et al., "Characterization of progressive motor deficits in mice transgenic for the human Huntington's disease mutation," J Neurosci. 19(8):3248-3257 (1999).
Cebrian-Serrano, et al., "CRISPR-CAS orthologues and variants: optimizing the repertoire, specificity and delivery of genome engineering tools," Mamm Genome 28(7):247-261 (2017).
Chern et al., "The Regulator of MAT2 (ROM2) Protein Binds to Early Maturation Promoters and Represses PvALF-Activated Transcription", The Plant Cell, vol. 8, Feb. 1996, pp. 305-321 (17 pages).
Chevalier et al., "Design, Activity, and Structure of a Highly Specific Artificial Endonuclease", Molecular Cell, vol. 10, Oct. 2002, pp. 895-905 (11 pages).
Cho et al., "Analysis of the C-terminal region of *Arabidopsis thaliana* APETALA1 as a transcription activation domain", Plant Molecular Biology, vol. 40, 1999, pp. 419-429 (11 pages).
Collingwood et al., Nuclear receptors: coactivators, corepressors and chromatin remodeling in the control of transcription, Journal of Molecular Endocrinology, vol. 23, 1999, pp. 255-275 (21 pages).
Cong et al., "Multiplex Genome Engineering Using CRISPR/Cas Systems", Jan. 3, 2013, Sciencexpress, retrieved from URL: http://www.sciencema.org/content/early/recent, doi:10.1126/science.1231143 (7 pages).
Crook, et al., "Huntington's disease: can mice lead the way to treatment?," Neuron 69(3):423-435 (2011).
Crystal, Ronald G., "Transfer of Genes to Humans: Early Lessons and Obstacles to Success", Science, vol. 270, Oct. 20, 1995, pp. 404-410 (7 pages).
Davies et al., "Polyalanine and polyserine frameshift products in Huntington's disease", Journal of Medical Genetics, vol. 43, 2006, pp. 893-896 (4 pages).
Di Prospero et al., "Therapeutics Development for Triplet Repeat Expansion Diseases", Nature Reviews, Genetics, vol. 6, Oct. 2005, pp. 756-765 (10 pages).
Dillon, Niall, "Regulating gene expression in gene therapy", TIBTECH, vol. 11, May 1993, pp. 167-173 (7 pages).
Doyle et al., Reduced nuclear factor kappaB (p65) expression in rat primary sensory neurons after peripheral nerve injury, Neuroport, vol. 8, No. 13, Sep. 3, 1997, pp. 2937-2942 (6 pages).
Dranoff et al., "A Phase I Study of Vaccination with Autologous, Irradiated Melanoma Cells Engineered to Secrete Human Granulocyte-Macrophage Colony Stimulating Factor", Human Gene Therpay, vol. 7, 1997, pp. 111-123 (13 pages).
Dujon et al., "Mobile introns: definition of terms and recommended nomenclature", Gene, vol. 82, 1989, pp. 115-118 (4 pages).
Dull et al., "A Third-Generation Lentivirus Vector with a Conditional Packaging System", Journal of Virology, vol. 72, No. 11, Nov. 1998, pp. 8463-8471 (9 pages).
Dunbar et al., "Retrovirally Marked CD34-Enriched Peripheral Blood and Bone Marrow Cells Contribute to Long-Term Engraftment After Autologous Transplantation", Blood, vol. 85, No. 11, Jun. 1, 1995, pp. 3048-3057 (10 pages).
Ellem et al., "A case report: Immune responses and clinical course of the first human use of granulocyte/macrophage-colony-stimulating-factor-transduced autologous melanoma cells for immunotherapy", Cancer Immunol. Immunother., vol. 44, 1997, pp. 10-20 (11 pages).
Epinat et al., "A novel engineered meganuclease induces homologous recombination in years and mammalian cells", Nucleic Acids Research, vol. 31, No. 11, 2003, pp. 2952-2962 (11 pages).
Esvelt et al., "Orthogonal Cas9 proteins for RNA-guided gene regulation and editing", Nature Methods, vol. 10, No. 11, Nov. 2013, pp. 1116-1121 (8 pages).
Fagerlund, et al., "The cpf1 CRISPR-CAS protein expands genome-editing tools," Genome Biology 16:251 (2015).
Fields et al., "A novel genetic system to detect protein-protein interactions", Nature, vol. 340, Jul. 20, 1989, pp. 245-246 (2 pages).
Follenzi et al., "Gene transfer by lentiviral vectors is limited by nuclear translocation and rescued by HIV-1 pol sequences", Nature Genetics, vol. 25, Jun. 2000, pp. 217-222 (6 pages).
Fonfara et al., "Phylogeny of Cas9 determines functional exchangeability of dual-RNA and Cas9 among orthologous type II CRISPR-Cas systems", Nucleic Acids Research, vol. 42, No. 4, Nov. 22, 2013, pp. 2377-2590 (14 pages).
Fu et al., "Improving CRISPR-Cas nuclease specificity using truncated guide RNAs", Nat Biotechnol., vol. 32, No. 3, Mar. 2014, pp. 279-284 (18 pages).
Gao et al., "Cationic liposome-mediated gene transfer", Gene Therapy, vol. 2, 1995, pp. 710-722 (13 pages).
Gimble et al., "Substrate Recognition and Induced DNA Distortion by the PI-Scel Endonuclease, an Enzyme Generated by Protein Splicing", J. Mol. Biol., vol. 263, 1996, pp. 163-180 (18 pages).
Godde et al., "The Repetitive DNA Elements Called CRISPRs and Their Associated Genes: Evidence of Horizontal Transfer Among Prokaryotes", J Mol Evol, vol. 62, 2006, pp. 718-729 (12 pages).

(56) References Cited

OTHER PUBLICATIONS

Goff et al., "Identification of functional domains in the maize transcriptional activator C1: comparison of wild-type and dominant inhibitor proteins", Genes & Development, vol. 5, 1991, pp. 298-309 (12 pages).
Gong et al., "A constitutively expressed Myc-like gene involved in anthocyanin, heterologous expression in transgenic plants and transactivation in yeast cells", Plant Mol. Biol., vol. 41, 1999, pp. 33-44 (12 pages).
Graham et al., "Cleavage at the Caspase-6 Site Is Required for Neuronal Dysfunction and Degeneration Due to Mutant Huntingtin", Cell, vol. 125, Jun. 16, 2006, pp. 1179-1191 (13 pages).
Haft et al., "A Guild of 45 CRISPR-Associated (Cas) Protein Families and Multiple CRISPR/Cas Subtypes Exist in Prokaryotic Genomes", PLoS Computational Biology, vol. 1, Issue 6, Article e60, Nov. 2005, pp. 0474-0483 (10 pages).
Hagmann et al., "The VP16 Paradox: Herpes Simplex Virus VP16 Contains a Long-Range Activation Domain but within the Natural Multiprotein Complex Activates Only from Promoter-Proximal Positions", Journal of Virology, vol. 71, No. 8, Aug. 1997, pp. 5952-5962 (11 pages).
Hale et al., "Prokaryotic silencing (psi)RNAs in Pyrococcus furiosus", RNA, vol. 14, Oct. 29, 2008, pp. 2572-2579 (9 pages).
Han et al., "Ligand-directed retroviral targeting of human breast cancer cells", Proceedings of the National Academy of Sciences USA, vol. 92, Oct. 1995, pp. 9747-9751 (5 pages).
Hermonat et al., "Use of adeno-associated virus as a mammalian DNA cloning vector: Transduction of neomycin resistance into mammalian tissue culture cells", Proceedings of the National Academy of Sciences, vol. 81, Oct. 1984, pp. 6466-6470 (5 pages).
Heuer et al., "Repeat Domain Diversity of avrBs3-Like Genes in Ralstonia solanacearum Strains and Association with Host Preferences in the Field", Applied and Environmental Microbiology, vol. 73, No. 13, Jul. 2007, pp. 4379-4384, doi:10.1038/mtm.2015.51 (6 pages).
Hobo et al., "A bZIP factor, TRAB1, interacts with VP1 and mediates abscisic acid-induced transcription", Proceedings of the National Academy of Sciences USA, vol. 96, No. 26, Dec. 21, 1999, p. 15348-15353 (6 pages).
Hsu et al., "Development and applications of CRISPR-Cas9 for genome engineering," Cell 157(6):1262-78 (2014).
Hsu et al., "DNA targeting specificity of RNA-guided Cas9 nucleases", Nature Biotechnology, vol. 31, No. 9, Sep. 2013, pp. 827-832, doi:10.1038/nbt.2647 (17 pages).
Huntington Study Group, "Unified Huntington's Disease Rating Scale Reliability and Consistency", Movement Disorders, vol. 11, No. 2, 1996, pp. 136-142 (7 pages).
Hwang et al., "Efficient In Vivo Genome Editing Using RNA-Guided Nucleases", Nat Biotechnol., vol. 31, No. 3, Mar. 2013, pp. 227-229 (12 pages).
Inaba et al., "Generation of Large Numbers of Dendritic Cells from Mouse Bone Marrow Cultures Supplemented with Granulocyte/Macrophage Colony-stimulating Factor", J. Exp. Med., vol. 176, Dec. 1992, pp. 1693-1702 (10 pages).
International Search Report and Written Opinion mailed in PCT/US2020/013661 on Apr. 2, 2020 (10 pgs).
Jansen et al., "Identification of genes that are associated with DNA repeats in prokaryotes", Molecular Microbiology, vol. 43, No. 6, 2002, pp. 1565-1575 (11 pages).
Jasin, Maria, "Genetic manipulation of genomes with rare-cutting endonucleases", Trends in Genetics (TIG), vol. 12, No. 6, Jun. 1996, pp. 224-228 (5 pages).
Jinek et al., "A Programmable Dual-RNA-Guided DNA Endonuclease in Adaptive Bacterial Immunity", Science, vol. 337, Aug. 17, 2012, p. 816-821 (7 pages).
Johann et al., "GLVR1, a Receptor for Gibbon Ape Leukemia Virus, Is Homologous to a Phosphate Permease of Neurospora crassa and Is Expressed at High Levels in the Brain and Thymus", Journal of Virology, vol. 66, No. 3, Mar. 1992, pp. 1635-1640 (6 pages).
Kay et al., "A Bacterial Effector Acts as a Plant Transcription Factor and Induces a Cell Size Regulator", Science, vol. 318, Oct. 26, 2007, pp. 648-651 (5 pages).
Kearns et al., "Recombinant adeno-associated virus (AAV-CFTR) vectors do not integrate in a site-specific fasion in an immortalized epithelial cell line", Gene Ther., vol. 3, 1996, pp. 748-755 (8 pages).
Kells et al., "AAV-Mediated Gene Delivery of BDNF or GDNF Is Neuroprotective in a Model of Huntington Disease", Molecular Therapy, vol. 9, No. 5, May 2004, pp. 682-688 (7 pages).
Kleinstiver, et al., "High-fidelity crispr-cas9 variants with undetectable genome-wide off-targets," Nature 529(7587):490-495, doi:10.1038/nature16526 (2016).
Knoepfler et al., "Sin Meets NuRD and Other Tails of Repression", Cell, vol. 99, Nov. 24, 1999, pp. 447-450 (4 pages).
Kohn et al., "Engraftment of gene-modified umbilical cord blood cells in neonates with adenosine deaminase deficiency", Nature Medicine, vol. 1, No. 10, Oct. 1995, pp. 1017-1023 (7 pages).
Kormann et al., "Expression of therapeutic proteins after delivery of chemically modified mRNA in mice", Nature Biotechnology, vol. 29, No. 2, Feb. 2011, pp. 154-157 (6 pages).
Kotin, Robert M., "Prospects for the Use of Adeno-Associated Virus as a Vector for Human Gene Therapy", Human Gene Therapy, vol. 5, 1994, pp. 793-801 (9 pages).
Kremer et al., "Adenovirus and adeno-associated virus mediated gene transfer", British Medical Bulletin, vol. 51, No. 1, 1995, pp. 31-44 (8 pages).
Lemon et al., "Nuclear receptor cofactors as chromatin remodelers", Current Opinion in Genetics & Development, vol. 9, 1999, pp. 499-504 (6 pages).
Leo et al., "The SRC family of nuclear receptor coactivators", Gene, vol. 245, 2000, pp. 1-11 (11 pages).
Lillestol et al., "A putative viral defence mechanism in archaeal cells", Archaea, vol. 2, Jul. 10, 2006, pp. 59-72 (14 pages).
Liu et al., "Suppression of growth and transformation and induction of apoptosis by EGR-1", Cancer Gene Therapy, vol. 5, No. 1, 1998, pp. 3-28 (26 pages).
Ma, et al., "Rational design of mini-cas9 for transcriptional activation," ACS Synth Biol 7(4):978-985 (2018).
Macdiarmid et al., "Sequential treatment of drug-resistant tumors with targeted minicells containing siRNA or a cytotoxic drug", Nature Biotechnology, vol. 27, No. 7, Jul. 2009, pp. 643-651 (12 pages).
Makarova et al., "A DNA repair system specific for thermophilic Archaea and bacteria predicted by genomic context analysis", Nucleic Acids Research, vol. 30, No. 2, 2002, pp. 482-496 (15 pages).
Makarova et al., "A putative RNA-interference-based immune system in prokaryotes: computational analysis of the predicted enzymatic machinery, functional analogies with eukaryotic RNAi, and hypothetical mechanisms of action", Biology Direct, vol. 1, No. 7, Mar. 16, 2006, pp. 1-26 (26 pages).
Malech et al., "Prolonged production of NADPH oxidase-corrected granulocytes after gene therapy of chronic granulomatous disease", Proceedings of the National Academy of Sciences, vol. 94, Oct. 1997, pp. 12133-12138 (6 pages).
Malik et al., "Transcriptional regulation through Mediator-like coactivators in yeast and metazoan cells", Trends Biochem. Sci. (TIBS), vol. 25, Jun. 2000, pp. 277-283 (7 pages).
Manteuffel-Cymborowska et al., "Nuclear receptors their coactivators and modulation of transcription", Acta Biochimica Polonica, vol. 46,, No. 1, 1999, pp. 77-89 (13 pages).
Mapp et al., "Activation of gene expression by small molecule transcription factors", Proceedings of the National Academy of Sciences USA, vol. 97, No. 8, Apr. 11, 2000, pp. 3930-3935 (6 pages).
McKenna et al., "Nuclear receptor coactivators: multiple enzymes, multiple complexes, multiple functions", Journal of Steroid Biochemistry and Molecular Biology, vol. 69, 1999, pp. 3-12 (10 pages).
Miller et al., "Construction and Properties of Retrovirus Packaging Cells Based on Gibbon Ape Leukemia Virus", Journal of Virology, vol. 65, No. 5, May 1991, pp. 2220-2224 (5 pages).

(56) References Cited

OTHER PUBLICATIONS

Miller, Nature, "Human gene therapy comes of age", vol. 357, Jun. 11, 1992, pp. 455-460 (6 pages).
Mitani et al., "Delivering therapeutic genes—matching approach and application", Trends Biotech. (TIBTECH), vol. 11, May 1993, pp. 162-166 (5 pages).
Molinari et al., "Proteasome-mediated degradation of transcriptional activators correlates with activation domain potency in vivo", The EMBO Journal, vol. 18, No. 22, 1999, pp. 6439-6447 (9 pages).
Moscou et al., "A Simple Cipher Governs DNA Recognition by TAL Effectors", Science, vol. 326, Dec. 11, 2009, pp. 1501 (1 page).
Muzyczka, Nicholas, "Adeno-associated Virus (AAV) Vectors: Will They Work?", J. Clin. Invest., vol. 94, Oct. 1994, pp. 1351 (1 page).
Nabel et al., "Direct gene transfer for immunotherapy and immunization", Trends Biotechnol. (TIBTECH), vol. 11, May 1993, pp. 211-215 (5 pages).
Naldini et al., "Efficient transfer, integration, and sustained long-term expression of the transgene in adult rat brains injected with a lentiviral vector", Proceedings of the National Academy of Sciences USA, vol. 93, Oct. 1996, pp. 11382-11388 (7 pages).
Ogawa et al., "Rice gibberellin-insensitive gene homolog, OsGAI, encodes a nuclear-localized protein capable of gene activation at transcriptional level", Gene, vol. 245, 2000, pp. 21-29 (9 pages).
Okanami et al., "HALF-1, a bZIP-type protein, interacting with the wheat transcription factor HBP-1a contains a novel transcriptional activation domain", Genes to Cells, vol. 1, 1996, pp. 87-99 (13 pages).
Paques et al., "Meganucleases and DNA Double-Strand Break-Induced Recombination: Perspectives for Gene Therapy", Current Gene Therapy, vol. 7, 2007, pp. 49-66 (18 pages).
Perez-Pinera et al., "RNA-guided gene activation by CRISPR-Cas9-based transcription factors", Nature Methods, vol. 10, No. 10, Oct. 2013, pp. 973-976 (12 pages).
Perler et al., "Protein splicing elements: inteins and exteins—a definition of terms and recommended nomenclature", Nucleic Acids Res., vol. 22, No. 7, 1994, pp. 1125-1127 (3 pages).
Piatek et al., "RNA-guided transcriptional regulation in planta via synthetic dCas9-based transcription factors", Plant Biotechnology Journal, vol. 13, 2015, pp. 578-589 (12 pages).
Ramalingam et al., "A CRISPR way to engineer the human genome," Genome Biol. 14(2):107 (2013).
Remacle et al., "New mode of DNA binding of multi-zinc finger transcription factors: deltaEF1 family members bind with two hands to two target sites", The EMBO Journal, vol. 18, No. 18, 1999, pp. 5073-5084 (12 pages).
Remy et al., "Gene Transfer with a Series of Lipophilic DNA-Binding Molecules", Bioconjugate Chem, vol. 5, No. 6, 1994, pp. 647-654 (8 pages).
Robertson et al., "DNMT1 forms a complex with Rb, E2F1 and HDAC1 and represses transcription from E2F-responsive promoters", Nature Genetics, vol. 25, Jul. 2000, pp. 338-342 (5 pages).
Robyr et al., "Nuclear Hormone Receptor Coregulators In Action: Diversity For Shared Tasks", Molecular Endocrinology, vol. 14, No. 3, 2000, pp. 329-347 (19 pages).
Rosenecker et al., "Adenovirus Infection in Cystic Fibrosis Patients: Implications for the Use of Adenoviral Vectors for Gene Transfer", Infection, vol. 24, 1996, pp. 5-8 (4 pages).
Russell et al., "The Phosphodiesterase 10 Positron Emission Tomography Tracer, [18F]MNI-659, as a Novel Biomarker for Early Huntington Disease", JAMA Neurol, vol. 71, No. 12, Oct. 13, 2014, pp. 1520-1528 (9 pages).
Samulski et al., "Helper-Free Stocks of Recombinant Adeno-Associated Viruses: Normal Integration Does Not Require Viral Gene Expression", Journal of Virology, vol. 63, No. 9, Sep. 1989, pp. 3822-3828 (7 pages).
Sander et al., "CRISPR-Cas systems for genome editing, regulation and targeting", Nature Biotechnol., vol. 32, No. 4, Apr. 2014, pp. 347-355 (24 pages).
Schornack et al., "Gene-for-gene-mediated recognition of nuclear-targeted AvrBs3-like bacterial effector proteins", Journal of Plant Physiology, vol. 163, 2006, pp. 256-272 (17 pages).
Seipel et al., "Different activation domains stimulate transcription from remote ('enhancer') and proximal ('promoter') positions", The EMBO Journal, vol. 11, No. 13, 1992, pp. 4961-4968 (8 pages).
Sheng et al., "Structure-based cleavage mechanism of Thermus thermophilus Argonaute DNA guide strand-mediated DNA target cleavage", Proceedings of the National Academy of Sciences USA, vol. 111, No. 2, Jan. 14, 2014, pp. 652-657 (6 pages).
Sommerfelt et al., "Receptor Interference Groups of 20 Retroviruses Plating on Human Cells", Virology, vol. 176, 1990, pp. 58-69 (12 pages).
Sorek et al., "CRISPR—a widespread system that provides acquired resistance against phages in bacteria and archaea", Nature Reviews: Microbiology, vol. 6, Mar. 2008, pp. 181-186 (6 pages).
Sprenger-Haussels et al., "Transactivation properties of parsley proline-rich bZIP transcription factors", The Plant Journal, vol. 22, No. 1, 2000, pp. 1-8 (8 pages).
Sterman et al., "Adenovirus-Mediated Herpes Simplex Virus Thymidine Kinase/Ganciclovir Gene Therapy in Patients with Localized Malignancy: Results of a Phase I Clinical Trial in Malignant Mesothelioma", Human Gene Therapy, vol. 9, May 1, 1998, pp. 1083-1092 (10 pages).
Swarts et al., "DNA-guided DNA interference by a prokaryotic Argonaute", Nature, vol. 507, No. 7491, Mar. 13, 2014, pp. 258-261, doi:10.1038/nature12971 (32 pages).
Tang et al., "Identification of 86 candidates for small non-messenger RNAs from the archaeon Archaeoglobus fulgidus", Proceedings of the National Academy of Sciences USA, vol. 99, No. 11, May 28, 2002, pp. 7536-7541 (6 pages).
Tang et al., "Identification of novel non-coding RNAs as potential antisense regulators in the archaeon Sulfolobus solfataricus", Molecular Microbiology, vol. 55, No. 2, 2005, pp. 469-481, doi: 10.1111/j.1365-2958.2004.04428.x (13 pages).
Topf et al., "Regional 'pro-drug' gene therapy: intravenous administration of an adenoviral vector expressing the *E. coli* cytosine deaminase gene and systemic administration of 5-flourocytosine suppresses growth of hepatic metastasis of colon carcinoma", Gene Therapy, vol. 5, 1998, pp. 507-513 (7 pages).
Torchia et al., "Co-activators and co-repressors in the integration of transcriptional responses", Current Opinion in Cell Biology, vol. 10, 1998, pp. 373-383 (11 pages).
Tratschin et al., "A Human Parvovirus, Adeno-Associated Virus, as a Eurcaryotic Vector: Transient Expression and Encapsidation of the Procaryotic Gene for Chloramphenicol Acetyltransferase", Molecular and Cellular Biology, vol. 4, No. 10, Oct. 1984, pp. 2072-2081 (10 pages).
Tratschin et al., "Adeno-Associated Virus Vector for High-Frequency Integration, Expression, and Rescue of Genes in Mammalian Cells", Molecular and Cellular Biology, vol. 5, No. 11, Nov. 1985, pp. 3251-3260 (10 pages).
Troung, et al., "Development of an intein-mediated split-cas9 system for gene therapy," Nucl Acid Res 43(13):6450-8 (2015).
Tyler et al., "The 'Dark Side' of Chromatin Remodeling: Repressive Effects on Transcription", Cell, vol. 99, Nov. 24, 1999, pp. 443-446 (4 pages).
Ulmasov et al., "Activation and repression of transcription by auxin-response factors", Proceedings of the National Academy of Sciences USA, vol. 96, May 1999, pp. 5844-5849 (6 pages).
Van Brunt, Jennifer, "Molecular Farming: Transgenic Animal as Bioreactors", Biotechnology, vol. 6, No. 10, Oct. 1988, pp. 1149, 1151-1152, 1154 (4 pages).
Vigne et al., "Third-generation adenovectors for gene therapy", Restorative Neurology and Neuroscience, vol. 8, 1995, pp. 35-36 (2 pages).
Wagner et al., "Efficient and persistent gene transfer of AAV-CFTR in maxillary sinus", The Lancet, vol. 351, Jun. 6, 1998, pp. 1702-1703 (2 pages).
Walker, Francis O, "Huntington's Disease", Lancet, vol. 369, Jan. 20, 2007, pp. 218-228 (11 pages).
Welsh et al., "Adenovirus-Mediated Gene Transfer for Cystic Fibrosis: Part A. Safety of Dose and Repeat Administration in the Nasal

(56) References Cited

OTHER PUBLICATIONS

Epithelium, Part B. Clinical Efficacy in the Maxillary Sinus", Human Gene Therapy, vol. 6, Feb. 1995, pp. 205-218 (14 pages).
West et al., "Gene Expression in Adeno-Associated Virus Vectors: The Effects of Chimeric mRNA Structure, Helper Virus, and Adenovirus VA RNA", Virology, vol. 160, 1987, pp. 38-47 (10 pages).
Wild et al., "Quantifying Mutant Huntingtin in Huntington's Disease CSF", J Neurol Neurosurg Psychiatry, ABN Abstracts, vol. 85, No. 10, 2014, pp. e4 (3 pages).
Wilson et al., "Formation of Infectious Hybrid Virions with Gibbon Ape Leukemia Virus and Human T-Cell Leukemia Virus Retroviral Envelope Glycoproteins and the gag and pol Proteins of Moloney Murine Leukemia Virus", Journal of Virology, vol. 63, No. 5, May 1989, pp. 2374-2378 (5 pages).
Wu et al., "Functional analysis of HD2 histone deacetylase homologues in *Arabidopsis thaliana*", The Plant Journal, vol. 22, No. 1, 2000, pp. 19-27 (9 pages).
Wu et al., "Genome-wide binding of the CRISPR endonuclease Cas9 in mammalian cells", Nature Biotechnology, Apr. 20, 2014, pp. 1-7, doi:10.1038/nbt.2889 (9 pages).
Yu et al., "An engineered VEGF-activating zinc finger protein transcription factor improves blood flow and limb salvage in advanced-age mice", The FASEB Journal, vol. 20, Jan. 19, 2006, pp. 479-481, doi:10.1096/rj.04-3670fje (13 pages).
Yu et al., "Progress towards gene therapy for HIV infection", Gene Therapy, vol. 1, 1994, pp. 13-26 (14 pages).
Zetsche, et al., "A split-cas9 architecture for inducible genome editing and transcription modulation," Nat Biotechnol 33(2):139-142 (2015).
Zuccato et al., "Progressive loss of BDNF in a mouse model of Huntington's disease and rescue by BDNF delivery", Pharmacological Research, vol. 52, 2005, pp. 133-139, doi:10.1016/j.phrs.2005.01.001 (7 pages).
Zufferey et al., "Self-Inactivating Lentivirus Vector for Safe and Efficient In Vivo Gene Delivery", Journal of Virology, vol. 72, No. 12, Dec. 1998, pp. 9873-9880 (8 pages).

* cited by examiner

SEQUENCE LISTING

```
<160> NUMBER OF SEQ ID NOS: 23

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 1

Gln Ser Gly Asp Leu Thr Arg
1 5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2

Lys His Gly Asn Leu Ser Glu
1 5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 3

Lys Arg Cys Asn Leu Arg Cys
1 5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 4

Cys Pro Ser His Leu Thr Arg
1 5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 5

Arg Gln Phe Asn Arg His Gln
1 5

<210> SEQ ID NO 6
<211> LENGTH: 28
<212> TYPE: DNA
<213> ORGANISM: Unknown
<220> FEATURE:
<223> OTHER INFORMATION: Description of Unknown:
Human or mouse HTT sequence

<400> SEQUENCE: 6
agcagcagca gcagcagcag cagcagca 28

<210> SEQ ID NO 7
<211> LENGTH: 7

<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Ser Pro Glu Gln Leu Ser Arg
1 5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Gln Trp Ser Thr Arg Lys Arg
1 5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Lys Gln Gly Asn Leu Val Glu
1 5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Arg Ser Asp Asn Leu Ser Glu
1 5

<210> SEQ ID NO 11
<211> LENGTH: 28
<212> TYPE: DNA
<213> ORGANISM: Unknown
<220> FEATURE:
<223> OTHER INFORMATION: Description of Unknown: Human or mouse HTT sequence

<400> SEQUENCE: 11
cagcagcagc agcagcagca gcagcagc 28

<210> SEQ ID NO 12
<211> LENGTH: 21
<212> TYPE: DNA
<213> ORGANISM: Unknown
<220> FEATURE:
<223> OTHER INFORMATION: Description of Unknown: Human or mouse HTT sequence

<400> SEQUENCE: 12
cagcagcagc agcagcagca g 21

<210> SEQ ID NO 13
<211> LENGTH: 825
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 13
atggccccca agaaaaagcg gaaagtgggc atccacgggg tacccgccgc tatggctgag 60
aggcccttcc agtgtcgaat ctgcatgcgt aagtttgccc agtccggcga cctgacccgc 120
cataccaaga tacacacggg cgagaagccc ttccagtgtc gaatctgcat gcgtaacttc 180
agtcagtccg gcgacctgac ccgccacatc cgcacccaca ccggcgagaa gccttttgcc 240
tgtgacattt gtgggaggaa atttgcccag tccggcgacc tgacccgcca taccaagata 300
cacacgccga acccgcaccg ccgcaccgac ccgtcccaca agcccttcca gtgtcgaatc 360
tgcatgcgta acttcagtaa gcacggcaac ctgtccgagc acatccgcac ccacaccggc 420
gagaagcctt ttgcctgtga catttgtggg aggaaatttg ccaagcgctg taacctgcgc 480
tgtcatacca agatacacct gcgccaaaaa gatgcggccc ggggatccgg catggatgct 540
aagtcactaa ctgcctggtc ccggacactg gtgaccttca aggatgtatt tgtggacttc 600
accagggagg agtggaagct gctggacact gctcagcaga tcgtgtacag aaatgtgatg 660
ctggagaact ataagaacct ggtttccttg ggttatcagc ttactaagcc agatgtgatc 720
ctccggttgg agaagggaga agagccctgg ctggtggaga gagaaattca ccaagagacc 780
catcctgatt cagagactgc atttgaaatc aaatcatcag tttaa 825

<210> SEQ ID NO 14
<211> LENGTH: 827
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 14
atggccccca agaaaaagcg gaaagtgggc atccacgggg tacccgccgc tatggctgag 60
aggcccttcc agtgtcgaat ctgcatgcgt aacttcagtt gtccgtccca cctgacccgc 120
cacatccgca cccacaccgg cgagaagcct tttgcctgtg acatttgtgg gaggaaattt 180
gcccagtccg gcgacctgac ccgccatacc aagatacaca cgcctaatcc tcatcgccgc 240
actgatccca gccataagcc cttccagtgt cgaatctgca tgcgtaactt cagtaagcac 300
ggcaacctgt ccgagcacat ccgcacccac accggcgaga agccttttgc ctgtgacatt 360
tgtgggagga aatttgccaa gcgctgtaac ctgcgctgtc ataccaagat acacacgggc 420
tcccaatccc ccttccagtg tcgaatctgc atgcgtaagt ttgcccgcca gttcaaccgc 480
caccagcata ccaagataca cctgcgccaa aaagatgcgg cccggggatc cggcatggat 540
gctaagtcac taactgcctg gtcccggaca ctggtgacct tcaaggatgt atttgtggac 600
ttcaccaggg aggagtggaa gctgctggac actgctcagc agatcgtgta cagaaatgtg 660
atgctggaga actataagaa cctggtttcc ttgggttatc agcttactaa gccagatgtg 720
atcctccggt tggagaaggg agaagagccc tggctggtgg agagagaaat tcaccaagag 780
acccatcctg attcagagac tgcatttgaa atcaaatcat cagttta 827

<210> SEQ ID NO 15
<211> LENGTH: 800
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 15
atggccccca agaaaaagcg gaaagtgggc atccacgggg tacccgccgc tatggctgag 60
aggcccttcc agtgtcgaat ctgcatgcgt aacttcagtt gtccgtccca cctgacccgc 120
cacatccgca cccacaccgg cgagaagcct tttgcctgtg acatttgtgg gaggaaattt 180
gcccagtccg gcgacctgac ccgccatacc aagatacaca cgggcgagaa gcccttccag 240
tgtcgaatct gcatgcgtaa cttcagttgt ccgtcccacc tgacccgcca catccgcacc 300
cacaccggcg agaagccttt tgcctgtgac atttgtggga ggaaatttgc ccagtccggc 360
gacctgaccc gccataccaa gatacacacg ggatctcaga agcccttcca gtgtcgaatc 420
tgcatgcgta agtttgccca gtccggcgac ctgacccgcc ataccaagat acacctgcgc 480
caaaaagatg cggcccgggg atccggcatg gatgctaagt cactaactgc ctggtcccgg 540
acactggtga ccttcaagga tgtatttgtg gacttcacca gggaggagtg gaagctgctg 600
gacactgctc agcagatcgt gtacagaaat gtgatgctgg agaactataa gaacctggtt 660
tccttgggtt atcagcttac taagccagat gtgatcctcc ggttggagaa gggagaagag 720
ccctggctgg tggagagaga aattcaccaa gagacccatc ctgattcaga gactgcattt 780
gaaatcaaat catcagttta 800

<210> SEQ ID NO 16
<211> LENGTH: 740
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 16
atggccccca agaaaaagcg gaaagtgggc atccacgggg tacccgccgc tatggctgag 60
aggcccttcc agtgtcgaat ctgcatgcgt aacttcagtt ccccggagca gctgtcccgc 120
cacatccgca cccacaccgg cgagaagcct tttgcctgtg acatttgtgg gaggaaattt 180
gcccagtggt ccacccgcaa gcgccatacc aagatacaca cgccgaaccc gcaccgccgc 240
accgacccgt cccacaagcc cttccagtgt cgaatctgca tgcgtaactt cagtaagcag 300
ggcaacctgg tggagcacat ccgcacccac accggcgaga agccttttgc ctgtgacatt 360
tgtgggagga aatttgccaa gcgctgtaac ctgcgctgtc ataccaagat acacctgcgc 420
caaaaagatg cggcccgggg atccggcatg gatgctaagt cactaactgc ctggtcccgg 480
acactggtga ccttcaagga tgtatttgtg gacttcacca gggaggagtg gaagctgctg 540
gacactgctc agcagatcgt gtacagaaat gtgatgctgg agaactataa gaacctggtt 600
tccttgggtt atcagcttac taagccagat gtgatcctcc ggttggagaa gggagaagag 660
ccctggctgg tggagagaga aattcaccaa gagacccatc ctgattcaga gactgcattt 720
gaaatcaaat catcagttta 740

<210> SEQ ID NO 17
<211> LENGTH: 922
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 17
atgcccccaa gaaaaagcgg aaagtgggca tccacggggt acccgccgct atggctgaga 60
ggcccttcca gtgtcgaatc tgcatgcgta acttcagtcg ctccgacaac ctgtccgagc 120
acatccgcac ccacaccggc gagaagcctt ttgcctgtga catttgtggg aggaaatttg 180
ccaagcgctg taacctgcgc tgtcatacca agatacacac gcatcccagg gcacctattc 240
ccaagccctt ccagtgtcga atctgcatgc gtaacttcag tcagtccggc gacctgaccc 300
gccacatccg cacccacacc ggcgagaagc cttttgcctg tgacatttgt gggaggaaat 360
ttgcccagtc cggcgacctg acccgccata ccaagataca cacgccgaac ccgcaccgcc 420
gcaccgaccc gtcccacaag cccttccagt gtcgaatctg catgcgtaac ttcagtcgct 480
ccgacaacct gtccgagcac atccgcaccc acaccggcga gaagcctttt gcctgtgaca 540
tttgtgggag gaaatttgcc aagcgctgta acctgcgctg tcataccaag atacacctgc 600
gccaaaaaga tgcggcccgg ggatccggca tggatgctaa gtcactaact gcctggtccc 660
ggacactggt gaccttcaag gatgtatttg tggacttcac cagggaggag tggaagctgc 720
tggacactgc tcagcagatc gtgtacagaa atgtgatgct ggagaactat aagaacctgg 780
tttccttggg ttatcagctt actaagccag atgtgatcct ccggttggag aagggagaag 840
agccctggct ggtggagaga gaaattcacc aagagaccca tcctgattca gagactgcat 900
ttgaaatcaa atcatcagtt ta 922

<210> SEQ ID NO 18
<211> LENGTH: 274
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 18

Met Ala Pro Lys Lys Lys Arg Lys Val Gly Ile His Gly Val Pro Ala
1 5 10 15

Ala Met Ala Glu Arg Pro Phe Gln Cys Arg Ile Cys Met Arg Lys Phe
20 25 30

Ala Gln Ser Gly Asp Leu Thr Arg His Thr Lys Ile His Thr Gly Glu
35 40 45

Lys Pro Phe Gln Cys Arg Ile Cys Met Arg Asn Phe Ser Gln Ser Gly
50 55 60

Asp Leu Thr Arg His Ile Arg Thr His Thr Gly Glu Lys Pro Phe Ala
65 70 75 80

Cys Asp Ile Cys Gly Arg Lys Phe Ala Gln Ser Gly Asp Leu Thr Arg
85 90 95

His Thr Lys Ile His Thr Pro Asn Pro His Arg Arg Thr Asp Pro Ser
100 105 110

His Lys Pro Phe Gln Cys Arg Ile Cys Met Arg Asn Phe Ser Lys His
115 120 125

Gly Asn Leu Ser Glu His Ile Arg Thr His Thr Gly Glu Lys Pro Phe
130 135 140

Ala Cys Asp Ile Cys Gly Arg Lys Phe Ala Lys Arg Cys Asn Leu Arg
145 150 155 160

```
Cys His Thr Lys Ile His Leu Arg Gln Lys Asp Ala Ala Arg Gly Ser
                165                 170                 175

Gly Met Asp Ala Lys Ser Leu Thr Ala Trp Ser Arg Thr Leu Val Thr
            180                 185                 190

Phe Lys Asp Val Phe Val Asp Phe Thr Arg Glu Glu Trp Lys Leu Leu
        195                 200                 205

Asp Thr Ala Gln Gln Ile Val Tyr Arg Asn Val Met Leu Glu Asn Tyr
    210                 215                 220

Lys Asn Leu Val Ser Leu Gly Tyr Gln Leu Thr Lys Pro Asp Val Ile
225                 230                 235                 240

Leu Arg Leu Glu Lys Gly Glu Glu Pro Trp Leu Val Glu Arg Glu Ile
                245                 250                 255

His Gln Glu Thr His Pro Asp Ser Glu Thr Ala Phe Glu Ile Lys Ser
            260                 265                 270

Ser Val


<210> SEQ ID NO 19
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Ala Pro Lys Lys Lys Arg Lys Val Gly Ile His Gly Val Pro Ala
1               5                   10                  15

Ala Met Ala Glu Arg Pro Phe Gln Cys Arg Ile Cys Met Arg Asn Phe
            20                  25                  30

Ser Cys Pro Ser His Leu Thr Arg His Ile Arg Thr His Thr Gly Glu
        35                  40                  45

Lys Pro Phe Ala Cys Asp Ile Cys Gly Arg Lys Phe Ala Gln Ser Gly
    50                  55                  60

Asp Leu Thr Arg His Thr Lys Ile His Thr Pro Asn Pro His Arg Arg
65                  70                  75                  80

Thr Asp Pro Ser His Lys Pro Phe Gln Cys Arg Ile Cys Met Arg Asn
                85                  90                  95

Phe Ser Lys His Gly Asn Leu Ser Glu His Ile Arg Thr His Thr Gly
            100                 105                 110

Glu Lys Pro Phe Ala Cys Asp Ile Cys Gly Arg Lys Phe Ala Lys Arg
        115                 120                 125

Cys Asn Leu Arg Cys His Thr Lys Ile His Thr Gly Ser Gln Ser Pro
    130                 135                 140

Phe Gln Cys Arg Ile Cys Met Arg Lys Phe Ala Arg Gln Phe Asn Arg
145                 150                 155                 160

His Gln His Thr Lys Ile His Leu Arg Gln Lys Asp Ala Ala Arg Gly
                165                 170                 175

Ser Gly Met Asp Ala Lys Ser Leu Thr Ala Trp Ser Arg Thr Leu Val
            180                 185                 190

Thr Phe Lys Asp Val Phe Val Asp Phe Thr Arg Glu Glu Trp Lys Leu
        195                 200                 205

Leu Asp Thr Ala Gln Gln Ile Val Tyr Arg Asn Val Met Leu Glu Asn
    210                 215                 220

Tyr Lys Asn Leu Val Ser Leu Gly Tyr Gln Leu Thr Lys Pro Asp Val
225                 230                 235                 240
```

```
Ile Leu Arg Leu Glu Lys Gly Glu Glu Pro Trp Leu Val Glu Arg Glu
                245                 250                 255

Ile His Gln Glu Thr His Pro Asp Ser Glu Thr Ala Phe Glu Ile Lys
            260                 265                 270

Ser Ser Val
        275


<210> SEQ ID NO 20
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Ala Pro Lys Lys Lys Arg Lys Val Gly Ile His Gly Val Pro Ala
1               5                   10                  15

Ala Met Ala Glu Arg Pro Phe Gln Cys Arg Ile Cys Met Arg Asn Phe
            20                  25                  30

Ser Cys Pro Ser His Leu Thr Arg His Ile Arg Thr His Thr Gly Glu
        35                  40                  45

Lys Pro Phe Ala Cys Asp Ile Cys Gly Arg Lys Phe Ala Gln Ser Gly
    50                  55                  60

Asp Leu Thr Arg His Thr Lys Ile His Thr Gly Glu Lys Pro Phe Gln
65                  70                  75                  80

Cys Arg Ile Cys Met Arg Asn Phe Ser Cys Pro Ser His Leu Thr Arg
                85                  90                  95

His Ile Arg Thr His Thr Gly Glu Lys Pro Phe Ala Cys Asp Ile Cys
            100                 105                 110

Gly Arg Lys Phe Ala Gln Ser Gly Asp Leu Thr Arg His Thr Lys Ile
        115                 120                 125

His Thr Gly Ser Gln Lys Pro Phe Gln Cys Arg Ile Cys Met Arg Lys
    130                 135                 140

Phe Ala Gln Ser Gly Asp Leu Thr Arg His Thr Lys Ile His Leu Arg
145                 150                 155                 160

Gln Lys Asp Ala Ala Arg Gly Ser Gly Met Asp Ala Lys Ser Leu Thr
                165                 170                 175

Ala Trp Ser Arg Thr Leu Val Thr Phe Lys Asp Val Phe Val Asp Phe
            180                 185                 190

Thr Arg Glu Glu Trp Lys Leu Leu Asp Thr Ala Gln Gln Ile Val Tyr
        195                 200                 205

Arg Asn Val Met Leu Glu Asn Tyr Lys Asn Leu Val Ser Leu Gly Tyr
    210                 215                 220

Gln Leu Thr Lys Pro Asp Val Ile Leu Arg Leu Glu Lys Gly Glu Glu
225                 230                 235                 240

Pro Trp Leu Val Glu Arg Glu Ile His Gln Glu Thr His Pro Asp Ser
                245                 250                 255

Glu Thr Ala Phe Glu Ile Lys Ser Ser Val
            260                 265


<210> SEQ ID NO 21
<211> LENGTH: 246
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 21

```
Met Ala Pro Lys Lys Lys Arg Lys Val Gly Ile His Gly Val Pro Ala
1               5                   10                  15

Ala Met Ala Glu Arg Pro Phe Gln Cys Arg Ile Cys Met Arg Asn Phe
            20                  25                  30

Ser Ser Pro Glu Gln Leu Ser Arg His Ile Arg Thr His Thr Gly Glu
        35                  40                  45

Lys Pro Phe Ala Cys Asp Ile Cys Gly Arg Lys Phe Ala Gln Trp Ser
    50                  55                  60

Thr Arg Lys Arg His Thr Lys Ile His Thr Pro Asn Pro His Arg Arg
65                  70                  75                  80

Thr Asp Pro Ser His Lys Pro Phe Gln Cys Arg Ile Cys Met Arg Asn
                85                  90                  95

Phe Ser Lys Gln Gly Asn Leu Val Glu His Ile Arg Thr His Thr Gly
            100                 105                 110

Glu Lys Pro Phe Ala Cys Asp Ile Cys Gly Arg Lys Phe Ala Lys Arg
        115                 120                 125

Cys Asn Leu Arg Cys His Thr Lys Ile His Leu Arg Gln Lys Asp Ala
    130                 135                 140

Ala Arg Gly Ser Gly Met Asp Ala Lys Ser Leu Thr Ala Trp Ser Arg
145                 150                 155                 160

Thr Leu Val Thr Phe Lys Asp Val Phe Val Asp Phe Thr Arg Glu Glu
                165                 170                 175

Trp Lys Leu Leu Asp Thr Ala Gln Gln Ile Val Tyr Arg Asn Val Met
            180                 185                 190

Leu Glu Asn Tyr Lys Asn Leu Val Ser Leu Gly Tyr Gln Leu Thr Lys
        195                 200                 205

Pro Asp Val Ile Leu Arg Leu Glu Lys Gly Glu Glu Pro Trp Leu Val
    210                 215                 220

Glu Arg Glu Ile His Gln Glu Thr His Pro Asp Ser Glu Thr Ala Phe
225                 230                 235                 240

Glu Ile Lys Ser Ser Val
                245
```

<210> SEQ ID NO 22
<211> LENGTH: 307
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Met Ala Pro Lys Lys Lys Arg Lys Val Gly Ile His Gly Val Pro Ala
1               5                   10                  15

Ala Met Ala Glu Arg Pro Phe Gln Cys Arg Ile Cys Met Arg Asn Phe
            20                  25                  30

Ser Arg Ser Asp Asn Leu Ser Glu His Ile Arg Thr His Thr Gly Glu
        35                  40                  45

Lys Pro Phe Ala Cys Asp Ile Cys Gly Arg Lys Phe Ala Lys Arg Cys
    50                  55                  60

Asn Leu Arg Cys His Thr Lys Ile His Thr His Pro Arg Ala Pro Ile
65                  70                  75                  80

Pro Lys Pro Phe Gln Cys Arg Ile Cys Met Arg Asn Phe Ser Gln Ser
```

```
                85                  90                  95

Gly Asp Leu Thr Arg His Ile Arg Thr His Thr Gly Glu Lys Pro Phe
            100                 105                 110

Ala Cys Asp Ile Cys Gly Arg Lys Phe Ala Gln Ser Gly Asp Leu Thr
        115                 120                 125

Arg His Thr Lys Ile His Thr Pro Asn Pro His Arg Arg Thr Asp Pro
    130                 135                 140

Ser His Lys Pro Phe Gln Cys Arg Ile Cys Met Arg Asn Phe Ser Arg
145                 150                 155                 160

Ser Asp Asn Leu Ser Glu His Ile Arg Thr His Thr Gly Glu Lys Pro
                165                 170                 175

Phe Ala Cys Asp Ile Cys Gly Arg Lys Phe Ala Lys Arg Cys Asn Leu
            180                 185                 190

Arg Cys His Thr Lys Ile His Leu Arg Gln Lys Asp Ala Ala Arg Gly
        195                 200                 205

Ser Gly Met Asp Ala Lys Ser Leu Thr Ala Trp Ser Arg Thr Leu Val
    210                 215                 220

Thr Phe Lys Asp Val Phe Val Asp Phe Thr Arg Glu Glu Trp Lys Leu
225                 230                 235                 240

Leu Asp Thr Ala Gln Gln Ile Val Tyr Arg Asn Val Met Leu Glu Asn
                245                 250                 255

Tyr Lys Asn Leu Val Ser Leu Gly Tyr Gln Leu Thr Lys Pro Asp Val
            260                 265                 270

Ile Leu Arg Leu Glu Lys Gly Glu Glu Pro Trp Leu Val Glu Arg Glu
        275                 280                 285

Ile His Gln Glu Thr His Pro Asp Ser Glu Thr Ala Phe Glu Ile Lys
    290                 295                 300

Ser Ser Val
305


<210> SEQ ID NO 23
<211> LENGTH: 201
<212> TYPE: DNA
<213> ORGANISM: Homo sapiens
<220> FEATURE:
<221> NAME/KEY: misc_feature
<222> LOCATION: (1)..(201)
<223> OTHER INFORMATION: This sequence may encompass 15-67 “cag”
      repeating units
<220> FEATURE:
<223> OTHER INFORMATION: See specification as filed for detailed
      description of substitutions and preferred embodiments

<400> SEQUENCE: 23

cagcagcagc agcagcagca gcagcagcag cagcagcagc agcagcagca gcagcagcag     60

cagcagcagc agcagcagca gcagcagcag cagcagcagc agcagcagca gcagcagcag    120

cagcagcagc agcagcagca gcagcagcag cagcagcagc agcagcagca gcagcagcag    180

cagcagcagc agcagcagca g                                              201
```

HTT REPRESSORS COMPRISING A ZINC-FINGER PROTEIN TRANSCRIPTION FACTOR

The present application is a 35 U.S.C. § 371 filing of PCT/US2020/013661, filed Jan. 15, 2020 which claims the benefit of U.S. Provisional Applications No. 62/792,701, filed Jan. 15, 2019, the disclosures of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jun. 7, 2021, is named 129068-0171 SL.txt and is 22,205 bytes in size.

TECHNICAL FIELD

The present disclosure is in the field of diagnostics and therapeutics for Huntington's Disease.

BACKGROUND

Huntington's Disease (HD), also known as Huntington's Chorea, is a progressive disorder of motor, cognitive and psychiatric disturbances. The mean age of onset for this disease is age 35-44 years, although in about 10% of cases, onset occurs prior to age 21, and the average lifespan post-diagnosis of the disease is 15-18 years. Prevalence is about 3 to 7 among 100,000 people of western European descent.

Huntington's Disease is an example of a trinucleotide repeat expansion disorder and was first characterized in the early 1990s (see Di Prospero and Fischbeck (2005) *Nature Reviews Genetics* 6:756-765). These disorders involve the localized expansion of unstable repeats of sets of three nucleotides and can result in loss of function of the gene in which the expanded repeat resides, a gain of toxic function, or both. Trinucleotide repeats can be located in any part of the gene, including non-coding and coding gene regions. Repeats located within the coding regions typically involve either a repeated glutamine encoding triplet (CAG) or an alanine encoding triplet (CGA). Expanded repeat regions within non-coding sequences can lead to aberrant expression of the gene while expanded repeats within coding regions (also known as codon reiteration disorders) may cause mis-folding and protein aggregation. The exact cause of the pathophysiology associated with the aberrant proteins is often not known. Typically, in the wild-type genes that are subject to trinucleotide expansion, these regions contain a variable number of repeat sequences in the normal population, but in the afflicted populations, the number of repeats can increase from a doubling to a log order increase in the number of repeats. In HD, repeats are inserted within the N terminal coding region of the gene encoding the large cytosolic protein Huntingtin (HTT). Normal HTT alleles contain 15-24 CAG repeats ("CAG" repeats disclosed as SEQ ID NO: 23), while alleles containing 36 or more repeats can be considered potentially HD causing alleles and confer risk for developing the disease. Alleles containing 36-39 repeats are considered incompletely penetrant, and those individuals harboring those alleles may or may not develop the disease (or may develop symptoms later in life) while alleles containing 40 repeats or more are considered completely penetrant. In fact, no persons containing HD alleles with this many repeats have been reported to be asymptomatic. Those individuals with juvenile onset HD (<21 years of age) are often found to have 60 or more CAG repeats. In addition to an increase in CAG repeats, it has also been shown that HD can involve +1 and +2 frameshifts within the repeat sequences such that the region will encode a poly-serine polypeptide (encoded by AGC repeats in the case of a +1 frameshift) track rather than poly-glutamine (Davies and Rubinsztein (2006) *Journal of Medical Genetics* 43:893-896). In HD, the mutant HTT (mHTT) allele is usually inherited from one parent as a dominant trait. Any child born of a HD patient has a 50% chance of developing the disease if the other parent was not afflicted with the disorder. In some cases, a parent may have an intermediate HD allele and be asymptomatic while, due to repeat expansion, the child manifests the disease. In addition, the HD allele can also display a phenomenon known as anticipation wherein increasing severity or decreasing age of onset is observed over several generations due to the unstable nature of the repeat region during spermatogenesis.

Furthermore, trinucleotide expansion in HTT leads to neuronal loss in the medium spiny gamma-aminobutyric acid (GABA) projection neurons in the striatum, with neuronal loss also occurring in the neocortex. Medium spiny neurons that contain enkephalin and that project to the external globus pallidum are more involved than neurons that contain substance P and project to the internal globus pallidum. Other brain areas greatly affected in people with Huntington's disease include the substantia nigra, cortical layers 3, 5, and 6, the CAI region of the hippocampus, the angular gyrus in the parietal lobe, Purkinje cells of the cerebellum, lateral tuberal nuclei of the hypothalamus, and the centromedialparafascicular complex of the thalamus (Walker (2007) *Lancet* 369:218-228).

The role of the normal HTT protein is poorly understood, but it may be involved in neurogenesis, apoptotic cell death, and vesicle trafficking. In addition, there is evidence that wild-type HTT stimulates the production of brain-derived neurotrophic factor (BDNF), a pro-survival factor for the striatal neurons. It has been shown that progression of HD correlates with a decrease in BDNF expression in mouse models of HD (Zuccato et al. (2005) *Pharmacological Research* 52(2):133-139), and that delivery of either BDNF or glial cell line-derived neurotrophic factor (GDNF) via recombinant adeno-associated viral (rAAV) vector-mediated gene delivery may protect straital neurons in mouse models of HD (Kells et al. (2004) *Molecular Therapy* 9(5):682-688).

Diagnostic and treatment options for HD are currently very limited. In terms of diagnostics, altered (mutant) HTT (mHITT) levels are significantly associated with disease burden score, and soluble mHTT species increase in concentration with disease progression. However, low-abundance mHTT is difficult to quantify in the patient CNS, which limits both study of the role in the neuropathobiology of HD in vivo, and precludes the demonstration of target engagement by HTT-lowering drugs. See, e.g., Wild et al. (2014) *J Neurol Neurosurg Psychiatry* 85:e4.

With regard to treatment, some potential methodologies designed to prevent the toxicities associated with protein aggregation that occurs through the extended poly-glutamine tract such as overexpression of chaperonins or induction of the heat shock response with the compound geldanamycin have shown a reduction in these toxicities in in vitro models. Other treatments target the role of apoptosis in the clinical manifestations of the disease. For example, slowing of disease symptoms has been shown via blockage of caspase activity in animal models in the offspring of a pairing of mice where one parent contained a HD allele and the other parent had a dominant negative allele for caspase 1. Additionally, cleavage of mHTT by caspase may play a role in the pathogenicity of the disease. Transgenic mice carrying caspase-6 resistant mutant HTT were found to maintain normal neuronal function and did not develop striatal neurodegeneration as compared to mice carrying a non-caspase resistant mutant HTT allele (see Graham et al. (2006) *Cell* 125:1179-1191). Molecules which target members of the apoptotic pathway have also been shown to have a slowing effect on symptomology. For example, the compounds zVAD-fmk and minocycline, both of which inhibit caspase activity, have been shown to slow disease manifestation in mice. The drug remacemide has also been used in small HD human trials because the compound was thought to prevent the binding of the mutant HTT to the NDMA receptor to prevent the exertion of toxic effects on the nerve cell. However, no statistically significant improvements were observed in neuron function in these trials. In addition, the Huntington Study Group conducted a randomized, double-blind study using Co-enzyme Q. Although a trend towards slower disease progression among patients that were treated with coenzyme Q10 was observed, there was no significant change in the rate of decline of total functional capacity. (Di Prospero and Fischbeck (2005) *Nature Reviews Genetics* 6:756-765).

Recombinant transcription factors and nucleases comprising the DNA binding domains from zinc finger proteins ("ZFPs"), TAL-effector domains ("TALEs") and CRISPR/Cas transcription factor systems (including Cas and/or Cfp1 systems) have the ability to regulate gene expression of endogenous genes. See, e.g., U.S. Pat. Nos. 9,045,763; 9,005,973; 8,956,828; 8,945,868; 8,586,526; 6,534,261; 6,599,692; 6,503,717; 6,689,558; 7,067,317; 7,262,054; 7,888, 121; 7,972,854; 7,914,796; 7,951,925; 8,110,379; 8,409,861; U.S. Patent Publication Nos. 2003/0232410; 2005/0208489; 2005/0026157; 2005/0064474; 2006/0063231; 2008/0159996; 2010/00218264; 2012/0017290; 2011/0265198; 2013/0137104; 2013/0122591; 2013/0177983, 2013/0177960, 2015/0335708; and 2015/0056705; Perez-Pinera et al. (2013) *Nature Methods* 10:973-976; Piatek et al. (2015) *Plant Biotechnology J.* 13(4):578-89, doi:10.1111/pbi.12284), the disclosures of which are incorporated by reference in their entireties for all purposes. For instance, U.S. Pat. Nos. 9,234,016; 9,943,565; 8,841,260; 9,499,597; and U.S. Patent Publication Nos. 2018/0200332; 2017/0096460; 2017/0035839; 2016/0296605 and 2019/0322711 relate to DNA-binding proteins that modulate expression of an HD allele such as HTT. U.S. Patent Publication No. 2015/0335708 relates to methods of modifying medium spiny neurons.

Further, targeted nucleases are being developed based on the Argonaute system (e.g., from *T. thermophilus*, known as 'TtAgo', see Swarts et al. (2014) *Nature* 507(7491):258-261), which also may have the potential for uses in genome editing and gene therapy. Clinical trials using these engineered transcription factors containing zinc finger proteins have shown that these novel transcription factors are capable of treating various conditions. (see, e.g., Yu et al. (2006) *FASEB J.* 20:479-481). Nuclease-mediated cleavage involves the use of engineered nucleases to induce a double strand break (DSB) or a nick in a target DNA sequence such that repair of the break by an error born process such as non-homologous end joining (NHEJ) or repair using a repair template (homology directed repair or HDR) can result in the knock out of a gene or the insertion of a sequence of interest (targeted integration). Introduction of a double strand break in the absence of an externally supplied repair template (e.g. "donor" or "transgene") is commonly used for the inactivation of the targeted gene via mutations (insertions and/or deletions known as "indels") introduced by the cellular NHEJ pathway.

However, there remains a need for methods for the diagnosis, study, treatment and/or prevention of Huntington's Disease, including for modalities that exhibit widespread delivery to the brain.

SUMMARY

Disclosed herein are methods and compositions for diagnosing, preventing and/or treating Huntington's Disease. In particular, provided herein are methods and compositions for modifying (e.g., modulating expression of) an HD HTT allele so as to prevent or treat Huntington Disease, including mHTT repressors (that repress mHTT transcripts and thus also repress mHTT protein expression). The compositions (mHTT repressors) described herein provide a therapeutic benefit in subjects, for example by reducing cell death, decreasing apoptosis, increasing cellular function (metabolism) and/or reducing motor deficiency in the subjects. Thus, described herein are non-naturally occurring zinc finger proteins (ZFPs) that bind to the CAG repeats domain of mHTT gene, the zinc finger protein comprising 4, 5 or 6 zinc finger domains ordered F1 to F4, F1 to F5 of F1 to F6 as described herein, including ZFPs comprising the recognition helix regions of the ZFPs designated 45643, 46025, 45294, 45723 or 33074. In certain embodiments, provided herein is a ZFP designated 45294 or 45723, comprising the recognition helix regions in the order shown in a single row of Table 1. Also described are artificial transcription factors (ZFP-TFs) comprising these ZFPs operably linked to a transcriptional repression domain (e.g., KRAB, KOX, etc.) and optionally comprising additional elements such as a nuclear localization signal (NLS) and/or a promoter (e.g., a constitutive promoter such as the CMV promoter) driving expression of the ZFP-TF-encoding sequence (e.g., a ZFP-TF comprising the ZFP designated 45294 or 45723 further comprising a sequence encoding a transcriptional repression domain and optionally comprising a sequence encoding an NLS and/or a promoter driving expression of the ZFP-TF). In certain embodiments, provided herein are one or more ZFP-TFs (in protein and/or polynucleotide form) having the amino acid sequence or nucleotide sequence as shown in a single row of Table 3 (a particular repressor).

Described herein is a zinc finger protein transcription factor (ZFP-TF) comprising a zinc finger protein (ZFP) designated 45294 or 45723 or comprising the amino acid sequence of a ZFP-TF as shown in Table 3. Also described are one or more polynucleotides encoding one or more ZFP-TFs as described herein, in which the one or more polynucleotides may encode one or more of the same and/or different ZFP-TFs, optionally wherein the one or more polynucleotides comprise one or more rAAV vectors (e.g., an rAAV comprising a sequence encoding one or more ZFP-TFs comprising the ZFP designated 45294 or 45723 or wherein the rAAV vector comprises a polynucleotide having the sequence shown in Table 3, optionally wherein one or more rAAV vectors further comprise additional elements such as a sequence encoding a nuclear localization signal (NLS) and, optionally, a promoter driving expression of the ZFP-TF, such as a constitutive promoter (e.g., CMV). Also described herein is a pharmaceutical composition comprising one or more ZFP-TFs, one or more polynucleotides and/or one or more rAAV vectors as described herein. Methods of modifying expression of an HTT gene (e.g., a mutant HTT (mHTT) gene) in a cell (e.g., a neuronal cell in the brain, optionally in the striatum) or subject are also provided, the method comprising administering to the cell one or more ZFP-TFs, one or more polynucleotides, one or more rAAV vectors and/or a pharmaceutical composition as described herein to the cell of subject. Methods of treating and/or preventing Huntington's Disease (HD) in a subject in need thereof are also provided, the method comprising administering one or more ZFP-TFs, one or more polynucleotides, one or more rAAV vectors and/or a pharmaceutical composition according as described herein to the subject in need thereof, optionally wherein the one or more ZFP-TFs, polynucleotides, rAAV vectors and/or pharmaceutical compositions are administered bilaterally to the striatum of the subject. Also provided is use of one or more ZFP-TFs, one or more polynucleotides, one or more rAAV vectors and/or a pharmaceutical composition as described herein for repression of mutant HTT (mHITT) expression in a subject in need thereof. Treatment and/or prevention of HD may involve reduction of mHTT aggregates and/or motor deficiencies in the subject. Furthermore, in any of the method or uses described herein the one or more ZFP-TFs, one or more polynucleotides, one or more rAAV vectors and/or pharmaceutical composition may be delivered to the brain of the subject, optionally bilaterally to the striatum of the subject at any dosages, including but not limited to at a dose of between $1\times10^7$ and $1\times10^{15}$ (or any value therebetween) vector genomes (vg) per striatum.

Thus, in one aspect, engineered (non-naturally occurring) mHTT repressors are provided. The repressors may comprise systems (e.g., zinc finger proteins, TAL effector (TALE) proteins or CRISPR/dCas-TF) that modulate expression of a HD allele (e.g., mHTT). Engineered zinc finger proteins or TALEs are non-naturally occurring zinc finger or TALE proteins whose DNA binding domains (e.g., recognition helices or RVDs) have been altered (e.g., by selection and/or rational design) to bind to a pre-selected target site. Any of the zinc finger proteins described herein may include 1, 2, 3, 4, 5, 6 or more zinc fingers, each zinc finger having a recognition helix that binds to a target subsite in the selected sequence(s) (e.g., gene(s)). Similarly, any of the TALE proteins described herein may include any number of TALE RVDs. In some embodiments, at least one RVD has non-specific DNA binding. In some embodiments, at least one recognition helix (or RVD) is non-naturally occurring. In certain embodiments, the repressor comprises a DNA-binding domain (ZFP, TALE, single guide RNA) operably linked to a transcriptional repression domain to create an artificial transcription factor (repressor). Optionally, the artificial repressor comprises additional components, including but not limited to a nuclear localization signal (NLS). In some embodiments these artificial TFs (e.g., ZFP-TFs, CRISPR/dCas-TFs or TALE-TFs) include protein interaction domains (or "dimerization domains") that allow multimerization when bound to DNA.

In certain embodiments, the zinc finger proteins (ZFPs), Cas proteins of a CRISPR/Cas system or TALE proteins as described herein can be placed in operative linkage with a regulatory domain (or functional domain) as part of a fusion protein. The functional domain can be, for example, a transcriptional activation domain, a transcriptional repression domain and/or a nuclease (cleavage) domain. By selecting either an activation domain or repression domain for use with the DNA-binding domain, such molecules can be used either to activate or to repress gene expression. In some embodiments, a molecule comprising a ZFP, dCas or TALE targeted to a mHITT as described herein fused to a transcriptional repression domain that can be used to down-regulate mutant HTT expression is provided. In some embodiments, a fusion protein comprising a ZFP, CRISPR/Cas or TALE targeted to a wild-type HTT allele fused to a transcription activation domain that can up-regulate the wild type HTT allele is provided. In certain embodiments, the activity of the regulatory domain is regulated by an exogenous small molecule or ligand such that interaction with the cell's transcription machinery will not take place in the absence of the exogenous ligand, while in other embodiments, the exogenous small molecule or ligand prevents the interaction. Such external ligands control the degree of interaction of the ZFP-TF, CRISPR/Cas-TF or TALE-TF with the transcription machinery. The regulatory domain(s) may be operatively linked to any portion(s) of one or more of the ZFPs. dCas or TALEs, including between one or more ZFPs, dCas or TALEs, exterior to one or more ZFPs, dCas or TALEs and any combination thereof. Any of the fusion proteins described herein may be formulated into a pharmaceutical composition.

In some embodiments, the engineered DNA binding domains as described herein can be placed in operative linkage with nuclease (cleavage) domains as part of a fusion protein. In some embodiments, the nuclease comprises a Ttago nuclease. In other embodiments, nuclease systems such as the CRISPR/Cas system may be utilized with a specific single guide RNA to target the nuclease to a target location in the DNA. In certain embodiments, such nucleases and nuclease fusions may be utilized for targeting mutant HTT alleles in stem cells such as induced pluripotent stem cells (iPSC), human embryonic stem cells (hESC), mesenchymal stem cells (MSC) or neuronal stem cells wherein the activity of the nuclease fusion will result in an HTT allele containing a wild type number of CAG repeats. Thus, any of the HTT (e.g., mHTT) repressors described herein can further comprise a dimerization domain and/or a functional domain (e.g., transcriptional activation domain, a transcriptional repression domain or a nuclease domain). In certain embodiments, pharmaceutical compositions comprising the modified cells (e.g., stem cells) are provided. In certain embodiments, the repressor comprises a ZFP comprising the recognition helix regions in the order as shown in a single row of Table 1. ZFP-TFs (repressors) as shown in Table 3 (one repressor per row as labeled in Table 3) are also provided. Compositions comprising one or more of the fusion molecules (e.g., ZFP-TFs comprising the ZFPs of Table 1 and/or ZFP-TFs as shown in Table 3) are also provided In yet another aspect, a polynucleotide encoding one or more of the DNA binding proteins and/or fusion molecules (e.g., artificial transcription factors) as described herein is provided. In certain embodiments, the polynucleotide is carried on a viral (e.g., AAV or Ad) vector and/or a non-viral (e.g., plasmid or mRNA vector or aptamer). Host cells comprising these polynucleotides (e.g., rAAV vectors) and/or pharmaceutical compositions comprising the polynucleotides, proteins and/or host cells as described herein are also provided. In certain embodiments, the polynucleotide comprises at least one sequence as shown in Table 3 (column 2). Compositions comprising one or more of these polynucleotides are also provided.

In other aspects, the invention comprises delivery of a donor nucleic acid to a target cell. The donor may be delivered prior to, after, or along with the nucleic acid encoding the nuclease(s). The donor nucleic acid may comprise an exogenous sequence (transgene) to be integrated into the genome of the cell, for example, an endogenous locus. In some embodiments, the donor may comprise a full-length gene or fragment thereof flanked by regions of homology with the targeted cleavage site. In some embodiments, the donor lacks homologous regions and is integrated into a target locus through homology independent mechanism (i.e. NHEJ). The donor may comprise any nucleic acid sequence, for example a nucleic acid that, when used as a substrate for homology-directed repair of the nuclease-induced double-strand break, leads to a donor-specified deletion to be generated at the endogenous chromosomal locus or, alternatively (or in addition to), novel allelic forms of (e.g., point mutations that ablate a transcription factor binding site) the endogenous locus to be created. In some aspects, the donor nucleic acid is an oligonucleotide wherein integration leads to a gene correction event, or a targeted deletion.

In some embodiments, the polynucleotide encoding the DNA binding protein and/or artificial transcription factor (e.g., ZFP-TF) is an mRNA. In some aspects, the mRNA may be chemically modified (See e.g. Kormann et al. (2011) *Nature Biotechnology* 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication No. 2012/0195936).

In yet another aspect, a gene delivery vector comprising one or more of the polynucleotides described herein is provided. In certain embodiments, the vector is an adenovirus vector (e.g., an Ad5/F35 vector), a lentiviral vector (LV) including integration competent or integration-defective lentiviral vectors, or an AAV vector (AAV), also referred to as a recombinant adenoassociated viral vector (rAAV). In certain embodiments, the AAV vector is an AAV6 or AAV9 vector. The AAV vector can comprise one or more of the polynucleotides shown in a single row of Table 3 (any one or more of SEQ ID NO:13-17). In certain embodiments, the AAV vector can with naturally occurred capsid sequence or artificially engineered capsid sequences. Thus, also provided herein are adenovirus (Ad) vectors, LV or a recombinant adeno-associated viral vectors (rAAV) comprising a sequence encoding at least one nuclease (ZFN or TALEN) and/or a donor sequence for targeted integration into a target gene. In certain embodiments, the Ad vector is a chimeric Ad vector, for example an Ad5/F35 vector. In certain embodiments, the lentiviral vector is an integrase-defective lentiviral vector (IDLV) or an integration competent lentiviral vector. In certain embodiments the vector is pseudo-typed with a VSV-G envelope, or with other envelopes.

Additionally, pharmaceutical compositions comprising the nucleic acids and/or proteins (e.g., ZFPs, Cas or TALEs and/or fusion molecules (e.g., artificial transcription factors comprising the ZFPs, Cas or TALEs) are also provided. For example, certain compositions include a nucleic acid comprising a sequence that encodes one of the ZFPs, Cas or TALEs described herein operably linked to a regulatory sequence, combined with a pharmaceutically acceptable carrier or diluent, wherein the regulatory sequence allows for expression of the nucleic acid in a cell. In certain embodiments, the ZFPs, CRISPR/Cas or TALEs encoded are specific for a HD HTT allele. In some embodiments, pharmaceutical compositions comprise ZFPs, CRISPR/Cas or TALEs that modulate a HD mHTT allele and ZFPs, CRISPR/Cas or TALEs that modulate a neurotrophic factor. Protein based compositions include one of more ZFPs. CRISPR/Cas or TALEs as disclosed herein and a pharmaceutically acceptable carrier or diluent. In certain embodiments, the pharmaceutical compositions comprise one or more of the proteins and/or polynucleotides of Table 3 for repression of HTT. In certain embodiments, pharmaceutical compositions comprising AAV vectors described herein comprise between $1\times10^7$ and $5\times10^{15}$ vg (or any value therebetween), even more preferably between $1\times10^7$ and $1\times10^{11}$ vg (or any value therebetween), even more preferably between $1\times10^8$ and $1\times10^{10}$ vg (or any value therebetween) of AAV-ZFP-TFs. In certain embodiments, AAV vectors are administered at a dose of between $1\times10^8$ and $1\times10^{10}$ (or any value therebetween) vg per striatum, including but not limited to 3e8, 3e9, or 3e10 9.2e9, 3.1e10 or 9.2e10 vg per each striatum) Intra-striatal administration may be to a single hemisphere or, preferably, bilaterally (at the same or different doses). In yet another aspect also provided is an isolated cell comprising any of the proteins, polynucleotides and/or compositions as described herein.

In another aspect, described herein are methods of modifying expression of an HTT gene in a cell (e.g., neuronal cell in vitro or in vivo in a brain of a subject, e.g., the striatum), the method comprising administering to the cell one or more proteins, polynucleotides, pharmaceutical compositions and/or cells as described herein. Administration (e.g., of pharmaceutical compositions comprising AAV ZFP-TFs as described herein) may be before and/or after the onset of disease symptoms at any dosage (e.g., between $1\times10^7$ and $5\times10^{15}$ AAV vg (or any value therebetween)) Administration may be one-time or repeated at any intervals and repeated administrations may be at the same or different dosages. The HTT gene may comprise at least one wild-type and/or mutant HTT allele. In certain embodiments, HTT expression is repressed, for example where mutant HTT (mHTT) expression is preferentially repressed as compared to wild-type expression. Repression or HTT, including selective repression of mHTT, may persist days, weeks, months or years after one or more administrations of ZFP-TFs as described herein. In certain embodiments, selective repression of mHTT (as compared to wild type HTT) persists 6 months or more after a single administration.

In another aspect, provided herein are methods for treating and/or preventing Huntington's Disease using the methods and compositions (proteins, polynucleotides and/or cells) described herein. In some embodiments, the methods involve compositions where the polynucleotides and/or proteins may be delivered using a viral vector, a non-viral vector (e.g., plasmid) and/or combinations thereof. Pharmaceutical compositions may also be delivered using standard techniques to the subject. In some embodiments, the methods involve compositions comprising stem cell populations comprising a ZFP or TALE, or altered with the ZFNs, TALENS, Ttago or the CRISPR/Cas nuclease system of the invention. The subject may comprise at least one mutant and/or wild-type HTT allele.

In a still further aspect, described here is a method of delivering one or more repressors of HTT (e.g., mHITT) to the brain of the subject using an rAAV (e.g., capsids AAV9 or AAV6) vector. Delivery may be to any brain region, for example, the striatum (e.g., putamen; intrastriatal injection including stereotactic striatal injections) by any suitable means including via the use of a cannula (for example intracranial injection). Administration into the brain (e.g., striatum) may be to a single hemisphere or may be bilateral (e.g., at the same or different doses when bilateral). In some embodiments, delivery is through direct injection into the intrathecal space. In further embodiments, delivery in through intravenous injection. The rAAV vector provides widespread delivery of the repressor to brain of the subject, including via anterograde and retrograde axonal transport to brain regions not directly administered the vector (e.g., delivery to the striatum) results in delivery to other structures such as the forebrain, hindbrain cortex, substantia nigra, thalamus, etc. In certain embodiments, the subject is a human and in other embodiments, the subject is a non-human primate. In certain embodiments, one or more proteins and/or polynucleotides (or pharmaceutical compositions comprising these proteins and/or polynucleotides) of Table 3 are delivered to the subject. Any one or combination of repressors shown in Table 3 may be used (e.g., 1, 2, 3, 4 or 5 repressors in any combinations).

Thus, in other aspects, described herein is a method of preventing and/or treating HD in a subject, the method comprising administering at least one repressor of a mutant HTT (mHT7) allele to the subject. The repressor may be administered in polynucleotide form, for example using a viral (e.g., AAV) and/or non-viral vector (e.g., plasmid and/or mRNA), in protein form and/or via a pharmaceutical composition as described herein (e.g., pharmaceutical compositions comprising one or more polynucleotide, one or more AAV vectors, one or more fusion molecules and/or one or more cells as described herein). In certain embodiments, the repressor is administered to the CNS (e.g., striatum) of the subject. The repressor may provide therapeutic benefits, including, but not limited to, reducing the formation of mHITT aggregates in HD neurons of a subject with HD (including reducing mHTT aggregation without effecting nuclear aggregation); reducing cell death in a neuron or population of neurons (e.g., an HD neuron or population of HD neurons); and/or reducing motor deficits (e.g., clasping, chorea, balance issues etc.) in HD subjects. In certain embodiments, mutant HTT expression is repressed by administration to the subject one or more proteins and/or polynucleotides (or pharmaceutical compositions comprising these proteins and/or polynucleotides) of Table 3 are delivered to the subject.

In any of the methods described herein, the repressor of the mutant HTT allele may be a ZFP-TF, for example a fusion protein comprising a ZFP that binds specifically to a mutant HTT allele and a transcriptional repression domain (e.g., KOX, KRAB, etc.). In certain embodiments, the ZFP-TF comprises a ZFP having the recognition helix regions of the ZFPs shown in a single row of Table 1, including the ZFP-TF repressors having the amino acid sequence or encoded by polynucleotides as shown in Table 3. In other embodiments, the repressor of the mutant HTT allele may be a TALE-TF or a CRISPR/Cas-TF where the nuclease domains in the Cas protein have been inactivated such that the protein no longer cleaves DNA. In still further embodiments, the repressor may comprise one or more nucleases (e.g., ZFN, TALEN and/or CRISPR/Cas system) that represses the mutant HTT allele by cleaving and thereby inactivating the mutant HTT allele. In certain embodiments, the nuclease introduces an insertion and/or deletion ("indel") via non-homologous end joining (NHEJ) following cleavage by the nuclease. In some embodiments, two nucleases cleave the CAG expansion region such that a large deletion is made in the region. In other embodiments, the nuclease introduces a donor sequence (by homology or non-homology directed methods), in which the donor integration inactivates the mutant HTT allele.

In any of the methods described herein, the repressor(s) may be delivered to the subject (e.g., brain) as a protein, polynucleotide or any combination of protein and polynucleotide. In certain embodiments, the repressor(s) is (are) delivered using an AAV (e.g., AAV9 or AAV6) vector. In other embodiments, at least one component of the repressor (e.g., sgRNA of a CRISPR/Cas system) is delivered as in RNA form. In other embodiments, the repressor(s) is (are) delivered using a combination of any of the expression constructs described herein, for example one repressor (or portion thereof) on one expression construct (e.g., AAV such as AAV9 or AAV6) and one repressor (or portion thereof) on a separate expression construct (rAAV or other viral or non-viral construct).

Furthermore, in any of the methods described herein, the repressors can be delivered at any concentration (dose) that provides the desired effect. As shown herein, HTT repression can be achieved in vivo with exposure as low as 1 VG/cell in the subject. In preferred embodiments, the repressor is delivered using a recombinant adeno-associated virus vector at 10,000-500,000 vector genome/cell (or any value therebetween). In certain embodiments, the repressor is delivered using a lentiviral vector at MOI between 250 and 10,000 (or any value therebetween). In other embodiments, the repressor is delivered using a plasmid construct at 150-1,500 ng/100,000 cells (or any value therebetween). In other embodiments, the repressor is delivered as mRNA at 0.003-1,500 ng/100,000 cells (or any value therebetween). In some embodiments, the AAV dose is calculated per animal (subject). For example, AAV vectors as described herein can comprise between $1\times10^7$ and $5\times10^{15}$ vg (or any value therebetween), even more preferably between $1\times10^7$ and $1\times10^{13}$ vg (or any value therebetween), even more preferably between $1\times10^8$ and $1\times10^{13}$ vg (or any value therebetween) of AAV-ZFP-TFs. Intra-striatal administration may be to a single hemisphere or, preferably, bilaterally (at the same or different doses). For example, in some embodiments, the repressor is delivered at approximately 9e9 VG/mouse, or between approximately 9e9 VG/mouse and 3e10 VG/mouse, or between approximately 3e10 VG/mouse and 9e10 VG/mouse. In some embodiments, the AAV dose is less than 9e9 VG/mouse (for example 6e8 VG/mouse or less), and in other embodiments, the AAV dose is greater that 9e10 VG/mouse.

In any of the methods described herein, the compositions and methods described herein can yield about 70% or greater, about 75% or greater, about 85% or greater, about 90% or greater, about 92% or greater, or about 95% or greater repression of the mutant HTT allele expression in one or more HD neurons of the subject. Furthermore, the compositions and methods described herein can exhibit selectivity for HTT (e.g., mHTT) repression (as compared to repression of off-target sites) by at least 50%, preferably 50%-90% (or any value therebetween), even more preferably greater than 90% as compared to the control.

In further aspects, the invention described herein comprises one or more HTT-modulating transcription factors, such as an HTT-modulating transcription factors comprising one or more of a zinc finger protein (ZFP TFs), a TALEs (TALE-TF), and a CRISPR/Cas-TFs for example, ZFP-TFs, TALE-TFs or CRISPR/Cas-TFs. In certain embodiments, the HTT-modulating transcription factor can repress expression of a mutant HTT allele in one or more HD neurons of a subject. The repression can be about 70% or greater, about 75% or greater, about 85% or greater, about 90% or greater, about 92% or greater, or about 95% or greater repression of the mutant HTT alleles in the one or more HD neurons of the subject as compared to untreated (e.g., wild-type) neurons of the subject. In certain embodiments, the HTT-modulating transcription factor can be used to achieve one or more of the methods described herein. In certain embodiments, the ZFP-TF comprises an amino acid sequence of a mHTT repressor as shown in Table 3.

In some embodiments, therapeutic efficacy is measured using the Unified Huntington's Disease Rating Scale (UHDRS) (Huntington Study Group (1996) *Mov Disord* 11(2):136-142) for analysis of overt clinical symptoms. In other embodiments, efficacy in patients is measured using PET and MRI imaging. In some embodiments, treatment with the mutant HTT modulating transcription factor prevents any further development of overt clinical symptoms and prevents any further loss of neuron functionality. In other embodiments, treatment with the mutant HTT modulating transcription factor improves clinical symptoms (e.g., motor function as determined using known measures such as clasping behavior, rotating rod analysis and the like) and improves neuron function.

Also provided is a kit comprising one or more of the HTT-modulators (e.g., repressors) and/or polynucleotides comprising components of and/or encoding the HTT-modulators (or components thereof) as described herein. The kits may further comprise cells (e.g., neurons), reagents (e.g., for detecting and/or quantifying mHTT protein, for example in CSF) and/or instructions for use, including the methods as described herein.

These and other aspects will be readily apparent to the skilled artisan in light of disclosure as a whole.

BRIEF DESCRIPTION OF THE DRAWINGS

FIG. 2A shows expression of HTT in human neural stem cells (NSCs) including either 17 CAG repeats (CAG 17 shown in left bars of each pair of bars) ("CAG" repeats disclosed as SEQ ID NO: 23) or 48 CAG repeats (CAG 48 shown in right bars of each pair of bars) ("CAG" repeats disclosed as SEQ ID NO: 23) following introduction of the indicated ZFP-TFs or control (GFP or mock) in mRNA form. The left most pair of bars for each ZFP show results when 1500 ng of mRNA was transfected into the cells; the pair of bars second from the left show results when 300 ng of mRNA was transfected into the cells; the pair of bars second from the right show results when 150 ng of mRNA was transfected and the right-most pair of bars show results when 15 ng of mRNA was transfected into the cells. The top graphs of FIG. 2B show relative HTT expression in HD neurons (with the indicated CAG repeats as in FIG. 2A) 21 days after infection with rAAV6 vectors encoding the indicated ZFP-TFs or controls (as in FIG. 2A). rAAV MOI for each pair of bars (CAG17 (17 "CAG" repeats disclosed as SEQ ID NO: 23) and CAG48 (48 "CAG" repeats disclosed as SEQ ID NO: 23)) are shown below the graph (500K, 300K, 100K, 10K and duplicate depicted in bars from left to right). The bottom graphs of FIG. 2B shows ZFP-TF copy number under the indicated conditions. Results using ZFP-TFs (45643 and 46025) are boxed.

FIG. 5A shows results in fibroblasts at the indicated ZFP mRNA dosages. FIG. 5B shows results (mRNA expression as a % of GFP expression) in neurons.

DETAILED DESCRIPTION

Figure 1:
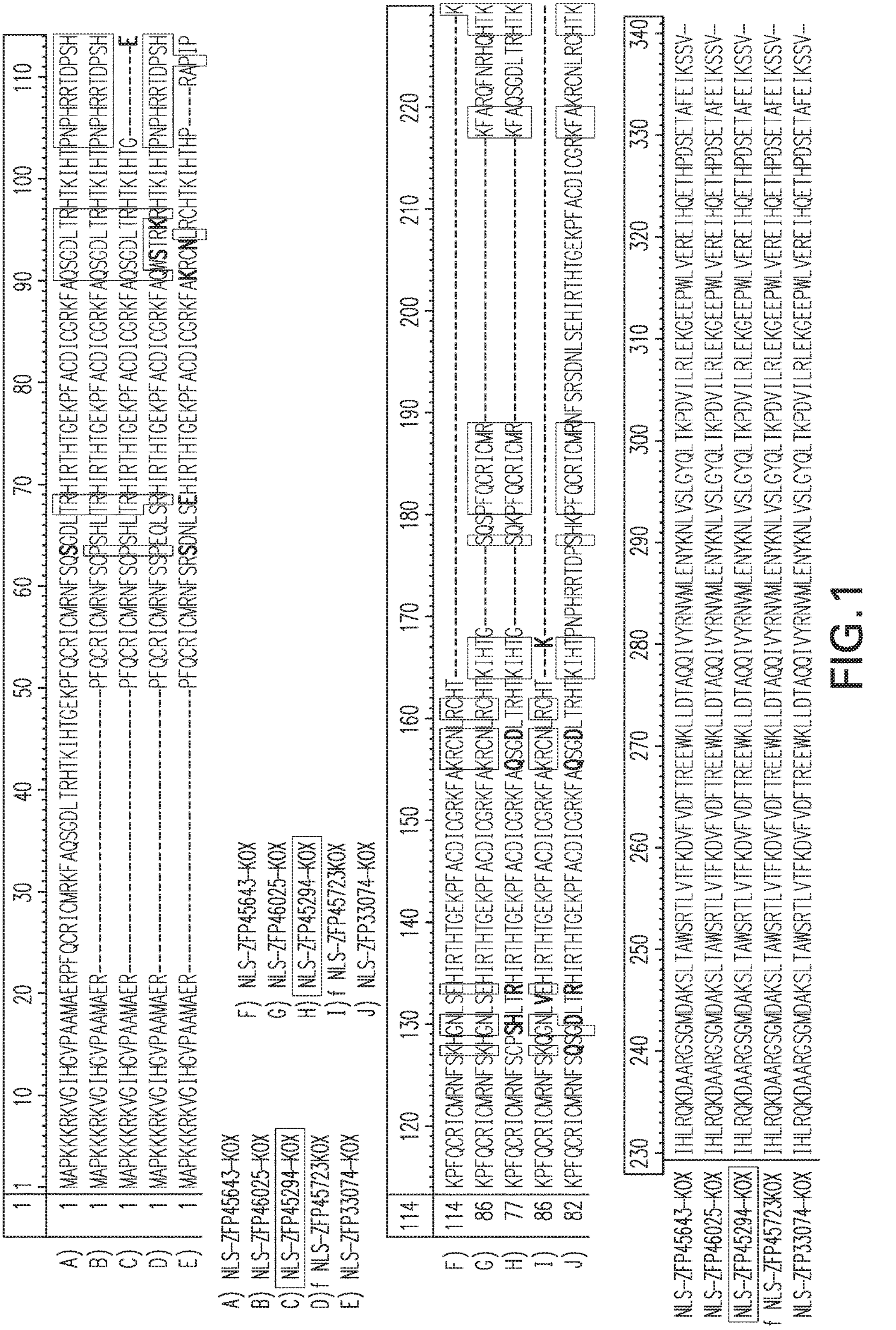
FIG. 1 shows an alignment of the protein (amino acid) sequences of the indicated ZFP-TFs (SEQ ID NO: 18-22). See, also, Table 3.

Disclosed herein are compositions and methods for widespread CNS delivery of compositions for detecting, monitoring disease progression, treating and/or preventing Huntington's disease (HD). In particular, the compositions and methods described herein use AAV9 vectors for delivery of mHTT repressors, which provides for the spread of functional mHTT repressors beyond the site of delivery. The m/ITT repressors (e.g., m/TT-modulating transcription factors, such as mHTT-modulating transcription factors comprising zinc finger proteins (ZFP TFs), TALEs (TALE-TF), or CRISPR/Cas-TFs for example, ZFP-TFs, TALE-TFs or CRISPR/Cas-TFs which repress expression of a mutant HTT allele) modify the CNS such that the effects and/or symptoms of HD are reduced or eliminated, for example by reducing the aggregation of HTT in HD neurons, by increasing HD neuron energetics (e.g., increasing ATP levels), by reducing apoptosis in HD neurons and/or by reducing motor deficits in HD subjects.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acid.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. No. 8,586,526.

"TtAgo" is a prokaryotic Argonaute protein thought to be involved in gene silencing. TtAgo is derived from the bacteria *Thermus thermophilus*. See, e.g., Swarts et al. (2014) *Nature* 507(7491):258-261, G. Sheng et al. (2013) *Proc. Natl. Acad. Sci. U.S.A.* 111:652). A "TtAgo system" is all the components required including, for example, guide DNAs for cleavage by a TtAgo enzyme. "Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

Zinc finger binding domains or TALE DNA binding domains can be "engineered" to bind to a predetermined nucleotide sequence, for example via engineering (altering one or more amino acids) of the recognition helix region of a naturally occurring zinc finger protein or by engineering the RVDs of a TALE protein. Therefore, engineered zinc finger proteins or TALEs are proteins that are non-naturally occurring. Non-limiting examples of methods for engineering zinc finger proteins or TALEs are design and selection. A "designed" zinc finger protein or TALE is a protein not occurring in nature whose design/composition results principally from rational criteria. Rational criteria for design include application of substitution rules and computerized algorithms for processing information in a database storing information of existing ZFP designs and binding data. A "selected" zinc finger protein or TALE is a protein not found in nature whose production results primarily from an empirical process such as phage display, interaction trap or hybrid selection. See, for example, U.S. Pat. Nos. 8,586,526; 6,140,081; 6,453,242; 6,746,838; 7,241,573; 6,866,997; 7,241,574 and 6,534,261; see also International Patent Publication No. WO 03/016496.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid. The term also includes systems in which a polynucleotide component associates with a polypeptide component to form a functional molecule (e.g., a CRISPR/Cas system in which a single guide RNA associates with a functional domain to modulate gene expression).

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "multimerization domain", (also referred to as a "dimerization domain" or "protein interaction domain") is a domain incorporated at the amino, carboxy or amino and carboxy terminal regions of a ZFP TF or TALE TF. These domains allow for multimerization of multiple ZFP TF or TALE TF units such that larger tracts of trinucleotide repeat domains become preferentially bound by multimerized ZFP TFs or TALE TFs relative to shorter tracts with wild-type numbers of lengths. Examples of multimerization domains include leucine zippers. Multimerization domains may also be regulated by small molecules wherein the multimerization domain assumes a proper conformation to allow for interaction with another multimerization domain only in the presence of a small molecule or external ligand. In this way, exogenous ligands can be used to regulate the activity of these domains.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, IRNA, IRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP or TALE protein as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP or TALE DNA-binding domain is fused to an activation domain, the ZFP or TALE DNA-binding domain and the activation domain are in operative linkage if, in the fusion polypeptide, the ZFP or TALE DNA-binding domain portion is able to bind its target site and/or its binding site, while the activation domain is able to upregulate gene expression. ZFPs fused to domains capable of regulating gene expression are collectively referred to as "ZFP-TFs" or "zinc finger transcription factors", while TALEs fused to domains capable of regulating gene expression are collectively referred to as "TALE-TFs" or "TALE transcription factors." When a fusion polypeptide in which a ZFP DNA-binding domain is fused to a cleavage domain (a "ZFN" or "zinc finger nuclease"), the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site. When a fusion polypeptide in which a TALE DNA-binding domain is fused to a cleavage domain (a "TALEN" or "TALE nuclease"), the TALE DNA-binding domain and the cleavage domain are in operative linkage if, in the fusion polypeptide, the TALE DNA-binding domain portion is able to bind its target site and/or its binding site, while the cleavage domain is able to cleave DNA in the vicinity of the target site. With respect to a fusion polypeptide in which a Cas DNA-binding domain is fused to an activation domain, the Cas DNA-binding domain and the activation domain are in operative linkage if, in the fusion polypeptide, the Cas DNA-binding domain portion is able to bind its target site and/or its binding site, while the activation domain is able to up-regulate gene expression. When a fusion polypeptide in which a Cas DNA-binding domain is fused to a cleavage domain, the Cas DNA-binding domain and the cleavage domain are in operative linkage if, in the fusion polypeptide, the Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and International Patent Publication No. WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors. The term includes viral and non-viral vectors, including but not limited to plasmid, mRNA, AAV (also referred to herein as "recombinant AAV" or "rAAV"), adenovirus vectors (Ad), lentiviral vectors (e.g., IDLV), and the like.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

DNA-Binding Domains

The methods described herein make use of compositions, for example HTT-modulating transcription factors, comprising a DNA-binding domain that specifically binds to a target sequence in an HTT gene, particularly that bind to a mutant HTT allele (mHTT) comprising a plurality of trinucleotide repeats. Any polynucleotide or polypeptide DNA-binding domain can be used in the compositions and methods disclosed herein, for example DNA-binding proteins (e.g., ZFPs or TALEs) or DNA-binding polynucleotides (e.g., single guide RNAs). In certain embodiments, the DNA-binding domain binds to a target site comprising 9 to 28 (or any value therebetween including 10, 11, 12, 13, 14, 15, 16, 17, 18, 19, 20, 21, 22, 23, 24, 25, 26 or 27) contiguous copies of nucleotides of SEQ ID NO:6.

In certain embodiments, the m/TT-modulating transcription factor, or DNA binding domain therein, comprises a zinc finger protein. Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453 and 6,200,759; and International Patent Publication Nos. WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536; and WO 03/016496.

In certain embodiments, the ZFPs can bind selectively to either a mutant HTT allele or a wild-type HTT sequence. HTT target sites typically include at least one zinc finger but can include a plurality of zinc fingers (e.g., 2, 3, 4, 5, 6 or more fingers). See, e.g., U.S. Pat. Nos. 9,234,016; 9,943,565; 8,841,260; 9,499,597; and U.S. Patent Publication Nos. 2015/0335708; 2018/0200332; 2017/0096460; 2017/0035839; 2016/0296605; and 2019/0322711. Usually, the ZFPs include at least three fingers. Certain of the ZFPs include four, five or six fingers, while some ZFPs include 7, 8, 9, 10, 11 or 12 fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, which domains can be transcriptional activation or repression domains. In some embodiments, the fusion protein comprises two ZFP DNA binding domains linked together. These zinc finger proteins can thus comprise 8, 9, 10, 11, 12 or more fingers. In some embodiments, the two DNA binding domains are linked via an extendable flexible linker such that one DNA binding domain comprises 4, 5, or 6 zinc fingers and the second DNA binding domain comprises an additional 4, 5, or 5 zinc fingers. In some embodiments, the linker is a standard inter-finger linker such that the finger array comprises one DNA binding domain comprising 8, 9, 10, 11 or 12 or more fingers. In other embodiments, the linker is an atypical linker such as a flexible linker. The DNA binding domains are fused to at least one regulatory domain and can be thought of as a 'ZFP-ZFP-TF' architecture. Specific examples of these embodiments can be referred to as "ZFP-ZFP-KOX" which comprises two DNA binding domains linked with a flexible linker and fused to a KOX repressor and "ZFP-KOX-ZFP-KOX" where two ZFP-KOX fusion proteins are fused together via a linker.

Alternatively, the DNA-binding domain may be derived from a nuclease. For example, the recognition sequences of homing endonucleases and meganucleases such as I-SceI, I-Ceul, PI-PspI, PI-Sce, 1-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22:1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 2007/0117128.

"Two handed" zinc finger proteins are those proteins in which two clusters of zinc finger DNA binding domains are separated by intervening amino acids so that the two zinc finger domains bind to two discontinuous target sites. An example of a two handed type of zinc finger binding protein is SIP1, where a cluster of four zinc fingers is located at the amino terminus of the protein and a cluster of three fingers is located at the carboxyl terminus (see Remacle et al. (1999) *EMBO Journal* 18(18):5073-5084). Each cluster of zinc fingers in these proteins is able to bind to a unique target sequence and the spacing between the two target sequences can comprise many nucleotides. Two-handed ZFPs may include a functional domain, for example fused to one or both of the ZFPs. Thus, it will be apparent that the functional domain may be attached to the exterior of one or both ZFPs (see, FIG. 1C) or may be positioned between the ZFPs (attached to both ZFPs) (see, FIG. 4).

Specific examples of HTT-targeted ZFPs are disclosed in Table 1 as well as in U.S. Pat. Nos. 9,234,016; 8,841,260; and 6,534,261; U.S. Patent Publication Nos. 2017/0096460; 2015/0056705; 2015/0335708; and 2019/0322711, which are incorporated by reference for all purposes in its entirety herein. The first column in this table is an internal reference name (number) for a ZFP and corresponds to the same name in column 1 of Table 2. "F" refers to the finger and the number following "F" refers which zinc finger (e.g., "F1" refers to finger 1).

TABLE 1

HTT-targeted zinc finger proteins #

| SBS # | Design F1 | F2 | F3 | F4 | F5 | F6 |
|---|---|---|---|---|---|---|
| 45643 | QSGDLTR (SEQ ID NO: 1) | QSGDLTR (SEQ ID NO: 1) | QSGDLTR (SEQ ID NO: 1) | KHGNLSE (SEQ ID NO: 2) | KRCNLRC (SEQ ID NO: 3) | |
| 46025 | CPSHLTR (SEQ ID NO: 4) | QSGDLTR (SEQ ID NO: 1) | KHGNLSE (SEQ ID NO: 2) | KRCNLRC (SEQ ID NO: 3) | RQENRHO (SEQ ID NO: 5) | |
| 45294 | CPSALIR (SEQ ID NO: 4) | QSGDLTR (SEQ ID NO: 1) | CPSHLTR (SEQ ID NO: 4) | QSGDLTR (SEQ ID NO: 1) | QSGDLTR (SEQ ID NO: 1) | |
| 45723 | SPEQLSR (SEQ ID NO: 7) | QWSTRKR (SEQ ID NO: 8) | KOGNIVE (SEQ ID NO: 9) | KRCNLRC (SEQ ID NO: 3) | N/A | |
| 33074 | RSDNLSE (SEQ ID NO: 10) | KRCNLRC (SEQ ID NO: 3) | QSGDLTR (SEQ ID NO: 1) | QSGDLTR (SEQ ID NO: 1) | RSDNLSE (SEQ ID NO: 10) | KRCNLRC (SEQ ID NO: 3) |

The sequence and location for the target sites of these proteins are disclosed in Table 2. Nucleotides in the target site that are contacted by the ZFP recognition helices are indicated in uppercase letters; non-contacted nucleotides indicated in lowercase.

TABLE 2

Target sites on human and mouse HTT

| SBS # | Target Site |
|---|---|
| 45643 | agCAGCAGcaGCAGCAGCAgcagcagca (SEQ ID NO: 6) |
| 46025 | agCAGCAGCAGcaGCAGCAgcagcagca (SEQ ID NO: 6) |
| 45294 | caGCAGCAGCAGCAGCAgcagcagcage (SEQ ID NO: 11) |
| 45723 | agCAGCAGcaGCAGCAgcagcagcagca (SEQ ID NO: 6) |
| 33074 | CAGCAGcaGCAGCAgCAGCAG (SEQ ID NO: 12) |

ZFP-TFs as described herein may also include one or more mutations outside recognition helix regions (e.g., to the backbone regions), including mutations as described in U.S. Patent Publication No. 2018/0087072.

In certain embodiments, the DNA-binding domain comprises a naturally occurring or engineered (non-naturally occurring) TAL effector (TALE) DNA binding domain. See, e.g., U.S. Pat. No. 8,586,526, incorporated by reference in its entirety herein.

The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay et al. (2007) *Science* 318:648-651). These proteins contain a DNA binding domain and a transcriptional activation domain. One of the most well characterized TALEs is AvrBs3 from *Xanthomonas campestgris* pv. *Vesicatoria* (see Bonas et al. (1989) *Mol Gen Genet* 218:127-136 and International Patent Publication No. WO 2010/079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see S. Schomack et al. (2006) *J Plant Physiol* 163(3):256-272). In addition, in the phytopathogenic bacteria *Ralstonia solanacearum* two genes, designated brg11 and hpx 17 have been found that are homologous to the AvrBs3 family of *Xanthomonas* in the *R. solanacearum* biovar 1 strain GMI1000 and in the biovar 4 strain RS1000 (See Heuer et al. (2007) *Appl and Envir Micro* 73(13):4379-4384). These genes are 98.9% identical in nucleotide sequence to each other but differ by a deletion of 1,575 bp in the repeat domain of hpx 17. However, both gene products have less than 40% sequence identity with AvrBs3 family proteins of *Xanthomonas*.

Specificity of these TALEs depends on the sequences found in the tandem repeats. The repeated sequence comprises approximately 102 bp and the repeats are typically 91-100% homologous with each other (Bonas et al. (1989) *Mol Gen Genet* 218:127-136). Polymorphism of the repeats is usually located at positions 12 and 13 and there appears to be a one-to-one correspondence between the identity of the hypervariable diresidues at positions 12 and 13 with the identity of the contiguous nucleotides in the TALE's target sequence (see Moscou and Bogdanove (2009) *Science* 326:1501 and Boch et al. (2009) *Science* 326:1509-1512). Experimentally, the code for DNA recognition of these TALEs has been determined such that an HD sequence at positions 12 and 13 leads to a binding to cytosine (C), NG binds to T, NI to A, C, G or T, NN binds to A or G, and NG binds to T. These DNA binding repeats have been assembled into proteins with new combinations and numbers of repeats, to make artificial transcription factors that are able to interact with new sequences. In addition, U.S. Pat. No. 8,586,526 and U.S. Patent Publication No. 2013/0196373, incorporated by reference in their entireties herein, describe TALEs with N-cap polypeptides, C-cap polypeptides (e.g., +63, +231 or +278) and/or novel (atypical) RVDs.

Exemplary TALEs are described in U.S. Patent Publication No. 2013/0253040, incorporated by reference in its entirety.

In certain embodiments, the DNA binding domains include a dimerization and/or multimerization domain, for example a coiled-coil (CC) and dimerizing zinc finger (DZ). See, U.S. Patent Publication No. 2013/0253040.

In still further embodiments, the DNA-binding domain comprises a single-guide RNA of a CRISPR/Cas system, for example sgRNAs as disclosed in U.S. Patent Publication No. 2015/0056705.

Compelling evidence has recently emerged for the existence of an RNA-mediated genome defense pathway in archaea and many bacteria that has been hypothesized to parallel the eukaryotic RNAi pathway (for reviews, see Godde and Bickerton (2006) *J. Mol. Evol.* 62:718-729; Lillestol et al. (2006) *Archaea* 2:59-72; Makarova et al. (2006) *Biol. Direct* 1:7; Sorek et al. (2008) *Nat. Rev. Microbiol.* 6:181-186). Known as the CRISPR-Cas system or prokaryotic RNAi (pRNAi), the pathway is proposed to arise from two evolutionarily and often physically linked gene loci: the CRISPR (clustered regularly interspaced short palindromic repeats) locus, which encodes RNA components of the system, and the cas (CRISPR-associated) locus, which encodes proteins (Jansen et al. (2002) *Mol. Microbiol.* 43:1565-1575; Makarova et al. (2002) *Nucleic Acids Res.* 30:482-496; Makarova et al. (2006) *Biol. Direct* 1:7; Haft et al. (2005) *PLOS Comput. Biol.* 1:e60). CRISPR loci in microbial hosts contain a combination of CRISPR-associated (Cas) genes as well as non-coding RNA elements capable of programming the specificity of the CRISPR-mediated nucleic acid cleavage. The individual Cas proteins do not share significant sequence similarity with protein components of the eukaryotic RNAi machinery, but have analogous predicted functions (e.g., RNA binding, nuclease, helicase, etc.) (Makarova et al. (2006) *Biol. Direct* 1:7). The CRISPR-associated (cas) genes are often associated with CRISPR repeat-spacer arrays. More than forty different Cas protein families have been described. Of these protein families, Cas1 appears to be ubiquitous among different CRISPR/Cas systems. Particular combinations of cas genes and repeat structures have been used to define 8 CRISPR subtypes (*E. coli*, Ypest, Nmeni, Dvulg, Tneap, Hmari, Apern, and Mtube), some of which are associated with an additional gene module encoding repeat-associated mysterious proteins (RAMPs). More than one CRISPR subtype may occur in a single genome. The sporadic distribution of the CRISPR/Cas subtypes suggests that the system is subject to horizontal gene transfer during microbial evolution.

The Type II CRISPR, initially described in *S. pyogenes*, is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences where processing occurs by a double strand-specific RNase III in the presence of the Cas9 protein. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. In addition, the tracrRNA must also be present as it base pairs with the crRNA at its 3' end, and this association triggers Cas9 activity. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation,' (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system.

Type II CRISPR systems have been found in many different bacteria. BLAST searches on publically available genomes by Fonfara et al. ((2013) *Nuc Acid Res* 42(4):2377-2590) found Cas9 orthologs in 347 species of bacteria. Additionally, this group demonstrated in vitro CRISPR/Cas cleavage of a DNA target using Cas9 orthologs from *S. pyogenes, S. mutans, S. therophilus, C. jejuni, N. meningitides, P. multocida* and *F. novicida*. Thus, the term "Cas9" refers to an RNA guided DNA nuclease comprising a DNA binding domain and two nuclease domains, where the gene encoding the Cas9 may be derived from any suitable bacteria.

The Cas9 protein has at least two nuclease domains: one nuclease domain is similar to a HNH endonuclease, while the other resembles a Ruv endonuclease domain. The HNH-type domain appears to be responsible for cleaving the DNA strand that is complementary to the crRNA while the Ruv domain cleaves the non-complementary strand. The Cas 9 nuclease can be engineered such that only one of the nuclease domains is functional, creating a Cas nickase (see Jinek et al. (2012) *Science* 337:816). Nickases can be generated by specific mutation of amino acids in the catalytic domain of the enzyme, or by truncation of part or all of the domain such that it is no longer functional. Since Cas 9 comprises two nuclease domains, this approach may be taken on either domain. A double strand break can be achieved in the target DNA by the use of two such Cas 9 nickases. The nickases will each cleave one strand of the DNA and the use of two will create a double strand break.

The requirement of the crRNA-tracrRNA complex can be avoided by use of an engineered "single-guide RNA" (sgRNA) that comprises the hairpin normally formed by the annealing of the crRNA and the tracrRNA (see Jinek et al. (2012) *Science* 337:816 and Cong et al. (2013) *Science* 339(6121):819-823, *Sciencexpress*/10.1126/science.1231143). In *S. pyrogenes*, the enginecred tracrRNA: crRNA fusion, or the sgRNA, guides Cas9 to cleave the target DNA when a double strand RNA: DNA heterodimer forms between the Cas associated RNAs and the target DNA. This system comprising the Cas9 protein and an engineered sgRNA containing a PAM sequence has been used for RNA guided genome editing (see Ramalingam (2013) *Genome Biol.* 14(2):107) and has been useful for zebrafish embryo genomic editing in vivo (see Hwang et al. (2013) *Nature Biotechnology* 31(3):227) with editing efficiencies similar to ZFNs and TALENs.

The primary products of the CRISPR loci appear to be short RNAs that contain the invader targeting sequences, and are termed guide RNAs or prokaryotic silencing RNAs (psiRNAs) based on their hypothesized role in the pathway (Makarova et al. (2006) *Biol. Direct* 1:7; Hale et al. (2008) *RNA* 14:2572-2579). RNA analysis indicates that CRISPR locus transcripts are cleaved within the repeat sequences to release "60- to 70-nt RNA intermediates that contain individual invader targeting sequences and flanking repeat fragments (Tang et al. (2002) *Proc. Natl. Acad. Sci.* 99:7536-7541; Tang et al. (2005) *Mol. Microbiol.* 55:469-481; Lillestol et al. (2006) *Archaea* 2:59-72; Brouns et al. (2008) *Science* 321:960-964; Hale et al. (2008) *RNA* 14:2572-2579). In the archaeon *Pyrococcus furiosus*, these intermediate RNAs are further processed to abundant, stable "35- to 45-nt mature psiRNAs (Hale et al. (2008) *RNA* 14:2572-2579).

The requirement of the crRNA-tracrRNA complex can be avoided by use of an engineered "single-guide RNA" (sgRNA) that comprises the hairpin normally formed by the annealing of the crRNA and the tracrRNA (see Jinek et al. (2012) *Science* 337:816 and Cong et al. (2013) *Science* 339(6121):819-823, *Sciencexpress*/10.1126/science.1231143). In *S. pyrogenes*, the engineered tracrRNA: crRNA fusion, or the sgRNA, guides Cas9 to cleave the target DNA when a double strand RNA: DNA heterodimer forms between the Cas associated RNAs and the target DNA. This system comprising the Cas9 protein and an engineered sgRNA containing a PAM sequence has been used for RNA guided genome editing (see Ramalingam (2013) *Genome Biol.* 14(2):107) and has been useful for zebrafish embryo genomic editing in vivo (see Hwang et al. (2013) *Nature Biotechnology* 31(3):227) with editing efficiencies similar to ZFNs and TALENs.

Chimeric or sgRNAs can be engineered to comprise a sequence complementary to any desired target. In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. In some embodiments, the RNAs comprise 22 bases of complementarity to a target and of the form G[n19], followed by a protospacer-adjacent motif (PAM) of the form NGG or NAG for use with a *S. pyogenes* CRISPR/Cas system. Thus, in one method, sgRNAs can be designed by utilization of a known ZFN target in a gene of interest by (i) aligning the recognition sequence of the ZFN heterodimer with the reference sequence of the relevant genome (human, mouse, or of a particular plant species); (ii) identifying the spacer region between the ZFN half-sites; (iii) identifying the location of the motif G[N20]GG that is closest to the spacer region (when more than one such motif overlaps the spacer, the motif that is centered relative to the spacer is chosen); (iv) using that motif as the core of the sgRNA. This method advantageously relies on proven nuclease targets. Alternatively, sgRNAs can be designed to target any region of interest simply by identifying a suitable target sequence the conforms to the G[n20]GG formula. Along with the complementarity region, an sgRNA may comprise additional nucleotides to extend to tail region of the tracrRNA portion of the sgRNA (see Hsu et al. (2013) *Nature Biotech* doi:10.1038/nbt.2647). Tails may be of +67 to +85 nucleotides, or any number therebetween with a preferred length of +85 nucleotides. Truncated sgRNAs may also be used, "tru-gRNAs" (see Fu et al. (2014) *Nature Biotech* 32(3):279). In tru-gRNAs, the complementarity region is diminished to 17 or 18 nucleotides in length.

Further, alternative PAM sequences may also be utilized, where a PAM sequence can be NAG as an alternative to NGG (Hsu (2013) *Nature Biotech* 31:827-832, doi:10.1038/nbt.2647) using a *S. pyogenes* Cas9. Additional PAM sequences may also include those lacking the initial G (Sander and Joung (2014) *Nature Biotech* 32(4):347). In addition to the *S. pyogenes* encoded Cas9 PAM sequences, other PAM sequences can be used that are specific for Cas9 proteins from other bacterial sources. For example, the PAM sequences shown below (adapted from Sander and Joung, supra, and Esvelt et al. (2013) *Nat Meth* 10(11):1116) are specific for these Cas9 proteins:

| Species | PAM |
|---|---|
| *S. pyogenes* | NGG |
| *S. pyogenes* | NAG |
| *S. mutans* | NGG |
| *S. thermophilius* | NGGNG |
| *S. thermophilius* | NNAAAW |
| *S. thermophilius* | NNAGAA |
| *S. thermophilius* | NNNGATT |
| *C. jejuni* | NNNNACA |
| *N. meningitides* | NNNNGATT |
| *P. multocida* | GNNNCNNA |
| *F. novicida* | NG |

Thus, a suitable target sequence for use with a *S. pyogenes* CRISPR/Cas system can be chosen according to the following guideline: [n17, n18, n19, or n20](G/A) G. Alternatively the PAM sequence can follow the guideline G [n17, n18, n19, n20](G/A) G. For Cas9 proteins derived from non-*S. pyogenes* bacteria, the same guidelines may be used where the alternate PAMs are substituted in for the *S. pyogenes* PAM sequences.

Most preferred is to choose a target sequence with the highest likelihood of specificity that avoids potential off target sequences. These undesired off target sequences can be identified by considering the following attributes: i) similarity in the target sequence that is followed by a PAM sequence known to function with the Cas9 protein being utilized; ii) a similar target sequence with fewer than three mismatches from the desired target sequence; iii) a similar target sequence as in ii), where the mismatches are all located in the PAM distal region rather than the PAM proximal region (there is some evidence that nucleotides 1-5 immediately adjacent or proximal to the PAM, sometimes referred to as the 'seed' region (Wu et al. (2014) *Nature Biotech* 32:670-676, doi:10.1038/nbt2889) are the most critical for recognition, so putative off target sites with mismatches located in the seed region may be the least likely be recognized by the sg RNA); and iv) a similar target sequence where the mismatches are not consecutively spaced or are spaced greater than four nucleotides apart (Hsu et al. (2014) *Cell* 157(6):1262-78). Thus, by performing an analysis of the number of potential off target sites in a genome for whichever CRIPSR/Cas system is being employed, using these criteria above, a suitable target sequence for the sgRNA may be identified.

In some embodiments, the CRISPR-Cpf1 system is used. The CRISPR-Cpf1 system, identified in *Francisella* spp, is a class 2 CRISPR-Cas system that mediates robust DNA interference in human cells. Although functionally conserved, Cpf1 and Cas9 differ in many aspects including in their guide RNAs and substrate specificity (see Fagerlund et al. (2015) *Genom Bio* 16:251). A major difference between Cas9 and Cpf1 proteins is that Cpf1 does not utilize tracrRNA, and thus requires only a crRNA. The FnCpf1 crRNAs are 42-44 nucleotides long (19-nucleotide repeat and 23-25-nucleotide spacer) and contain a single stem-loop, which tolerates sequence changes that retain secondary structure. In addition, the Cpf1 crRNAs are significantly shorter than the ~100-nucleotide engineered sgRNAs required by Cas9, and the PAM requirements for FnCpf1 are 5'-TTN-3' and 5'-CTA-3' on the displaced strand. Although both Cas9 and Cpf1 make double strand breaks in the target DNA, Cas9 uses its RuvC- and HNH-like domains to make blunt-ended cuts within the seed sequence of the guide RNA, whereas Cpf1 uses a RuvC-like domain to produce staggered cuts outside of the seed. Because Cpf1 makes staggered cuts away from the critical seed region, NHEJ will not disrupt the target site, therefore ensuring that Cpf1 can continue to cut the same site until the desired HDR recombination event has taken place. Thus, in the methods and compositions described herein, it is understood that the term "Cas" includes both Cas9 and Cfp1 proteins. Thus, as used herein, a "CRISPR/Cas system" refers both CRISPR/Cas and/or CRISPR/Cfp1 systems, including both nuclease, nickase and/or transcription factor systems.

In some embodiments, other Cas proteins may be used. Some exemplary Cas proteins include Cas9, Cpf1 (also known as Cas12a), C2c1, C2c2 (also known as Cas13a), C2c3, Cas1, Cas2, Cas4, CasX and CasY; and include engineered and natural variants thereof (Burstein et al. (2017) *Nature* 542:237-241) for example HF1/spCas9 (Kleinstiver et al. (2016) *Nature* 529:490-495; Cebrian-Serrano and Davies (2017) *Mamm Genome* 28(7):247-261); split Cas9 systems (Zetsche et al. (2015) *Nat Biotechnol* 33(2):139-142), trans-spliced Cas9 based on an intein-extein system (Troung et al. (2015) *Nucl Acid Res* 43(13):6450-8); mini-SaCas9 (Ma et al. (2018) *ACS Synth Biol* 7(4):978-985). Thus, in the methods and compositions described herein, it is understood that the term "Cas" includes all Cas variant proteins, both natural and engineered.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. In some aspects, a functional derivative may comprise a single biological property of a naturally occurring Cas protein. In other aspects, a function derivative may comprise a subset of biological properties of a naturally occurring Cas protein. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

Exemplary CRISPR/Cas nuclease systems targeted to specific genes are disclosed for example, in U.S. Patent Publication No. 2015/0056705.

Thus, the nuclease comprises a DNA-binding domain in that specifically binds to a target site in any gene into which it is desired to insert a donor (transgene) in combination with a nuclease domain that cleaves DNA.

Fusion Molecules

The DNA-binding domains may be fused to any additional molecules (e.g., polypeptides) for use in the methods described herein. In certain embodiments, the methods employ fusion molecules comprising at least one DNA-binding molecule (e.g., ZFP, TALE or single guide RNA) and a heterologous regulatory (functional) domain (or functional fragment thereof).

In certain embodiments, the functional domain comprises a transcriptional regulatory domain. Common domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, belicases, ligascs, kinases, phosphatases, polymerases, endonucleases) and their associated factors and modifiers. See, e.g., U.S. Patent Publication No. 2013/0253040, incorporated by reference in its entirety herein.

Suitable domains for achieving activation include the HSV VP16 activation domain (see, e.g., Hagmann et al. (1997) *J. Virol.* 71:5952-5962) nuclear hormone receptors (see, e.g., Torchia et al. (1998) *Curr. Opin. Cell. Biol.* 10:373-383); the p65 subunit of nuclear factor kappa B (Bitko & Barik (1998) *J. Virol.* 72:5610-5618 and Doyle & Hunt (1997) *Neuroreport* 8:2937-2942; Liu et al. (1998) *Cancer Gene Ther.* 5:3-28), or artificial chimeric functional domains such as VP64 (Beerli et al. (1998) *Proc. Natl. Acad. Sci. USA* 95:14623-33), and degron (Molinari et al. (1999) *EMBO J.* 18:6439-6447). Additional exemplary activation domains include, October 1, Oct-2A, Sp1, AP-2, and CTF1 (Seipel et al. (1992) *EMBO J.* 11:4961-4968) as well as p300, CBP, PCAF, SRC1 PvALF, AtHD2A and ERF-2. See, for example, Robyr et al. (2000) *Mol. Endocrinol.* 14:329-347; Collingwood et al. (1999) *J. Mol. Endocrinol.* 23:255-275; Leo et al. (2000) *Gene* 245:1-11; Manteuffel-Cymborowska (1999) *Acta Biochim. Pol.* 46:77-89; Mckenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, API, ARF-5, -6, -7, and -8, CPRFI, CPRF4, MYC-RP/GP, and TRABI. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

Exemplary repression domains include, but are not limited to, KRAB A/B, KOX, TGF-beta-inducible early gene (TIEG), v-erbA, SID, MBD2, MBD3, members of the DNMT family (e.g., DNMTI, DNMT3A, DNMT3B), Rb, and MeCP2. See, for example, Bird et al. (1999) *Cell* 99:451-454; Tyler et al. (1999) *Cell* 99:443-446; Knopfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, IL) Catalogue. Methods and compositions for making fusions between a minor groove binder and a polypeptide have been described. Mapp et al. (2000) *Proc. Natl. Acad. Sci. USA* 97:3930-3935.

The fusion molecule may be formulated with a pharmaceutically acceptable carrier, as is known to those of skill in the art. See, for example, Remington's Pharmaceutical Sciences, 17th ed., 1985; and co-owned International Patent Publication No. WO 00/42219.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

In certain embodiments, the fusion molecule comprises one or more ZFP-TFs (repressors) in which the ZFP is operably linked to a transcriptional repression domain. Non-limiting examples of repression domains include KOX (KRAB) domains and the like. Additional elements may also be included, for example an NLS and any linkers may be used between the zinc finger domains and/or between the ZFP and the repression domain (and/or any additional elements). Polynucleotides encoding these ZFP-TF repressors may also include further additional elements such as a promoter driving expression of the ZFP-TF, enhancers, insulators, and the like.

Table 3 shows the polynucleotide and amino acid sequences of exemplary ZFP-TFs comprising the ZFPs described herein (identified by name in the first column). The recognition helix region sequences (Table 1) are underlined in Table 3; the NLS peptide is shown in bold and the repression domain shown in italics.

TABLE 3

Nucleotide and Amino Acid Sequence of ZFP-TFs

| ZFP-TF | DNA sequence | Protein Sequence |
|---|---|---|
| NLS-<br>ZFP4564<br>3-KOX | atggcccccaagaaaaagcggaaagtgggcatccacgggg<br>tacccgccgctatggctgagaggcccttccagtgtcgaat<br>ctgcatgcgtaagtttgcccagtccggcgacctgacccgc<br>cataccaagatacacacgggcgagaagcccttccagtgtc<br>gaatctgcatgcgtaacttcagtcagtccggcgacctgac<br>ccgccacatccgcacccacaccggcgagaagccttttgcc<br>tgtgacatttgtgggaggaaatttgcccagtccggcgacc<br>tgacccgccataccaagatacacacgccgaacccgcaccg<br>ccgcaccgacccgtcccacaagcccttccagtgtcgaatc<br>tgcatgcgtaacttcagtaagcacggcaacctgtccgagc<br>acatccgcacccacaccggcgagaagccttttgcctgtga<br>catttgtgggaggaaatttgccaagcgctgtaacctgcgc<br>tgtcataccaagatacacctgcgccaaaaagatgcggccc<br>ggggatccggcatggatgctaagtcactaactgcctggtc<br>ccggacactggtgaccttcaaggatgtatttgtggacttc<br>accagggaggagtggaagctgctggacactgctcagcaga | MAPKKKRKVGIHGVPAAMAERPF<br>QCRICMRKFAQSGDLTRHTKIHT<br>GEKPFQCRICMRNESQSGDLTRH<br>IRTHTGEKPFACDICGRKFAQSG<br>DLTRHTKIHTPNPHRRTDPSHKP<br>FQCRICMRNFSKHGNLSEHIRTH<br>TGEKPFACDICGRKFAKRCNLRC<br>HTKIHLRQKDAARGSGMDAKSLT<br>AWSRTLVTFKDVFVDFTREEWKL<br>LDTAQQIVYRNVMLENYKNLVSL<br>GYQLTKPDVILRLEKGEEPWLVE<br>REIHQETHPDSETAFEIKSSV<br>(SEQ ID NO: 18) |

TABLE 3-continued

Nucleotide and Amino Acid Sequence of ZFP-TFs

| ZFP-TF | DNA sequence | Protein Sequence |
|---|---|---|
| | tcgtgtacagaaatgtgatgctggagaactataagaacct<br>ggtttccttgggttatcagcttactaagccagatgtgatc<br>ctccggttggagaagggagaagagccctggctggtggaga<br>gagaaattcaccaagagacccatcctgattcagagactgc<br>atttgaaatcasatcatcagtttaa (SEQ ID<br>NO: 13) | |
| NLS-<br>ZFP4602<br>5-KOX | atggcccccaagaaaaagcggaaagtgggcatccacgggg<br>tacccgccgctatggctgagaggcccttccagtgtcgaat<br>ctgcatgcgtaacttcagttgtccgtcccacctgacccgc<br>cacatccgcacccacaccggcgagaagccttttgcctgtg<br>acatttgtgggaggaaatttgcccagtccggcgacctgac<br>ccgccataccaagatacacacgcctaatcctcatcgccgc<br>actgatcccagccataagcccttccagtgtcgaatctgca<br>tgcgtaacttcagtaagcacggcaacctgtccgagcacat<br>ccgcacccacaccggcgagaagccttttgcctgtgacatt<br>tgtgggaggaaatttgccaagcgctgtaacctgcgctgtc<br>ataccaagatacacacgggctcccaatccccttccagtg<br>tcgaatctgcatgcgtaagtttgcccgccagttcaaccgc<br>caccagcataccaagatacacctgcgccaaaaagatgcgg<br>cccggggatccggcatggatgctaagtcactaactgcctg<br>gtcccggacactggtgaccttcaaggatgtatttgtggac<br>ttcaccagggaggagtggaagctgctggacactgctcagc<br>agatcgtgtacagaaatgtgatgctggagaactataagaa<br>cctggtttccttgggttatcagcttactaagccagatgtg<br>atcctccggttggagaagggagaagagccctggctggtgg<br>agagagaaattcaccaagagacccatoctgattcagagac<br>tgcatttgaaatcaaatcatcagttta (SEQ ID<br>NO: 14) | MAPKKKRKVGIHGVPAAMAERPF<br>QCRICMRNFSCPSHLTRHIRTHT<br>GEKPFACDICGRKFAQSGDLTRH<br>TKIHTPNPHRRTDPSHKPFQCRI<br>CMRNFSKHGNLSEHIRTHTGEKP<br>FACDICGRKFAKRCNLRCHTKIH<br>TGSQSPFQCRICMRKFARQFNRH<br>QHTKIHLRQKDAARGSGMDAKSL<br>TAWSRTLVTFKDVFVDFTREEWK<br>LLDTAQQIVYRNVMLENYKNLVS<br>LGYQLTKPDVILRLEKGEEPWLV<br>EREIHQETHPDSETAFEIKSSV<br>(SEQ ID NO: 19) |
| NLS-<br>ZFP4529<br>4-KOX | Atggcccccaagaaaaagcggaaagtgggcatccacgggg<br>tacccgccgctatggctgagaggcccttccagtgtcgaat<br>ctgcatgcgtaacttcagttgtccgtcccacctgacccgc<br>cacatccgcacccacaceggcgagaagccttttgcctgtg<br>acatttgtgggaggaaatttgcccagtccggcgacctgac<br>ccgccataccaagatacacacgggcgagaagcccttccag<br>tgtcgaatctgcatgcgtaacttcagttgtccgtcccacc<br>tgacccgccacatccgcacccacaccggcgagaagccttt<br>tgcctgtgacatttgtgggaggaaatttgcccagtccggc<br>gacctgacccgccataccaagatacacacgggatctcaga<br>agcccttccagtgtcgaatctgcatgcgtaagtttgccca<br>gtccggcgacctgacccgccataccaagatacacctgcgc<br>caaaaagatgcggcccggggatccggcatggatgctaagt<br>cactaactgcctggtcccggacactggtgaccttcaagga<br>tgtatttgtggacttcaccagggaggagtggaagctgctg<br>gacactgctcagcagatogtgtacagaaatgtgatgctgg<br>agaactataagaacctggtttccttgggttatcagcttac<br>taagccagatgtgatcctccggttggagaagggagaagag<br>ccctggctggtggagagagaaattcaccaagagacccatc<br>ctgattcagagactgcatttgaaatcaaatcatcagttta<br>(SEQ ID NO: 15) | MAPKKKRKVGIHGVPAAMAERPF<br>QCRICMRNFSCPSHLTRHIRTHT<br>GEKPFACDICGRKFAQSGDLTRH<br>TKIHTGEKPFQCRICMRNFSCPS<br>HLTRHIRTHTGEKPFACDICGRK<br>FAQSGDLTRHTKIHTGSQKPFQC<br>RICMRKFAQSGDLTRHTKIHLRQ<br>KDAARGSGMDAKSLTAWSRTLVT<br>FKDVEVDFTREEWKLLDTAQQIV<br>YRNVMLENYKNLVSLGYQLTKPD<br>VILRLEKGEEPWLVEREIHQETH<br>PDSETAFEIKSSV (SEQ ID<br>NO: 20) |
| NLS-<br>ZFP4572<br>3-KOX | atggcccccaagaaaaagcggaaagtgggcatccacgggg<br>tacccgccgctatggctgagaggcccttccagtgtcgaat<br>ctgcatgcgtaacttcagttccccggagcagctgtcccgc<br>cacatccgcacccacaccggcgagaagccttttgcctgtg<br>acatttgtgggaggaaatttgcccagtggtccacccgcaa<br>gcgccataccaagatacacacgccgaacccgcaccgccgc<br>accgacccgtcccacaagcccttccagtgtcgaatctgca<br>tgcgtaacttcagtaagcagggcaacctggtggagcacat<br>ccgcacccacaccggcgagaagccttttgcctgtgacatt<br>tgtgggaggaaatttgccaagcgctgtaacctgcgctgtc<br>ataccaagatacacctgcgccaaaaagatgcggcccgggg<br>atccggcatggatgctaagtcactaactgcctggtcccgg<br>acactggtgaccttcaaggatgtatttgtggacttcacca<br>gggaggagtggaagctgctggacactgctcagcagatcgt<br>gtacagaaatgtgatgctggagaactataagaacctggtt<br>tccttgggttatcagcttactaagccagatgtgatcctcc<br>ggttggagaagggagaagagccctggctggtggagagaga<br>aattcaccaagagacccatcctgattcagagactgcattt<br>gaaatcasatcatcagttta (SEQ ID NO: 16) | MAPKKKRKVGIHGVPAAMAERPF<br>QCRICMRNESSPEQLSRHIRTHT<br>GEKPFACDICGRKFAQWSTRKRH<br>TKIHTPNPHRRTDPSHKPFQCRI<br>CMRNFSKQGNLVEHIRTHTGEKP<br>FACDICGRKFAKRCNLRCHTKIH<br>LRQKDAARGSGMDAKSLTAWSRT<br>LVTFKDVFVDETREEWKLLDTAQ<br>QIVYRNVMLENYKNLVSLGYQLT<br>KPDVILRLEKGEEPWLVEREIHQ<br>ETHPDSETAFEIKSSV (SEQ<br>ID NO: 21) |
| NIS-<br>ZEP3307<br>4-KOX | atgcccccaagaaaaagcggasagtgggcatccacggggt<br>acccgccgctatggctgagaggcccttccagtgtcgaatc<br>tgcatgcgtaacttcagtcgctccgacaacctgtccgagc<br>acatccgcacccacaccggcgagaagccttttgcctgtga<br>catttgtgggaggaaatttgccaagcgctgtaacctgcgc | MAPKKKRKVGIHGVPAAMAERPF<br>QCRICMRNFSRSDNLSEHIRTHT<br>GEKPFACDICGRKEAKRCNLRCH<br>TKIHTHPRAPIPKPFQCRICMRN<br>FSQSGDLTRHIRTHTGEKPFACD |

TABLE 3-continued

Nucleotide and Amino Acid Sequence of ZFP-TFs

| ZFP-TF | DNA sequence | Protein Sequence |
|---|---|---|
| | tgtcataccaagatacacacgcatcccagggcacctattc ccaagcccttccagtgtcgaatctgcatgcgtaacttcag tcagtccggcgacctgacccgccacatccgcacccacacc ggcgagaagccttttgcctgtgacatttgtgggaggaaat ttgcccagtccggcgacctgacccgccataccaagataca cacgccgaacccgcaccgccgcaccgacccgtcccacaag cccttccagtgtcgaatctgcatgcgtaacttcagtcgct ccgacaacctgtccgagcacatccgcacccacaccggcga gaagccttttgcctgtgacatttgtgggaggasatttgcc aagcgctgtaacctgcgctgtcataccaagatacacctgc gccaaaaagatgcggcccggggatccggcatggatgctaa gtcactaactgcctggtcccggacactggtgaccttcaag gatgtatttgtggacttcaccagggaggagtggaagctgc tggacactgctcagcagatcgtgtacagaaatgtgatgct ggagaactataagaacctggtttccttgggttatcagctt actaagccagatgtgatcctccggttggagaagggagaag agccctggctggtggagagagaaattcaccaagagaccca tcctgattcagagactgcatttgaaatcaaatcatcagtt ta (SEQ ID NO: 17) | ICGRKFAQSGDLTRHTKIHTPNP HRRTDPSHKPFQCRICMRNESRS DNLSEHIRTHTGEKPFACDICGR KFAKRCNLRCHTKIHLRQKDAAR GSGMDAKSLTAWSRTLVTFKDVE VDFTREEWKLLDTAQQIVYRNVM LENYKNIVSLGYQLTKPDVILRL EKGEEPWLVEREIHQETHPDSET AFEIKSSV (SEQ ID NO: 22) |

The polynucleotides encoding the repressors described herein may be delivered using any suitable expression vector, including but not limited to viral (e.g., AAV, Ad, etc.) and non-viral vectors (e.g., mRNA, plasmid, minicircle, etc.). The expression vectors may include additional elements such as a nuclear localization signal (NLS) and/or promoter to drive expression of the repressor (e.g., a constitutive promoter such as the CMV promoter). One or more polynucleotides (e.g., expression vectors) of the same or different form (e.g., viral and/or non-viral vectors) may be delivered to the subject and may be formulated in one or more pharmaceutical compositions. The polynucleotides described herein may be maintained episomally (extra-chromosomally) and/or may be stably integrated into a cell following delivery.

In certain embodiments, the fusion protein comprises a DNA-binding domain and a nuclease domain to create functional entities that are able to recognize their intended nucleic acid target through their engineered (ZFP or TALE) DNA binding domains and create nucleases (e.g., zinc finger nuclease or TALE nucleases) cause the DNA to be cut near the DNA binding site via the nuclease activity.

Thus, the methods and compositions described herein are broadly applicable and may involve any nuclease of interest. Non-limiting examples of nucleases include meganucleases, TALENs and zinc finger nucleases. The nuclease may comprise heterologous DNA-binding and cleavage domains (e.g., zinc finger nucleases; TALENs; meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site).

The nuclease domain may be derived from any nuclease, for example any endonuclease or exonuclease. Non-limiting examples of suitable nuclease (cleavage) domains that may be fused to HTT DNA-binding domains as described herein include domains from any restriction enzyme, for example a Type IIS Restriction Enzyme (e.g., FokI). In certain embodiments, the cleavage domains are cleavage half-domains that require dimerization for cleavage activity. See, e.g., U.S. U.S. Pat. Nos. 8,586,526; 8,409,861; and 7,888,121, incorporated by reference in their entireties herein. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing.

The nuclease domain may also be derived any meganuclease (homing endonuclease) domain with cleavage activity may also be used with the nucleases described herein, including but not limited to I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII.

In certain embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the meganuclease (e.g., TevI) nuclease domain (see Beurdeley et al. (2013) *Nat Comm* 4:1762, doi:10.1038/ncomms2782). In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al. (2013) *Nucl Acid Res* 42(4):2591-601, doi:10.1093/nar/gkt1224).

In addition, the nuclease domain of the meganuclease may also exhibit DNA-binding functionality. Any TALENs may be used in combination with additional TALENs (e.g., one or more TALENs (cTALENs or FokI-TALENs) with one or more mega-TALs) and/or ZFNs.

In addition, cleavage domains may include one or more alterations as compared to wild-type, for example for the formation of obligate heterodimers that reduce or eliminate off-target cleavage effects. See, e.g., U.S. Pat. Nos. 7,914,796; 8,034,598; and 8,623,618, incorporated by reference in their entireties herein.

Nucleases as described herein may generate double- or single-stranded breaks in a double-stranded target (e.g., gene). The generation of single-stranded breaks ("nicks") is described, for example in U.S. Pat. No. 8,703,489, incorporated herein by reference which describes how mutation of the catalytic domain of one of the nucleases domains results in a nickase.

Thus, a nuclease (cleavage) domain or cleavage half-domain can be any portion of a protein that retains cleavage activity, or that retains the ability to multimerize (e.g., dimerize) to form a functional cleavage domain.

Alternatively, nucleases may be assembled in vivo at the nucleic acid target site using so-called "split-enzyme" technology (see e.g. U.S. Patent Publication No. 2009/0068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Patent Publication No. 2009/0111119. Nuclease expression constructs can be readily designed using methods known in the art.

Expression of the fusion proteins may be under the control of a constitutive promoter or an inducible promoter, for example the galactokinase promoter which is activated (de-repressed) in the presence of raffinose and/or galactose and repressed in presence of glucose. In certain embodiments, the promoter self-regulates expression of the fusion protein, for example via inclusion of high affinity binding sites. See, e.g., U.S. Pat. No. 9,624,498.

Delivery

The proteins and/or polynucleotides (e.g., HTT repressors) and compositions comprising the proteins and/or polynucleotides described herein may be delivered to a target cell by any suitable means including, for example, by injection of proteins, via mRNA and/or using an expression construct (e.g., plasmid, lentiviral vector, AAV vector, Ad vector, etc.). In preferred embodiments, the repressor is delivered using AAV9 or AAV6.

Methods of delivering proteins comprising zinc finger proteins as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 8,586,526; 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more DNA-binding protein-encoding sequences. Thus, when one or more HTT repressors are introduced into the cell, the sequences encoding the protein components and/or polynucleotide components may be carried on the same vector or on different vectors. When multiple vectors are used, each vector may comprise a sequence encoding one or multiple HTT repressors or components thereof.

Conventional viral and non-viral based gene transfer methods can be used to introduce nucleic acids encoding engineered HTT repressors in cells (e.g., mammalian cells) and target tissues. Such methods can also be used to administer nucleic acids encoding such repressors (or components thereof) to cells in vitro. In certain embodiments, nucleic acids encoding the repressors are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson (1992) *Science* 256:808-813; Nabel & Felgner (1993) *TIBTECH* 11:211-217; Mitani & Caskey (1993) *TIBTECH* 11:162-166; Dillon (1993) *TIBTECH* 11:167-175; Miller (1992) *Nature* 357:455-460; Van Brunt (1988) *Biotechnology* 6(10):1149-1154; Vigne (1995) *Restorative Neurology and Neuroscience* 8:35-36; Kremer & Perricaudet (1995) *British Medical Bulletin* 51(1):31-44; Haddada et al. in *Current Topics in Microbiology and Immunology* Doerfler and Böhm (eds.) (1995); and Yu et al. (1994) *Gene Therapy* 1:13-26.

Methods of non-viral delivery of nucleic acids include electroporation, lipofection, microinjection, biolistics, virosomes, liposomes, immunoliposomes, polycation or lipid: nucleic acid conjugates, naked DNA, naked RNA, artificial virions, and agent-enhanced uptake of DNA. Sonoporation using, e.g., the Sonitron 2000 system (Rich-Mar) can also be used for delivery of nucleic acids. In a preferred embodiment, one or more nucleic acids are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074,596 and 8,153,773, incorporated by reference herein.

Additional exemplary nucleic acid delivery systems include those provided by Amaxa Biosystems (Cologne, Germany), Maxcyte, Inc. (Rockville, Maryland), BTX Molecular Delivery Systems (Holliston, MA) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™ and Lipofectamine™ RNAIMAX). Cationic and neutral lipids that are suitable for efficient receptor-recognition lipofection of polynucleotides include those of Felgner, International Patent Publication Nos. WO 91/17424 and WO 91/16024. Delivery can be to cells (ex vivo administration) or target tissues (in vivo administration).

The preparation of lipid: nucleic acid complexes, including targeted liposomes such as immunolipid complexes, is well known to one of skill in the art (see, e.g., Crystal (1995) *Science* 270:404-410; Blaese et al. (1995) *Cancer Gene Ther.* 2:291-297; Behr et al. (1994) *Bioconjugate Chem.* 5:382-389; Remy et al. (1994) *Bioconjugate Chem.* 5:647-654; Gao et al. (1995) *Gene Therapy* 2:710-722; Ahmad et al. (1992) *Cancer Res.* 52:4817-4820; U.S. Pat. Nos. 4,186,183; 4,217,344; 4,235,871; 4,261,975; 4,485,054; 4,501,728; 4,774,085; 4,837,028; and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al. (2009) *Nature Biotechnology* 27(7):643).

The use of RNA or DNA viral based systems for the delivery of nucleic acids encoding engineered ZFPs, TALEs or CRISPR/Cas systems take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs, TALEs or CRISPR/Cas systems include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon mouse leukemia virus (MuLV), gibbon ape leukemia virus (GaLV), Simian Immunodeficiency virus (SIV), human immunodeficiency virus (HIV), and combinations thereof (see, e.g., Buchscher et al. (1992) *J. Virol.* 66:2731-2739; Johann et al. (1992) *J. Virol.* 66:1635-1640; Sommerfelt et al. (1990) *Virol.* 176: 58-59; Wilson et al. (1989) *J. Virol.* 63:2374-2378; Miller et al. (1991) *J. Virol.* 65:2220-2224; International Patent Publication No. WO 94/26877).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al. (1987) *Virology* 160:38-47; U.S. Pat. No. 4,797,368; International Patent Publication No. WO 93/24641; Kotin (1994) *Human Gene Therapy* 5:793-801; Muzyczka (1994) *J. Clin. Invest.* 94:1351). Construction of recombinant AAV vectors are described in a number of publications, including U.S. U.S. Pat. No. 5,173,414; Tratschin et al. (1985) *Mol. Cell. Biol.* 5:3251-3260; Tratschin et al. (1984) *Mol. Cell. Biol.* 4:2072-2081; *Hermonat & Muzyczka* (1984) *PNAS* 81:6466-6470; and Samulski et al. (1989) *J. Virol.* 63:03822-3828.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al. (1995) *Blood* 85:3048-305; Kohn et al. (1995) *Nat. Med.* 1:1017-102; Malech et al. (1997) *PNAS* 94(22):12133-12138). PA317/pLASN was the first therapeutic vector used in a gene therapy trial. (Blaese et al. (1995) *Science* 270:475-480). Transduction efficiencies of 50% or greater have been observed for MFG-S packaged vectors. (Ellem et al. (1997) *Immunol Immunother.* 44(1):10-20; Dranoff et al. (1997) *Hum. Gene Ther.* 1:111-2.

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al. (1998) *Lancet* 351(9117): 1702-3; Kearns et al. (1996) *Gene Ther.* 9:748-55). Other AAV serotypes, including AAV1, AAV3, AAV4, AAV5, AAV6, AAV8AAV 8.2, AAV9, and AAV rh 10 and pseudotyped AAV such as AAV2/8, AAV2/5 and AAV2/6 can also be used in accordance with the present invention. In preferred embodiments, AAV9 or AAV6 capsid is used.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al. (1998) *Hum. Gene Ther.* 7:1083-9). Additional examples of the use of adenovirus vectors for gene transfer in clinical trials include Rosenecker et al. (1996) *Infection* 24(1):5-10; Sterman et al. (1998) *Hum. Gene Ther.* 9(7):1083-1089; Welsh et al. (1995) *Hum. Gene Ther.* 2:205-18; Alvarez et al. (1997) *Hum. Gene Ther.* 5:597-613; Topf et al. (1998) *Gene Ther.* 5:507-513; Sterman et al. (1998) *Hum. Gene Ther.* 7:1083-1089.

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging, and integration into the host genome if in the presence of AAV replication proteins. Viral genes is supplemented in a cell line in trans, which contains a helper plasmid encoding the other AAV genes, namely rep and cap, but lacking ITR sequences. The cell line is also infected with adenovirus as a helper. The helper virus promotes replication of the AAV genome and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of tropism to a particular tissue type. Accordingly, a viral vector can be modified to have tropism for a given cell type by expressing a ligand as a fusion protein with a viral coat protein on the outer surface of the virus. The ligand is chosen to have affinity for a receptor known to be present on the cell type of interest. For example, Han et al. (1995) *Proc. Natl. Acad. Sci. USA* 92:9747-9751, reported that Moloney mouse leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion, including direct injection into the brain) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

In certain embodiments, the compositions as described herein (e.g., polynucleotides and/or proteins) are delivered directly in vivo. The compositions (cells, polynucleotides and/or proteins) may be administered directly into the central nervous system (CNS), including but not limited to direct injection into the brain or spinal cord. One or more areas of the brain may be targeted, including but not limited to, the hippocampus, the substantia nigra, the nucleus basalis of Meynert (NBM), the striatum and/or the cortex. Alternatively or in addition to CNS delivery, the compositions may be administered systemically (e.g., intravenous, intraperitoneal, intracardial, intramuscular, intrathecal, subdermal, and/or intracranial infusion). Methods and compositions for delivery of compositions as described herein directly to a subject (including directly into the CNS) include but are not limited to direct injection (e.g., stereotactic injection) via needle assemblies. Such methods are described, for example, in U.S. Pat. Nos. 7,837,668; 8,092,429, relating to delivery of compositions (including expression vectors) to the brain and U.S. Patent Publication No. 2006/0239966, incorporated herein by reference in their entireties.

The effective amount to be administered may vary from patient to patient and according to the mode of administration and site of administration. Accordingly, effective amounts can be determined by one of ordinary skill in the art. After allowing sufficient time for expression of the repressor (typically 4-15 days, for example), analysis of the serum or other tissue levels of the therapeutic polypeptide and comparison to the initial level prior to administration will determine whether the amount being administered is too low, within the right range or too high. In certain embodiments, when using a viral vector such as AAV, the dose administered is between $1\times10^7$ and $5\times10^{15}$ vg/ml (or any value therebetween), even more preferably between $1\times10^{11}$ and $1\times10^{14}$ vg/ml (or any value therebetween), even more preferably between $1\times10^{12}$ and $1\times10^{13}$ vg/ml (or any value therebetween). AAV dosages may also be administered per kilogram or per striatum of the subject including any dosage between $1\times10^7$ and $5\times10^{15}$ vg/kg or vg/striatum (or any value therebetween), even more preferably between $1\times10^7$ and $1\times10^{13}$ vg/kg or vg/striatum (or any value therebetween), even more preferably between $1\times10^8$ and $1\times10^{12}$ vg/kg or vg/striatum (or any value therebetween).

To deliver ZFPs using recombinant adeno-associated viral (rAAV) vectors directly to the human brain, a dose range of $1\times10^7$-$5\times10^{15}$ vg/mL (or any value therebetween, including for example anywhere between $1\times10^{11}$ and $1\times10^{14}$ vg/ml or anywhere $1\times10^{12}$ and $1\times10^{13}$ vg/mL) vector genome per striatum can be applied. A dose range of $1\times10^7$ and $5\times10^{15}$ vg/kg or vg/striatum (or any value therebetween), even more preferably between $1\times10^7$ and $1\times10^{13}$ vg/kg or vg/striatum (or any value therebetween), even more preferably between $1\times10^8$ and $1\times10^{12}$ vg/kg or vg/striatum (or any value therebetween). As noted, dosages may be varied for other brain structures and for different delivery protocols. Methods of delivering rAAV vectors directly to the brain are known in the art. See, e.g., U.S. Pat. Nos. 9,089,667; 9,050,299; 8,337,458; 8,309,355; 7,182,944; 6,953,575; and 6,309,634.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with at least one HTT repressor or component thereof and re-infused back into the subject organism (e.g., patient). In a preferred embodiment, one or more nucleic acids of the HTT repressor are delivered using AAV9. In other embodiments, one or more nucleic acids of the HTT repressor are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074,596 and 8,153,773, incorporated by reference herein in their entireties. Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al. (1992) *J. Exp. Med.* 176:1693-1702).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and lad (differentiated antigen presenting cells) (see Inaba et al. (1992) *J. Exp. Med.* 176:1693-1702).

Stem cells that have been modified may also be used in some embodiments. For example, neuronal stem cells that have been made resistant to apoptosis may be used as therapeutic compositions where the stem cells also contain the ZFP TFs of the invention. Resistance to apoptosis may come about, for example, by knocking out BAX and/or BAK using BAX- or BAK-specific TALENs or ZFNs (see, U.S. Pat. No. 8,597,912) in the stem cells, or those that are disrupted in a caspase, again using caspase-6 specific ZFNs for example. These cells can be transfected with the ZFP TFs or TALE TFs that are known to regulate mutant or wild-type HTT.

Vectors (e.g., retroviruses, adenoviruses, liposomes, etc.) containing therapeutic ZFP nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., $CD34^+$ cells, include adenovirus Type 35.

Vectors suitable for introduction of transgenes into immune cells (e.g., T-cells) include non-integrating lentivirus vectors. See, for example, Naldini et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

As noted above, the disclosed methods and compositions can be used in any type of cell including, but not limited to, prokaryotic cells, fungal cells, Archacal cells, plant cells, insect cells, animal cells, vertebrate cells, mammalian cells and human cells. Suitable cell lines for protein expression are known to those of skill in the art and include, but are not limited to COS, CHO (e.g., CHO-S, CHO-K1, CHO-DG44, CHO-DUXB11), VERO, MDCK, WI38, V79, B14AF28-G3, BHK, Hak, NS0, SP2/0-Ag14, HeLa, HEK293 (e.g., HEK293-F, HEK293-H, HEK293-T), perC6, insect cells such as *Spodoptera fugiperda* (Sf), and fungal cells such as *Saccharomyces, Pischia* and *Schizosaccharomyces*. Progeny, variants and derivatives of these cell lines can also be used. In a preferred embodiment, the methods and composition are delivered directly to a brain cell, for example in the striatum.

Applications

HTT-binding molecules (e.g., ZFPs, TALEs, CRISPR/Cas systems, Ttago, etc.) as described herein, and the nucleic acids encoding them, can be used for a variety of applications. These applications include therapeutic methods in which an HTT-binding molecule (including a nucleic acid encoding a DNA-binding protein) is administered to a subject (e.g., an AAV such as AAV9) and used to modulate the expression of a target gene (and hence protein) within the subject. The modulation can be in the form of repression, for example, repression of mHTT that is contributing to an HD disease state. Alternatively, the modulation can be in the form of activation when activation of expression or increased expression of an endogenous cellular gene can ameliorate a diseased state. In still further embodiments, the modulation can be cleavage (e.g., by one or more nucleases), for example, for inactivation of a mutant HTT gene. As noted above, for such applications, the HTT-binding molecules, or more typically, nucleic acids encoding them are formulated with a pharmaceutically acceptable carrier as a pharmaceutical composition.

The HTT-binding molecules, or vectors encoding them, alone or in combination with other suitable components (e.g. liposomes, nanoparticles or other components known in the art), can be made into aerosol formulations (i.e., they can be "nebulized") to be administered via inhalation. Aerosol formulations can be placed into pressurized acceptable propellants, such as dichlorodifluoromethane, propane, nitrogen, and the like. Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, orally, topically, intraperitoneally, intravesically, intracranially or intrathecally. The formulations of compounds can be presented in unit-dose or multi-dose sealed containers, such as ampules and vials. Injection solutions and suspensions can be prepared from sterile powders, granules, and tablets of the kind previously described.

The dose administered to a patient should be sufficient to affect a beneficial therapeutic response in the patient over time. The dose is determined by the efficacy and $K_d$ of the particular HTT-binding molecule employed, the target cell, and the condition of the patient, as well as the body weight or surface area of the patient to be treated. The size of the dose also is determined by the existence, nature, and extent of any adverse side-effects that accompany the administration of a particular compound or vector in a particular patient.

Beneficial therapeutic response can be measured in a number of ways. For example, improvement in Huntington's associated movement disorders such as involuntary jerking or writhing movements, muscle problems, such as rigidity or muscle contracture (dystonia), slow or abnormal eye movements, impaired gait, posture and balance, difficulty with the physical production of speech or swallowing and the impairment of voluntary movements can be measured. Other impairments, such as cognitive and psychiatric disorders can also be monitored for signs of improvement associated with treatment. The UHDRS scale can be used to quantitate clinical features of the disease. Other biomarkers measurement can also be used for determining outcome, including measurement of mHTT in the CSF.

For patients that are pre-symptomatic, treatment can be especially important because it affords the opportunity to treat the disease prior to the extensive neurodegeneration that occurs in HD. This damage initiates prior to the development of the overt symptoms described above. HD pathology primarily involves the toxic effect of mutant HTT in striatal medium spiny neurons. These medium spiny neurons express high levels of phosphodiesterase 10A (PDE10A)

which regulates cAMP and cGMP signaling cascades that are involved in gene transcription factors, neurotransmitter receptors and voltage-gated channels (Niccolini et al. (2015) *Brain* 138:3016-3029), and it has been shown that the expression of PDE10A is reduced in HD mice and post-mortem studies in humans found the same. Recently, positron emission tomography (PET) ligands have been developed that are ligands for the PDE10A enzyme (e.g. $^{11}$C-IMA107, see, e.g., Niccolini et al., supra; 18FMNI-659, see, e.g., Russell et al. (2014) *JAMA Neurol* 71(12):1520-1528), and these molecules have been used to evaluate pre-symptomatic HD patients. The studies have been shown that PDE10A levels are altered in HD patients even before symptoms develop. Thus, evaluation of PDE10A levels by PET can be done before, during and after treatment to measure therapeutic efficacy of the compositions of the invention. "Therapeutic efficacy" can mean improvement of clinical and molecular measurements, and can also mean protecting the patient from any further decreases in medium spiny neuron function or an increase in spiny neuron loss, or from further development of the overt clinical presentations associated with HD.

The following Examples relate to exemplary embodiments of the present disclosure in which the HTT-modulator comprises a zinc finger protein. It will be appreciated that this is for purposes of exemplification only and that other HTT-modulators (e.g., repressors) can be used, including, but not limited to, TALE-TFs, a CRISPR/Cas system, additional ZFPs, ZFNs, TALENs, additional CRISPR/Cas systems (e.g., Cfp systems), homing endonucleases (meganucleases) with engineered DNA-binding domains.

EXAMPLES

Example 1: m/TT Repressors

Zinc finger proteins targeted to mHTT were engineered essentially as described in U.S. Pat. Nos. 9,234,016; 8,841,260; 6,534,261; U.S. Patent Publication Nos. 2019/0322711; 2017/0096460; 2015/0056705; and 2015/0335708; and 2019/0322711. Table 1 shows the recognition helices of the DNA binding domain of these ZFPs, while Table 2 shows the target sequences of these ZFPs. The ZFPs were evaluated and shown to be bind to their target sites.

ZFPs were operably linked to a KOX repression domain to form ZFP-TF that repress HTT. Table 3 shows the amino acid and nucleotide sequence of the indicated ZFP-TF repressors.

The ZFP TFs transcript were transfected into human cells (e.g., cells derived from HD patients) and expression of HTT and mHTT transcripts were monitored using real-time qRT-PCR. All ZFP-TFs were found to be effective in selectively repressing mutant HTT expression. ZFP-TFs are functional repressors when formulated as plasmids, in mRNA form, in recombinant viral vectors including Ad vectors, lentiviral vectors and/or in AAV vectors (e.g., AAV9 or AAV6).

Example 2: In Vitro Studies

The ability of ZFP-TFs as shown in Table 1 and 3 to selectively repress transcription of the mHTT over the wtHTT allele was assessed in HD patient fibroblasts and stem cell derived neurons.

Briefly, human neuronal stem cells (CAG17 or CAG48 (17 and 48"CAG" repeats disclosed as SEQ ID NO: 23)) were transfected with mRNA encoding the ZFP-TFs of Table 3 or GFP at 0-1500 ng (1500, 300, 150 or 15 ng) and levels of wtHTT and mHTT measured by qPCR 24 hours later. In addition, HD neurons were transduced with AAV6 carrying the ZFP-TF-encoding sequences of Table 3 or GFP at MOI of 10K to 500K (500K, 300K, 100K or 10K).

Figure 2A:
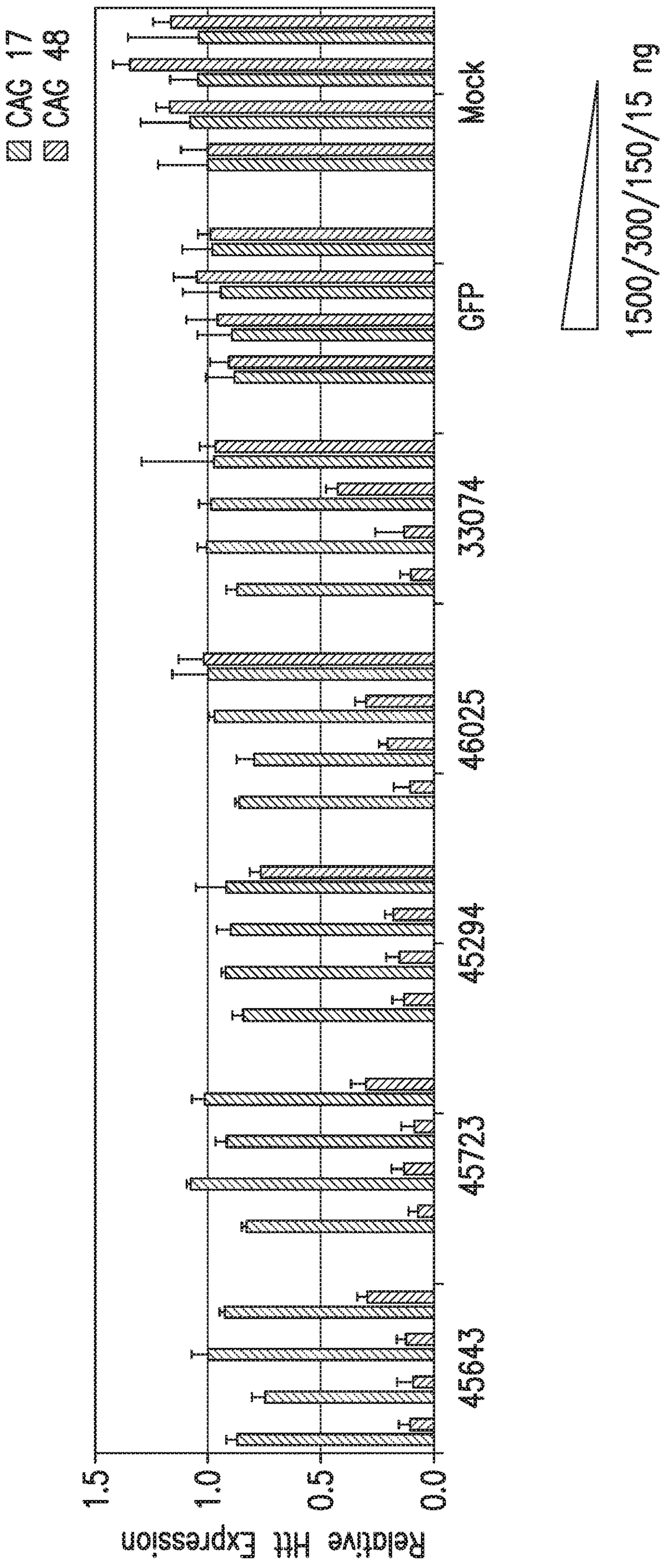
FIG. 2A and FIG. 2B are graphs showing relative HTT expression (wtHTT and mHTT) following introduction of the indicated ZFP-TFs.
Figure 2B:
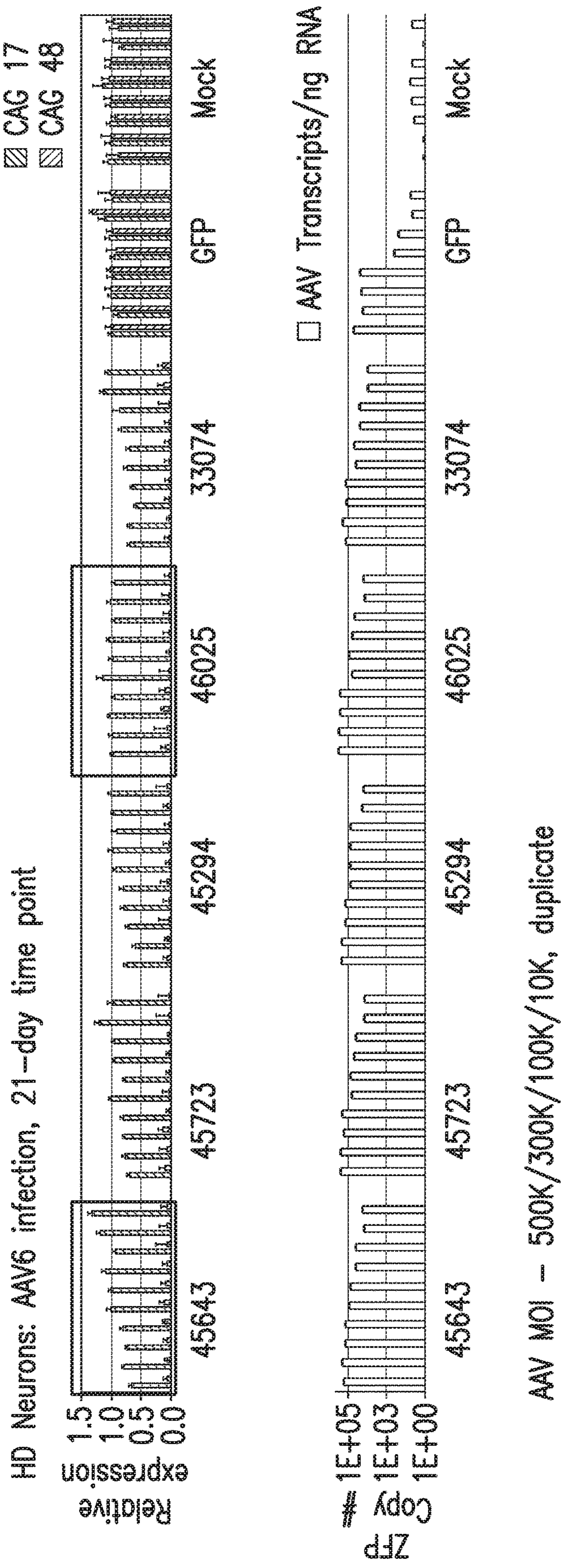
Figure 3:
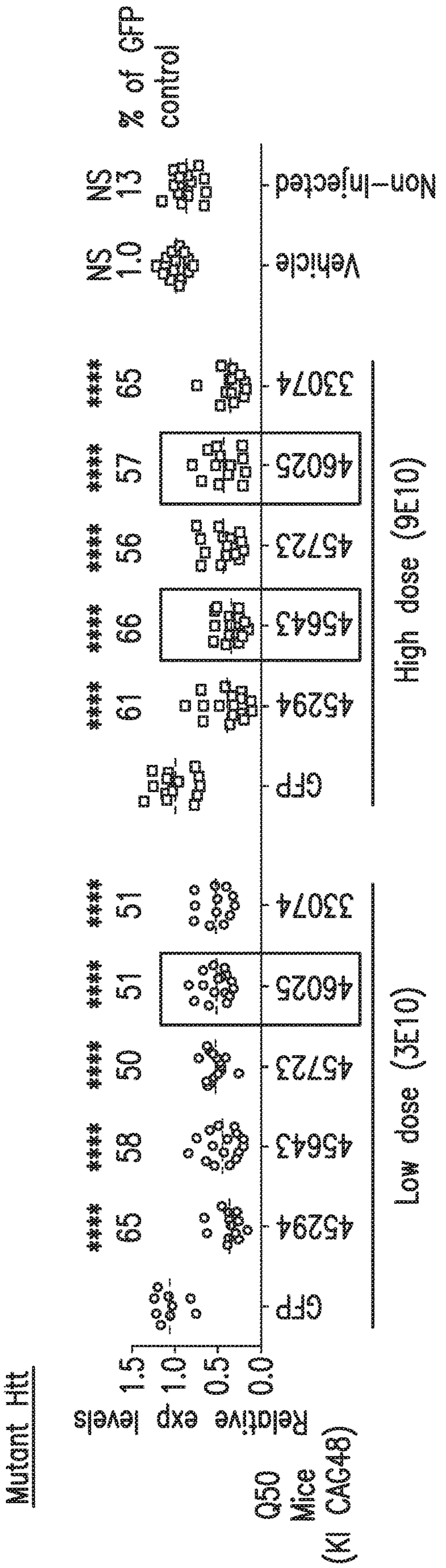
FIG. 3 shows relative expression levels of mutant or wild-type HTT in vivo in subjects treated with the rAAVs carrying the indicated ZFP-TFs and GFP control (GFP) at low (3E10) or high (9E10) doses as well as vehicle and non-injected controls. Repression of mutant HTT (KI allele Q50) expression in Q50 mice which carry a knock-in of 48 CAG repeats (KI CAG48) (48 "CAG" repeats disclosed as SEQ ID NO: 23) is shown.

As shown in FIG. 2, the ZFP-TFs significantly repressed mHITT expression with minimal repression of wild-type HTT.

ZFP-TF 45643 was selected for further study and transient transfection of the transgene mRNA into HD patient fibroblasts was performed to evaluate the ability of the transgene protein to repress mHTT and wtHTT gene transcription. GM02151 fibroblasts (CAG 18 or CAG 45 (18 or 45 "CAG" repeats disclosed as SEQ ID NO: 23)) were transfected with 0-1000 ng mRNA encoding either the rAAV9-ZFP-TFs 45643 transgene or GFP and the levels of wtHTT and mHTT mRNA were measured by qPCR 24 hours later.

Figure 5A:
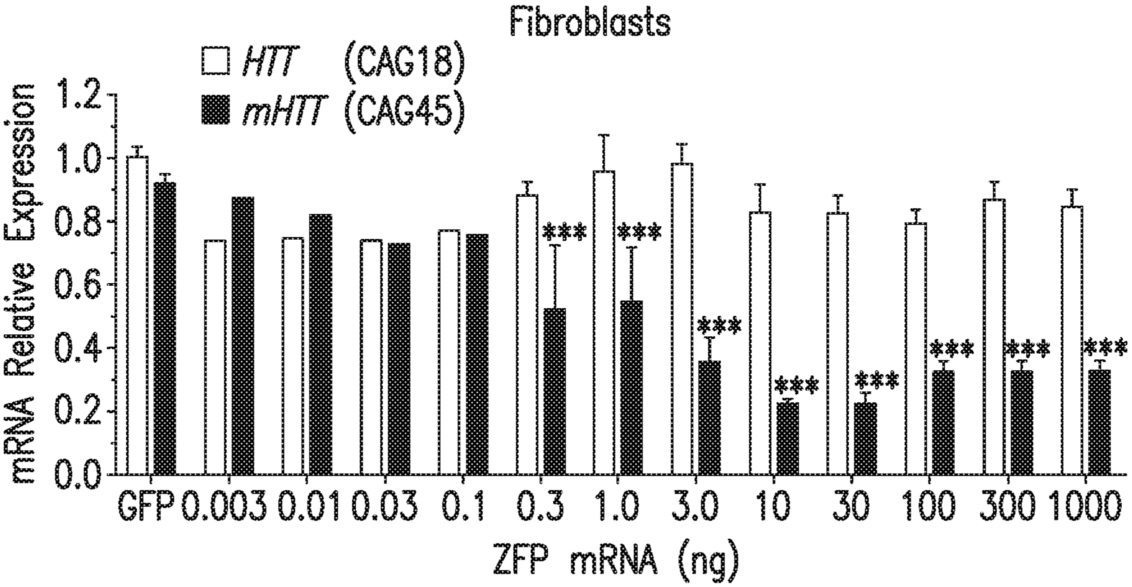
FIGS. 5A and FIG. 5B are graphs showing relative expression of the indicated mRNAs encoding either wild-type HTT (CAG18 (18 "CAG" repeats disclosed as SEQ ID NO: 23)) or mutant HTT (mHTT (CAG45 (45 "CAG" repeats disclosed as SEQ ID NO: 23))) following administration of the indicated dosage of ZFP 45643 mRNA (ng). The left (white) bar under each condition (dosage) shows HTT mRNA expression and the right (black) bar shows mHTT expression.
Figure 5B:
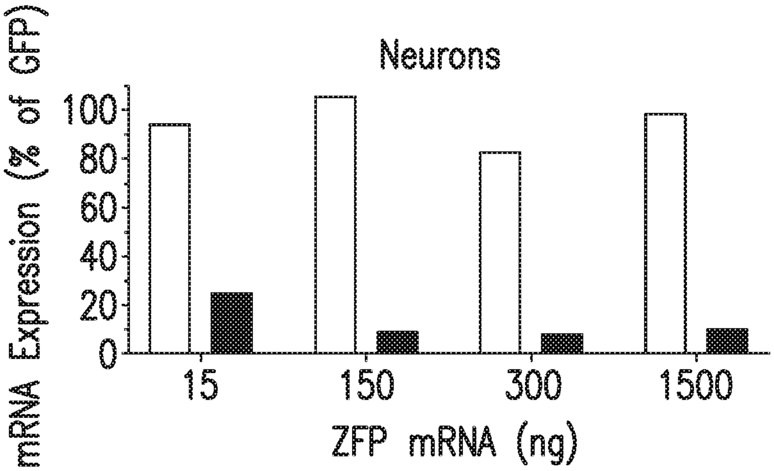

Meta-analysis of data from 6 independent experiments (one-way ANOVA with Dunnett's multiple comparison test) indicated a significant reduction of mHTT mRNA in cells transfected with ≥0.3 ng transgene mRNA ($p<0.001$ compared to GFP transfected cells) with no significant reduction of wtHTT mRNA. See, FIG. 5. These results were confirmed in two additional HD fibroblast lines GM04723 (CAG 15 or CAG 67 (15 or 67 "CAG" repeats disclosed as SEQ ID NO: 23)) and ND30259 (CAG 21 or CAG 38 (21 or 38 "CAG" repeats disclosed as SEQ ID NO: 23)).

To assess repression of mHTT in neurons, HD patient ES cells (GENEA020; CAG 17 or CAG 48 (17 or 48 "CAG" repeats disclosed as SEQ ID NO: 23)) were differentiated to neurons and transiently transfected with 0, 15, 150, or 300 ng mRNA encoding either the ZFP-TFs 45643 transgene or GFP and the levels of wtHTT and mHTT mRNA were measured by qPCR 48 hours later. Neurons transfected with mRNA encoding the ZFP-TFs 45643 transgene had approximately 90% less mHTT mRNA as cells transfected with an equivalent amount of mRNA expressing GFP. Levels of wtHTT mRNA were unchanged across all treatment groups. See, FIG. 5.

Additionally, repression of mHTT and wtHTT transcription was examined 17 days after transduction of rAAV9-ZFP-TFs 45643 into neurons derived from HD patient ES cells (GENEA020; CAG 17/48 ("CAG" repeats disclosed as SEQ ID NO: 23)). Cells were transduced with rAAV9-ZFP-TFs 45643 at 5e4, 1e5, 5e5, 5e6, or 1e7 vg/cell and the levels of transgene mRNA, wtHTT and mHTT mRNA were measured by qPCR 17 days later. Levels of transgene mRNA/cell were approximated based on the number of cells transduced and increased in a dose-dependent manner from 2 to 123 copies/cell. Despite this dose-dependent increase in transgene mRNA, levels of mHTT and wtHTT mRNA were equivalent at all doses. Levels of mHTT were approximately 75% lower than in mock or AAV9-GFP transduced cells, while levels of wtHTT mRNA were unaffected.

Taken together, these results demonstrate that the ZFP-TFs described herein protein selectively target the expanded CAG repeats in the mHTT allele. Further, the results indicate that low levels of transgene expression are sufficient to achieve maximal repression of the mHTT.

Example 3: Specificity

Genome-wide selectivity was assessed in vitro in HD patient cells using microarray analysis for on-target and off-target site. A subset of off-target genes was also analyzed by qPCR analysis.

Figure 4:
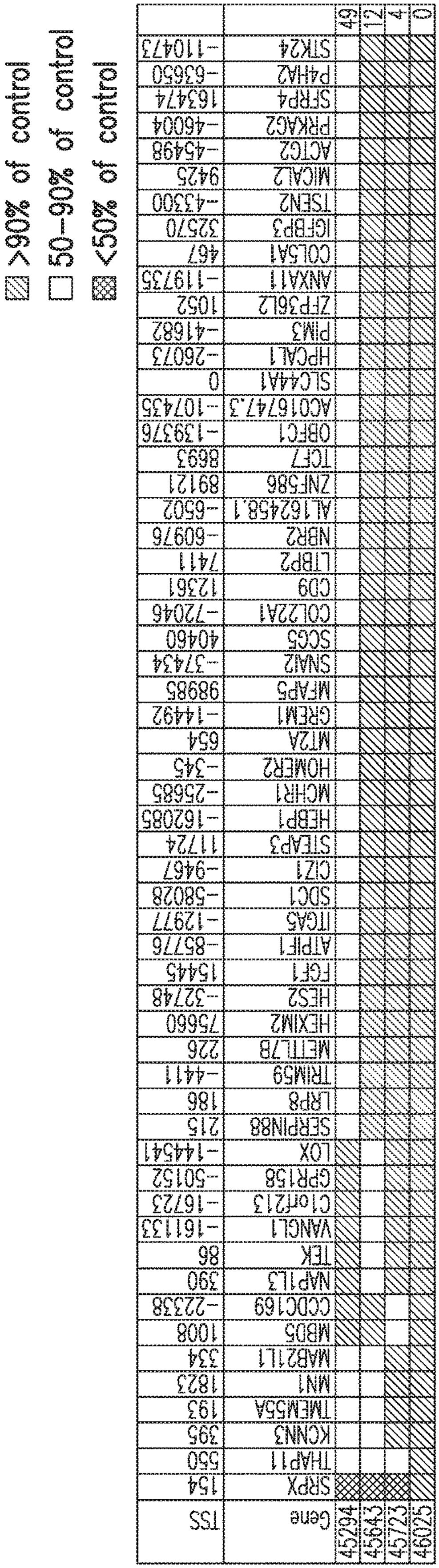
FIG. 4 shows results of microarray analysis of off-target modulation by 4 indicated ZFPs in HD neurons. Unshaded regions show off-target expression at 50-90% of control. Hatched regions show off-target expression levels at greater than 90% of control. Cross-hatched boxes (column 1 of 45294, 45643 and 45723) show off-target expression of less than 50% of the control. As shown the specificity of the ZFP-TFs from most specific to least specific was as follows: 46025>45723>45643>45294. Off target sites are referred to be the gene abbreviated name (e.g., SRPX refers to Sushi-Repeat Containing Protein, X-linked gene, etc.).
Figure 6:
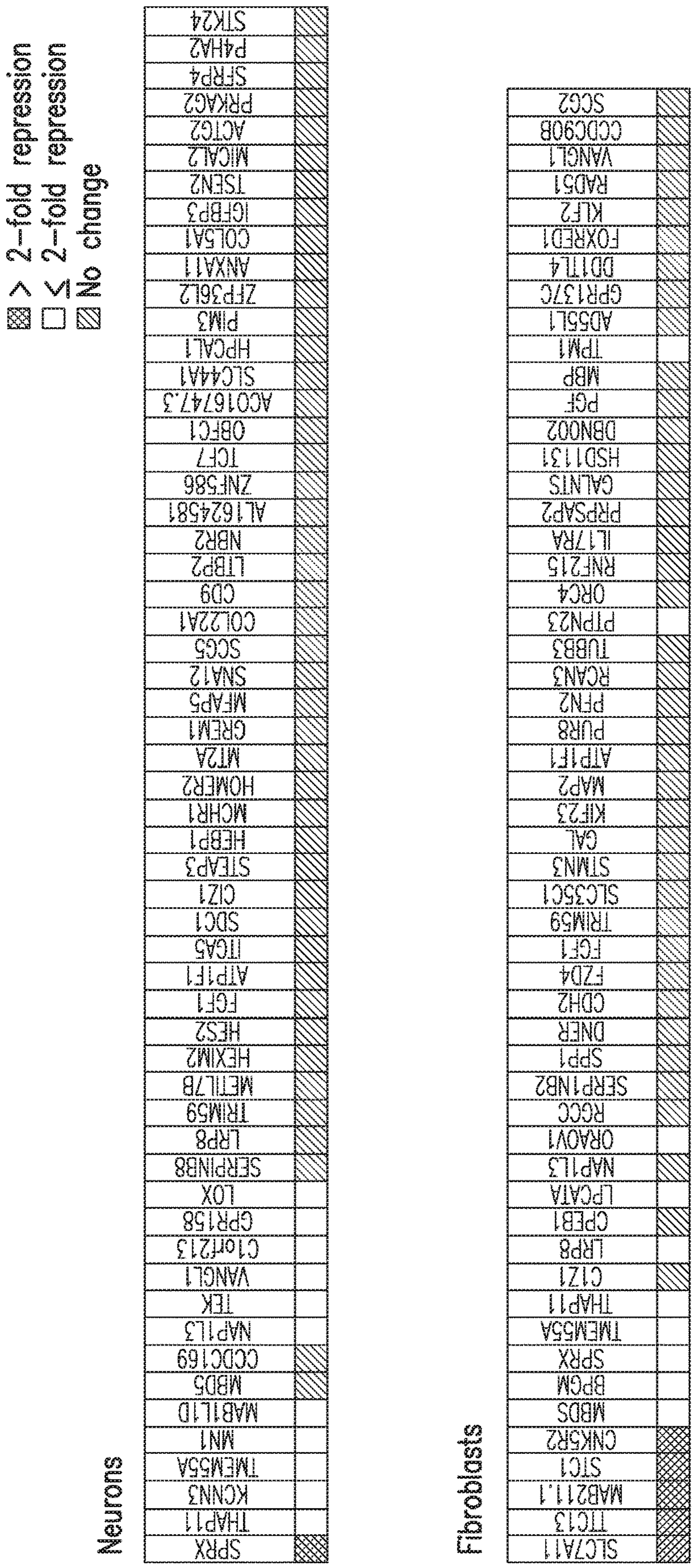
FIG. 6 shows off-target analysis of ZFP-TF 45643 in neurons (top) and fibroblasts (bottom). Unshaded regions show off-target repression of less than or equal to 2-fold repression of control. Hatched regions show no change in modulation as compared to control. Crossed hatched boxes (column 1 showing sprx target in neurons and columns 1-5 (SPRX, TTC12, MAB211.1, STC1 and CNK5R2 target sites in fibroblasts)) show off-target repression of greater than 2-fold.

As shown in FIGS. 4 and 6, as shown for the listed off-target sites, the ZF-TFs exhibited a high degree of specificity for their target sites as determined by qPCR analysis.

Example 4: In Vivo Studies

The in vivo pharmacology of rAAV9-ZFP-TF 45643 was assessed in two HD mouse models, the severe R6/2 model and the more progressive Q175 model. See, e.g., Crook & Housman (2011) *Neuron* 69:423-435. In some studies, rAAV9-ZFP-TF 45643 was administered before onset of disease symptoms, while in others, dosing occurred after onset of disease. In all of these studies, the primary endpoint was repression of mHITT expression. In addition, the impact of rAAV9-ZFP-TF 45643 on motor and cognitive functions was also assessed in some studies.

The effects of rAAV9-ZFP-TF 45643 on mHTT mRNA and protein aggregates were assessed in an aged Q175 mouse model. Q175 mice, 52/53 weeks of age, were administered vehicle, rAAV9-ZFP-TF 45643 (3e8, 3e9, or 3e10 VG/striatum), or rAAV9-GFP (3e8, 3e9, or 3e10 VG/striatum) by stereotaxic instriatal injection. See, FIG. 13. Tissues were collected for qPCR analysis 8 weeks post-surgery and for IHC analysis 8 or 16 weeks post-surgery.

Furthermore, treatment with rAAV9-ZFP-TF 45643 resulted in a dose-dependent increase in the transgene mRNA and a dose-dependent decrease in mHTT mRNA. See, FIGS. 7 and 8. Effects on wild-type mouse HTT were similar to those observed in the rAAV9-GFP treatment groups. Cytoplasmic mHTT protein aggregates were decreased in rAAV9-ZFP-TF 45643 treated striatum compared to vehicle or rAAV9-GFP treated striatum. No effects on nuclear aggregates were observed in any treatment group. Thus, rAAV9-ZFP-TF 45643 can repress mHTT transcription and reduce the levels of cytoplasmic mHITT aggregates when administered after the onset of disease in the Q175 mouse model.

The effects of rAAV9-ZFP-TF 45643 on mHTT mRNA, soluble mHTT protein and mHTT aggregates were assessed in young Q175 mice. Q175 mice, 5 weeks of age, were administered rAAV9-ZFP-TF 45643 (9.2e9, 3.1e10, 9.2e10 VG/mouse), or rAAV9-GFP (5.5e10 VG/mouse) by stereotaxic, bilateral instriatal injection. Tissues were collected 11 weeks post-surgery for qPCR, ELISA, and IHC analysis.

The effects of rAAV9-ZFP-TF 45643 on mHTT mRNA, soluble mHTT protein and mHTT aggregates 33 weeks after treatment were assessed in Q175 mice. Q175 mice, 5 weeks of age, were administered rAAV9-ZFP-TF 45643 (9.2e9, 3.1e10, 9.2e10 VG/mouse), or rAAV9-GFP (5.5e10 VG/mouse) by stereotaxic, bilateral instriatal injection. Motor function (open field, rotamex, tapered balance beam as described in Carter (1999) *J Neurosci.* 19 (8): 3248-3257) were assessed at 16/17, 26/27, and 36/37 weeks of age and cognitive function (FR5/PR) was assessed at 28-35 weeks of age. Tissues were collected 33 weeks post-surgery (38 weeks of age) for qPCR, ELISA, and IHC analysis. At the end of the study brains from spare mice (4-6 per group) were processed for histopathology.

The effects of rAAV9-ZFP-TF 45643 on mHTT mRNA, soluble mHTT protein and mHTT aggregates were assessed in R6/2 mice. R6/2 mice, 4 weeks of age, were administered rAAV9-ZFP-TF 45643 (9.2e9, 3.1e10, 9.2e10 VG/mouse), or rAAV9-GFP (5.5e10 VG/mouse) by stereotaxic, bilateral intrastriatal injection. Motor function was assessed at 5, 7, 9 and 11 weeks of age. Tissues were collected 7 weeks post-surgery (11 weeks of age) for qPCR, ELISA, and IHC analysis.

Figure 7:
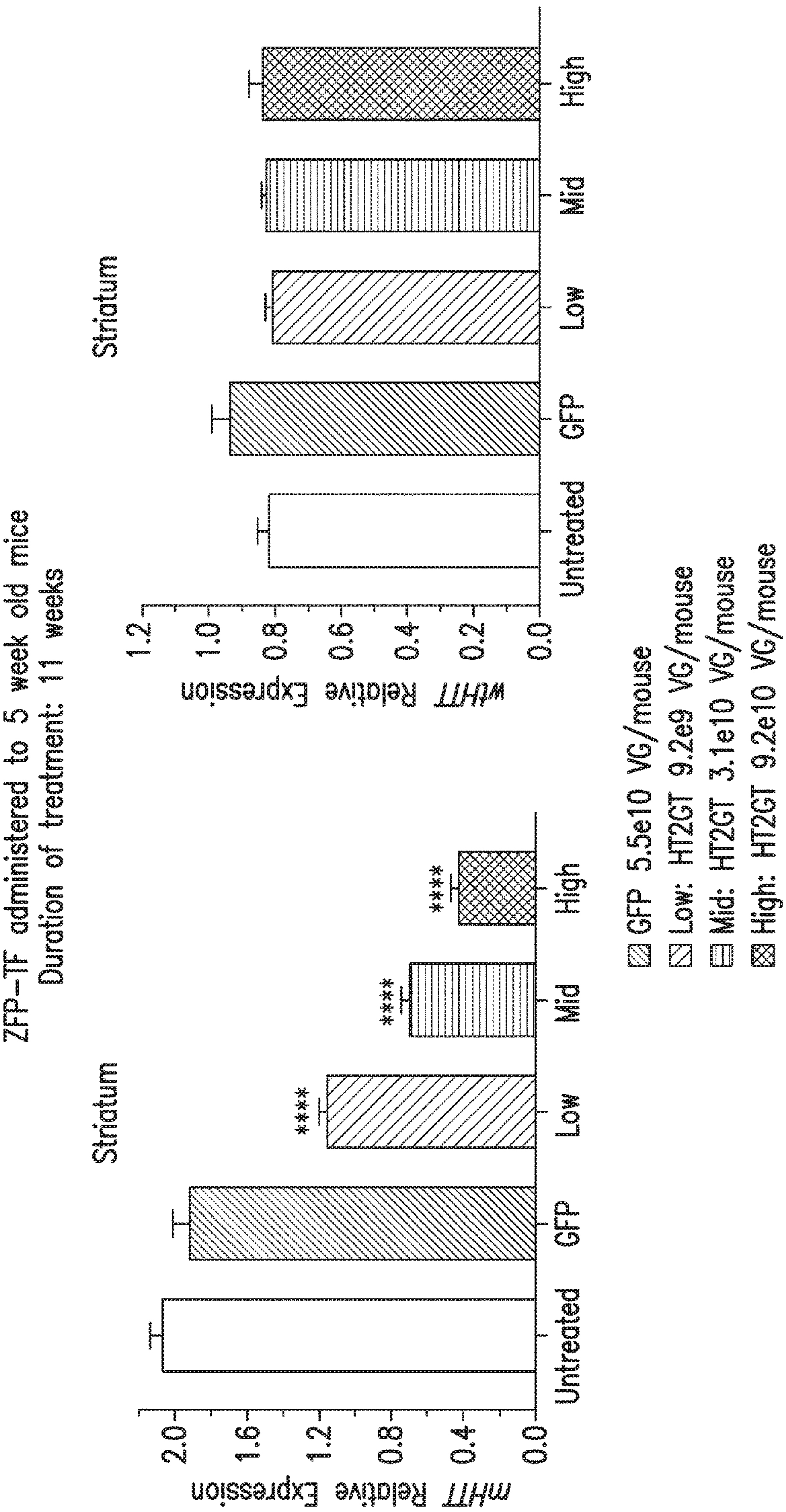
FIG. 7 shows graphs depicting wild-type and mHITT expression in the striatum of control (untreated) and treated Q175 mice, which is a HD rodent model, carrying a knock-in allele of human mutant Huntingtin allele, 11 weeks post-treatment with rAAV vectors encoding GFP or ZFP-TF 45643 at the indicated dosages. The graph on the left shows relative expression of mutant (mHTT) and the graph on the right shows relative expression of wild-type HTT (wtHTT). As shown, significant and preferential repression of mHTT was seen in the ZFP-TF treated animals at all dosages.
Figure 8:
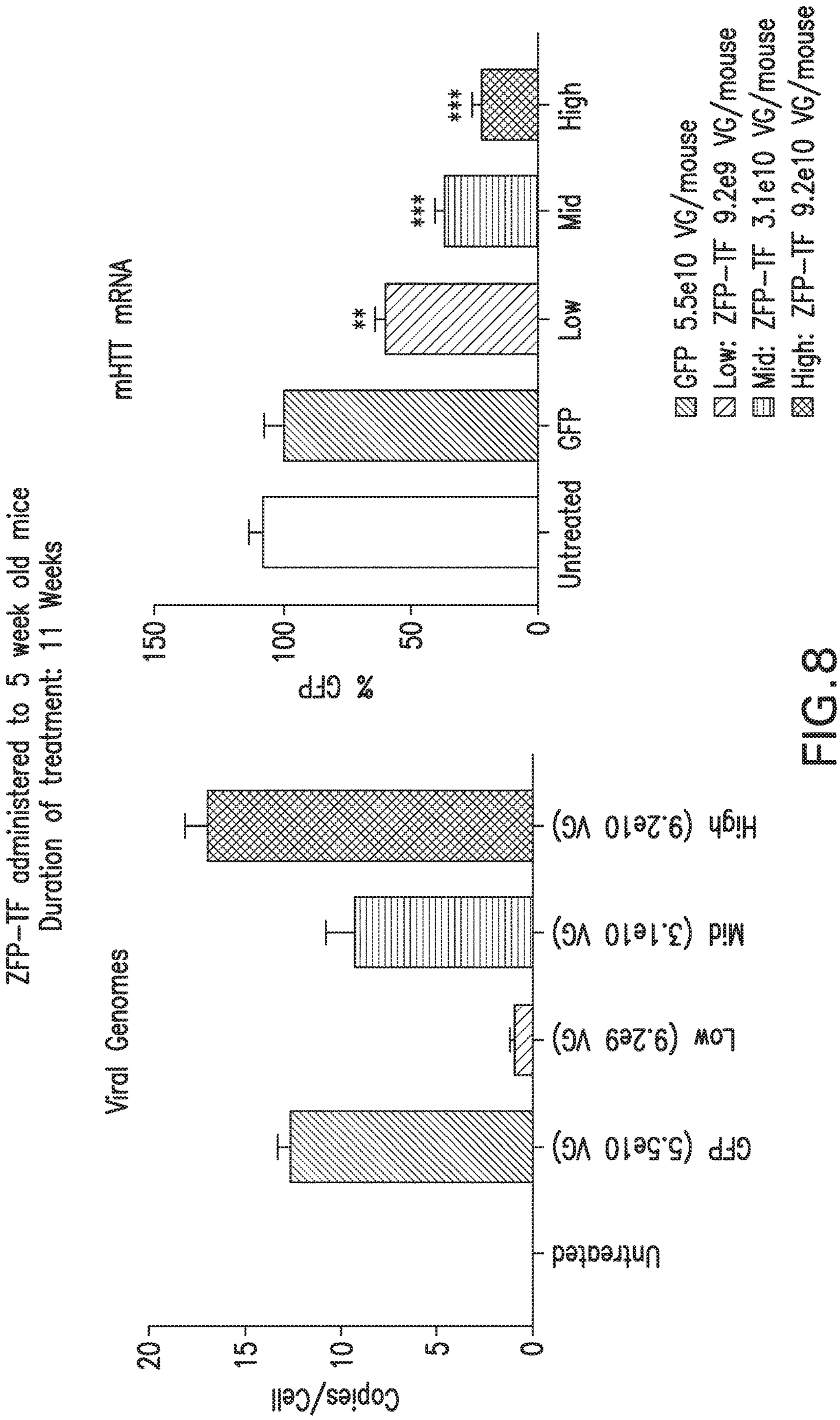
FIG. 8 shows graphs depicting viral genome copies/cell and mHTT mRNA levels in the striatum of control (untreated) and treated Q175 mice 11 weeks post-treatment with AAV vectors encoding GFP or ZFP-TF 45643 at the indicated dosages. The graph on the left shows viral genome copies per cell under the indicated conditions and the graph on the right shows mHTT mRNA levels as a percentage of GFP levels under the indicated conditions. Significant repression of mHTT mRNA levels was observed in the ZFP-TF treated animals at all dosages, including exposure to as low as 1 VG/cell.
Figure 9:
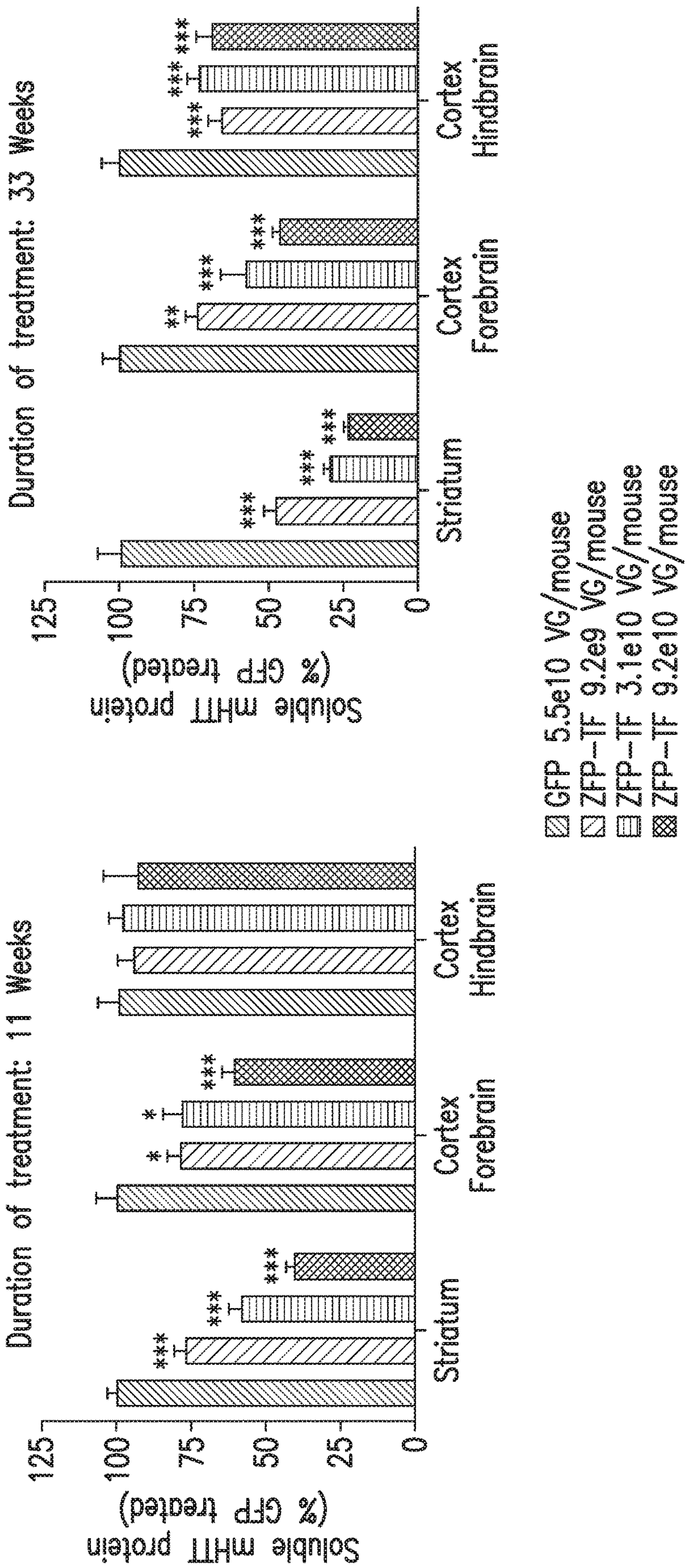
FIG. 9 shows graphs depicting soluble mHTT protein (% GFP treated) in the indicated regions of the brain (striatum, cortex forebrain and cortex hindbrain) 11 weeks (left graph) and 33 weeks (right graph) post-treatment of Q175 mice with rAAV vectors carrying GFP of ZFP-TF 45643 at the indicated dosages. Bars for each region of the brain from left to right show: GFP 5.5e10 VG/mouse; rAAV vectors encoding ZFP-TF 45643 9.2e9 VG/mouse; rAAV vectors encoding ZFP-TF 45643 3.1e10 VG/mouse; and rAAV vectors encoding ZFP-TF 45643 9.2e10 VG/mouse. Dose-dependent significant reduction in soluble mHTT persisted for 33 weeks after single administration of the rAAV vectors encoding ZFP-TF 45643.
Figure 10:
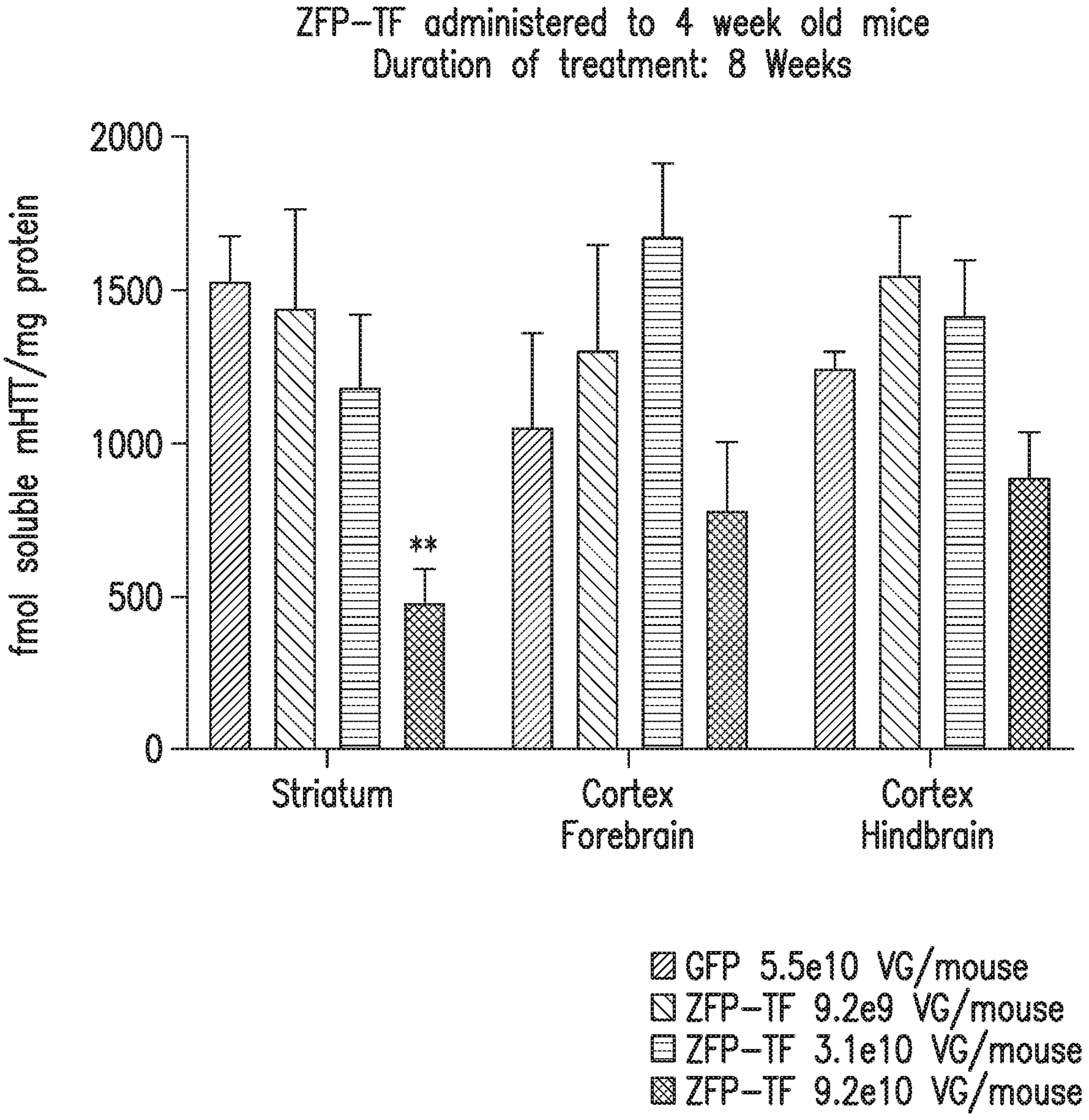
FIG. 10 is a graph depicting soluble mHTT protein (% GFP treated) in the indicated regions of the brain (striatum, cortex forebrain and cortex hindbrain) post-treatment of R6/2 HD mice with AAV vectors carrying GFP of ZFP-TF 45643 at the indicated dosages. Bars for each region of the brain from left to right show: GFP 5.5e10 VG/mouse; rAAV vectors encoding ZFP-TF 45643 9.2e9 VG/mouse; rAAV vectors encoding ZFP-TF 45643 3.1e10 VG/mouse; and rAAV vectors encoding ZFP-TF 45643 9.2e10 VG/mouse. ZFP-TFs significantly reduced soluble mHTT protein production in the severe R6/2 HD mouse model.
Figure 11:
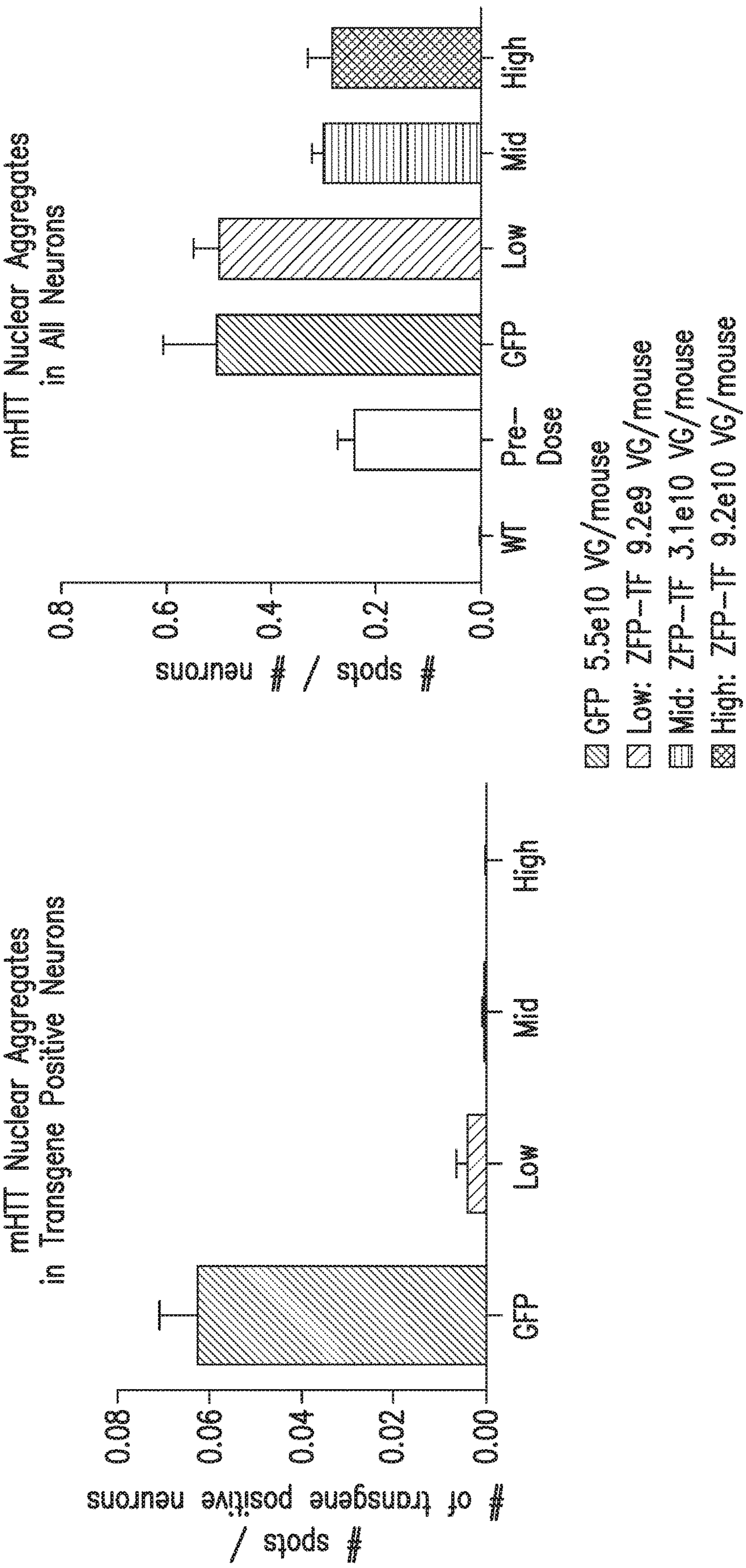
FIG. 11 shows graphs depicting mHTT nuclear aggregation in Q175 and R6/2 mice following administration of rAAV vectors encoding ZFP-TF 45643 at the indicated dose. The left graph shows mHTT nuclear aggregates in transgene positive neurons (# spots/# of transgene positive neurons) in Q175 subjects. The right graph shows mHTT nuclear aggregates (# spots/# neurons) in all neurons under the indicated conditions. ZFP-TF administration reduced mHTT nuclear aggregates in both Q175 and R6/2 subjects.
Figure 12:
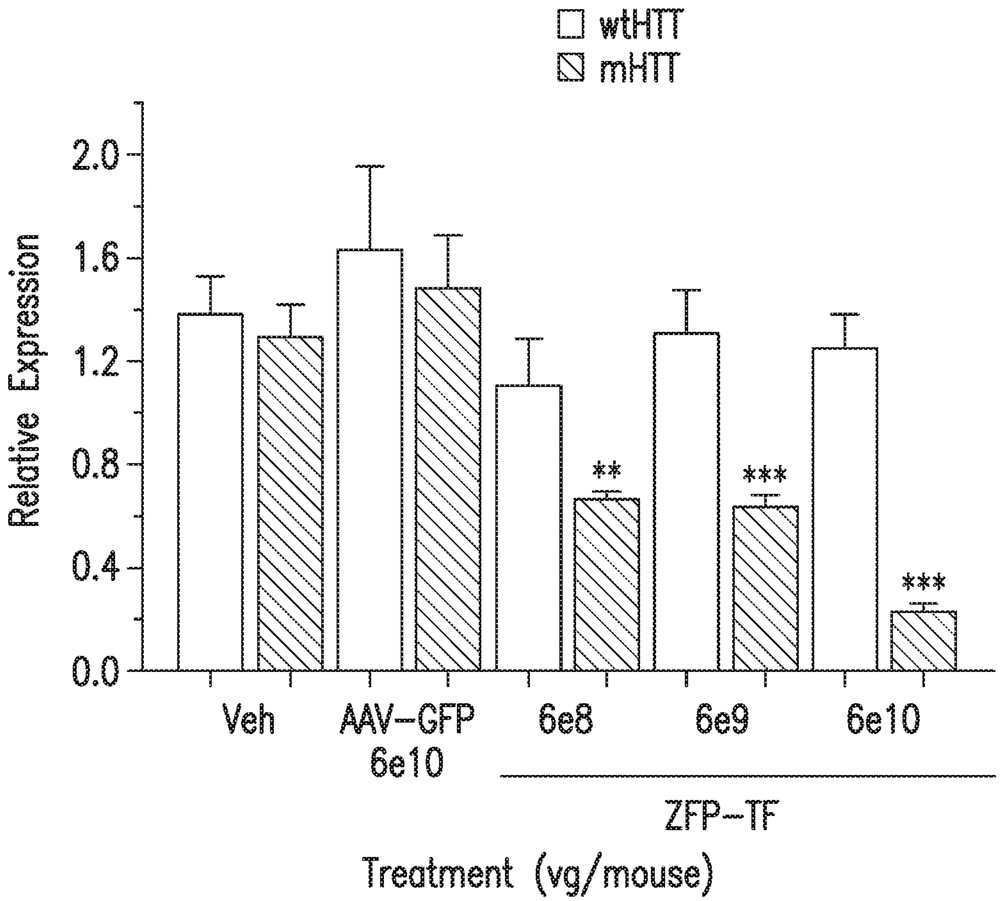
FIG. 12 is a graph depicting relative expression of wild type (wtHTT) and mutant (mHTT) mRNA expression in striatal neurons of 12-month-old Q175 mice under the indicated conditions with a single dose and analyzed 8 weeks after dosing.
Figure 13:
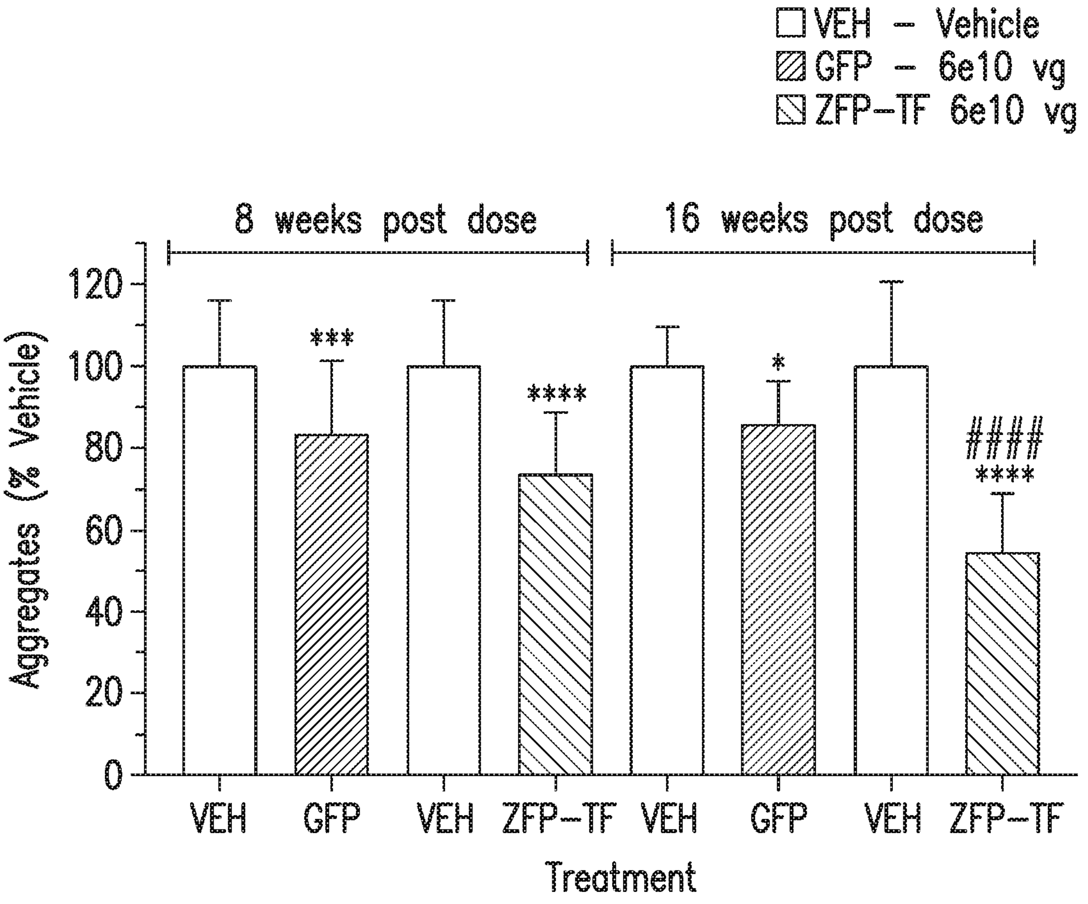
FIG. 13 is a graph depicting perinuclear aggregates (as a percent of vehicle) in 12-month-old Q175 mice at 8 weeks and 16 weeks post-dose under the indicated treatment conditions. ZFP-TF 45643 educed perinuclear mHTT aggregates when administered therapeutically in 12-month-old Q175 mice.

As shown in FIGS. 7-13, the results demonstrate that intrastriatal injection of rAAV9-ZFP-TF 45643 represses synthesis of mHTT in cells that express the transgene protein. In particular, FIGS. 7 and 8 show statistically significant selective repression of mHTT at all ZFP-TF doses (with no reduction in wild-type HTT expression levels). FIG. 9 shows significant reductions in soluble mHTT proteins in subjects treated with ZFP-TFs (all dosages) in striatum and cortex forebrain 11 weeks post-treatment and in striatum, cortex forebrain and cortex hindbrain 33 weeks post-treatment. FIG. 10 shows significant reduction of soluble mHTT in striatum 8 weeks post-treatment with high dose ($9.2\times10^{12}$ vg). FIG. 11 shows a significant reduction in mHTT protein aggregates (as compared to GFP control) in neurons expressing GFP control or a ZFP-TF (all dosages). FIGS. 12 and 13 show significant repression of mHITT expression in subjects treated with AAV ZFP-TFs as described herein.

Figure 14:
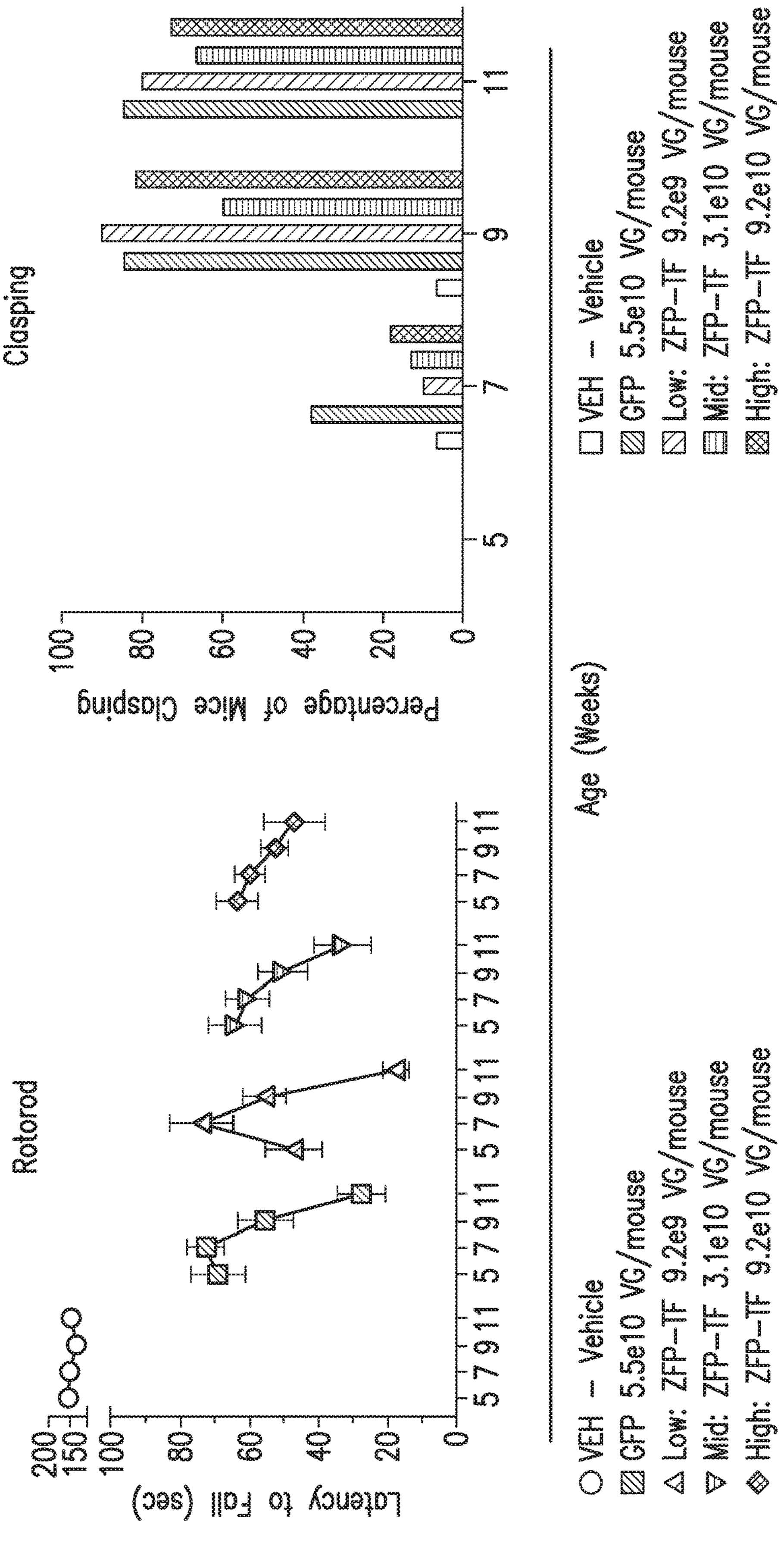
FIG. 14 shows graphs depicting motor function in R6/2 mice under the indicated treatment conditions. The left graph shows results of a rotarod performance test, which measures how long the subject can stay on a rotating rod. The right graph shows percentage of mice exhibiting clasping behavior under the indicated conditions at the indicated age (in weeks).

Furthermore, FIG. 14 shows marked improvement as compared to control of motor function in treated subjects.

Similar in vivo results are obtained using any ZFP-TF described herein (ZFP-TFs comprising ZFPs designated 46025, 45294, 45723, or 33074).

The ZFP-TFs described herein repress transcription of the mHITT allele without significant effects on the wtHIT7 allele or other CAG repeats containing genes in vitro in HD patient cells. In vivo studies in 2 different HD mouse models demonstrated that a single intra-striatal (instriatal) administration of rAAV9-ZFP-TF 45643 given either before or after onset of disease symptoms effectively repressed synthesis of the mHTT mRNA and protein for up to 33 weeks.

All patents, patent applications and publications mentioned herein are hereby incorporated by reference for all purposes in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A zinc finger protein transcription factor (ZFP-TF) comprising a zinc finger protein (ZFP) comprising the recognition helix region sequences in the following order from F1 to F4: F1 comprising SEQ ID NO: 7, F2 comprising SEQ ID NO: 8, F3 comprising SEQ ID NO: 9, and F4 comprising SEQ ID NO: 3.

2. The ZFP-TF of claim 1, comprising the amino acid sequence of SEQ ID NO: 21.

3. A polynucleotide encoding the ZFP-TF of claim 1.

4. The polynucleotide encoding the ZFP-TF of claim 3, comprising the polynucleotide sequence of SEQ ID NO: 16.

5. An rAAV vector comprising one or more polynucleotides of claim 3.

6. The rAAV vector of claim 5, further comprising a sequence encoding a nuclear localization signal (NLS).

7. The rAAV vector of claim 6, further comprising a sequence encoding a promoter driving expression of the ZFP-TF.

8. An rAAV vector comprising one or more polynucleotides of claim 4.

9. A pharmaceutical composition comprising one or more polynucleotides according to claim 3.

10. A pharmaceutical composition comprising one or more polynucleotides according to claim 4.

* * * * *